US012760057B2

(12) United States Patent
Kazarian et al.

(10) Patent No.: US 12,760,057 B2
(45) Date of Patent: Oct. 13, 2026

(54) PURIFICATION METHODS FOR CARBOHYDRATE-LINKED OLIGONUCLEOTIDES

(71) Applicant: AMGEN INC., Thousand Oaks, CA (US)

(72) Inventors: Artaches Kazarian, Belmont, MA (US); Wesley Barnhart, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 1119 days.

(21) Appl. No.: 17/620,645

(22) PCT Filed: Jun. 24, 2020

(86) PCT No.: PCT/US2020/039462

§ 371 (c)(1),
(2) Date: Dec. 17, 2021

(87) PCT Pub. No.: WO2020/264055

PCT Pub. Date: Dec. 30, 2020

(65) Prior Publication Data

US 2022/0363711 A1 Nov. 17, 2022

Related U.S. Application Data

(60) Provisional application No. 62/866,515, filed on Jun. 25, 2019.

(51) Int. Cl.

| | |
|---|---|
| ***C07H 21/00*** | (2006.01) |
| ***B01J 39/02*** | (2006.01) |
| ***B01J 41/04*** | (2017.01) |
| ***C07H 1/06*** | (2006.01) |

(52) U.S. Cl.

CPC .............. *C07H 21/00* (2013.01); *B01J 39/02* (2013.01); *B01J 41/04* (2013.01); *C07H 1/06* (2013.01)

(58) Field of Classification Search

CPC .. C07D 471/04; A61K 31/4545; C07B 59/002
See application file for complete search history.

(56) References Cited

U.S. PATENT DOCUMENTS

| | | | |
|---|---|---|---|
| 6,245,238 | B1 | 6/2001 | Agner |
| 2019/0055558 | A1 | 2/2019 | Uehara et al. |

FOREIGN PATENT DOCUMENTS

| | | | | |
|---|---|---|---|---|
| WO | 1996001268 | A1 | 1/1996 | |
| WO | 1996022299 | A1 | 7/1996 | |
| WO | 2003080834 | A2 | 10/2003 | |
| WO | 2006020768 | A2 | 2/2006 | |
| WO | 2014144767 | A1 | 9/2014 | |
| WO | 2015123264 | A1 | 8/2015 | |
| WO | WO-2015168635 | A2 * | 11/2015 | ............. A61P 43/00 |
| WO | 2017/131236 | A1 | 8/2017 | |
| WO | 2018/215391 | A1 | 11/2018 | |

OTHER PUBLICATIONS

McLaughlin, L. W. Chem. Rev. 1989, 89. 309-319. (Year: 1989).*
GE Healthcare. Handbooks from GE Healthcare. Ion Exchange Chromatography & Chromatofocusing: Principles and Methods. Apr. 2004. (Year: 2004).*
Prakash, T. P., et al. Nucleic Acids Research, 2014, vol. 42, No. 13. (Year: 2014).*
Imtakt. Scherzo C18 Family. Brochure. 2016. Web. (Year: 2016).*
Iwamoto, N., et al. Nature Biotechnology. 2017. vol. 35, pp. 845-851. (Year: 2017).*
Iwamoto, N., et al. Nature Biotechnology. 2017. vol. 35, pp. 845-851. Supporting figure 8. (Year: 2017).*
Kazarian, A. A., et al. Analytica Chimica Acta. 803, 2013, 143-153. (Year: 2013).*
Prakash, T. P., et al. J. Med. Chem. 2016, 59, 2718-2733. (Year: 2016).*
Huang, W., et al. Journal of Chromatography A. 1550, 2018, 75-79. (Year: 2018).*
Imtakt USA, "Scherzo SW-C18," Product Entry Obtained from Internet Archive: Wayback Machine (2018).
Biba et al., "Factors influencing the separation of oligonucleotides using reversed-phase/ion-exchange mixed-mode high performance liquid chromatography columns", J Chromatography A, vol. 1304, pp. 69-77 (2013).
International Search Report and Written Opinion, PCT/US2020/039462, dated Oct. 16, 2020, mailed Oct. 26, 2020.
Kazarian et al., "Simultaneous Analysis of Inorganic Monovalent Anions/Cations Using Mixed-Bed Single-Column Ion Chromatography", Chromatographia, vol. 78, pp. 179-187 (2015).
Zhang and Liu, "Mixed-mode chromatography in pharmaceutical and biopharmaceutical applications", Journal of Pharmaceutical and Biomedical Analysis, vol. 128, pp. 73-88 (2016).
Zhu and Mahato, "Targeted Delivery of siRNA to Hepatocytes and Hepatic Stellate Cells by Bioconjugation", Bioconjug. Chem., vol. 21 (11), pp. 2119-2127 (2010).
Zimmermann et al., "Synthetic oligonucleotide separations by mixed-mode reversed-phase/weak anion-exchange liquid chromatography", J Chromatography A, vol. 1354, pp. 43-55 (2014).

* cited by examiner

*Primary Examiner* — Andrea Olson
*Assistant Examiner* — Samuel L Galster
(74) *Attorney, Agent, or Firm* — Angela L. Purcell

(57) ABSTRACT

The present invention relates to methods for purifying nucleic acids. In particular, the present invention relates to methods for purifying carbohydrate-conjugated oligonucleotides using a mixed-mode stationary phase and a mobile phase comprising a dual salt/organic solvent gradient. Methods for purifying carbohydrate-conjugated oligonucleotides using an anion exchange stationary phase and a mobile phase comprising a dual pH/salt gradient are also described.

23 Claims, 10 Drawing Sheets

Specification includes a Sequence Listing.

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(1)
<223> OTHER INFORMATION: 5'-monophosphate
<220> FEATURE:
<221> NAME/KEY: modified_base
<222> LOCATION: (1)..(21)
<223> OTHER INFORMATION: Positions 1, 3, 5, 7, 9-12, 15, 17, 19, 21
      2'-deoxy-2'-fluoro ("2'-fluoro") ribonucleotide
<220> FEATURE:
<221> NAME/KEY: modified_base
<222> LOCATION: (1)..(21)
<223> OTHER INFORMATION: Positions 2, 4, 6, 8, 13-14, 16, 18, 20
      2'-O-methyl ribonucleotide
<220> FEATURE:
<221> NAME/KEY: modified_base
<222> LOCATION: (2)..(3)
<223> OTHER INFORMATION: phosphorothioate linked nucleoside

<400> SEQUENCE: 1

gugggaagaa agaugaaguu u                                              21


<210> SEQ ID NO 2
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 2, 4, 6, 8, 13, 15, 17, 19, 21
      2'-O-methyl ribonucleotide
<220> FEATURE:
<221> NAME/KEY: modified_base
<222> LOCATION: (1)..(21)
<223> OTHER INFORMATION: Positions 1, 3, 5, 7, 9-12, 14, 16, 18, 20
      2'-deoxy-2'-fluoro ("2'-fluoro") ribonucleotide
<220> FEATURE:
<221> NAME/KEY: modified_base
```

<222> LOCATION: (20)..(21)
<223> OTHER INFORMATION: phosphorothioate linked nucleoside

<400> SEQUENCE: 2
gugggaagaa agaugaaguu u 21

<210> SEQ ID NO 3
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1, 3, 5, 7, 9-12, 15, 17, 19, 21
2'-deoxy-2'-fluoro ("2'-fluoro") ribonucleotide
<220> FEATURE:
<221> NAME/KEY: modified_base
<222> LOCATION: (1)..(21)
<223> OTHER INFORMATION: Positions 2, 4, 6, 8, 13-14, 16, 18, 20
2'-O-methyl ribonucleotide
<220> FEATURE:
<221> NAME/KEY: modified_base
<222> LOCATION: (20)..(21)
<223> OTHER INFORMATION: phosphorothioate linked nucleoside

<400> SEQUENCE: 3
gugggaagaa agaugaaguu u 21

<210> SEQ ID NO 4
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 2, 4, 6, 8-11, 13, 15, 17, 19, 21
2'-deoxy-2'-fluoro ("2'-fluoro") ribonucleotide
<220> FEATURE:
<221> NAME/KEY: modified_base
<222> LOCATION: (1)..(21)
<223> OTHER INFORMATION: Positions 1, 3, 5, 7, 12, 14, 16, 18, 20
2'-O-methyl ribonucleotide
<220> FEATURE:
<221> NAME/KEY: modified_base
<222> LOCATION: (20)..(21)
<223> OTHER INFORMATION: phosphorothioate linked nucleoside

<400> SEQUENCE: 4
gugggaagaa agaugaaguu u 21

<210> SEQ ID NO 5
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 2, 4, 6, 8, 14, 16, 18, 20
2'-O-methyl ribonucleotide
<220> FEATURE:
<221> NAME/KEY: modified_base
<222> LOCATION: (1)..(21)
<223> OTHER INFORMATION: Positions 1, 3, 5, 7, 9-13, 15, 17, 19, 21
2'-deoxy-2'-fluoro ("2'-fluoro") ribonucleotide

<400> SEQUENCE: 5

-continued

```
gcagcugcua cugguucucu u                                                21


<210> SEQ ID NO 6
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1-8, 12-20 2'-O-methyl ribonucleotide
<220> FEATURE:
<221> NAME/KEY: modified_base
<222> LOCATION: (2)..(2)
<223> OTHER INFORMATION: phosphorothioate linked nucleoside
<220> FEATURE:
<221> NAME/KEY: modified_base
<222> LOCATION: (9)..(11)
<223> OTHER INFORMATION: 2'-deoxy-2'-fluoro ("2'-fluoro") ribonucleotide
<220> FEATURE:
<221> NAME/KEY: modified_base
<222> LOCATION: (21)..(21)
<223> OTHER INFORMATION: phosphorothioate linked nucleoside, inverted
      deoxyribonucleotide attached by 3'-3' linkage

<400> SEQUENCE: 6

cagccccuua aacuuauacg a                                                21


<210> SEQ ID NO 7
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1-6, 8, 13-21 2'-O-methyl
      ribonucleotide
<220> FEATURE:
<221> NAME/KEY: modified_base
<222> LOCATION: (1)..(21)
<223> OTHER INFORMATION: Positions 7, 9-12 2'-deoxy-2'-fluoro
      ("2'-fluoro") ribonucleotide
<220> FEATURE:
<221> NAME/KEY: modified_base
<222> LOCATION: (20)..(21)
<223> OTHER INFORMATION: phosphorothioate linked nucleoside

<400> SEQUENCE: 7

cuucaugccu uucuacaguu u                                                21


<210> SEQ ID NO 8
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1-6, 8, 13-21 2'-O-methyl
      ribonucleotide
<220> FEATURE:
<221> NAME/KEY: modified_base
<222> LOCATION: (1)..(21)
<223> OTHER INFORMATION: Positions 7, 9-12 2'-deoxy-2'-fluoro
      ("2'-fluoro") ribonucleotide
<220> FEATURE:
<221> NAME/KEY: modified_base
<222> LOCATION: (20)..(21)
<223> OTHER INFORMATION: phosphorothioate linked nucleoside
```

-continued

<400> SEQUENCE: 8
uucaugccuu ucuacaguuu u 21

<210> SEQ ID NO 9
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1-6, 8, 13-21 2'-O-methyl ribonucleotide
<220> FEATURE:
<221> NAME/KEY: modified_base
<222> LOCATION: (1)..(21)
<223> OTHER INFORMATION: Positions 7, 9-12 2'-deoxy-2'-fluoro ("2'-fluoro") ribonucleotide
<220> FEATURE:
<221> NAME/KEY: modified_base
<222> LOCATION: (20)..(21)
<223> OTHER INFORMATION: phosphorothioate linked nucleoside

<400> SEQUENCE: 9
gcuucaugcc uuucuacauu u 21

<210> SEQ ID NO 10
<211> LENGTH: 22
<212> TYPE: DNA
<213> ORGANISM: Artificial Sequence
<220> FEATURE:
<223> OTHER INFORMATION: synthetic polynucelotide
<220> FEATURE:
<221> NAME/KEY: misc_feature
<222> LOCATION: (1)..(1)
<223> OTHER INFORMATION: inverted abasic nucleotide attached by 3'-3' linkage
<220> FEATURE:
<221> NAME/KEY: modified_base
<222> LOCATION: (2)..(22)
<223> OTHER INFORMATION: Positions 2-7, 9, 11, 16-22 2'-O-methyl ribonucleotide
<220> FEATURE:
<221> NAME/KEY: modified_base
<222> LOCATION: (2)..(22)
<223> OTHER INFORMATION: Positions 8, 10, 12-15 2'-deoxy-2'-fluoro ("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 10
ngcuucaugc ccuucuacau uu 22

<210> SEQ ID NO 11
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3' linkage
<220> FEATURE:
<221> NAME/KEY: modified_base
<222> LOCATION: (2)..(22)
<223> OTHER INFORMATION: Positions 2-7, 9, 14-22 2'-O-methyl ribonucleotide
<220> FEATURE:

<221> NAME/KEY: modified_base
<222> LOCATION: (2)..(22)
<223> OTHER INFORMATION: Positions 8, 10-13 2'-deoxy-2'-fluoro
("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 11
ngcuucaugc ccuucuacau uu 22

<210> SEQ ID NO 12
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(21)
<223> OTHER INFORMATION: Positions 1-6, 8, 13-21 2'-O-methyl
ribonucleotide
<220> FEATURE:
<221> NAME/KEY: modified_base
<222> LOCATION: (1)..(21)
<223> OTHER INFORMATION: Positions 7, 9-12 2'-deoxy-2'-fluoro
("2'-fluoro") ribonucleotide
<220> FEATURE:
<221> NAME/KEY: modified_base
<222> LOCATION: (20)..(21)
<223> OTHER INFORMATION: phosphorothioate linked nucleoside

<400> SEQUENCE: 12
gcuucauccc uuucuacauu u 21

<210> SEQ ID NO 13
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3'
linkage
<220> FEATURE:
<221> NAME/KEY: modified_base
<222> LOCATION: (2)..(22)
<223> OTHER INFORMATION: Positions 2-7, 9, 14-22 2'-O-methyl
ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro
("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 13
ngcuucaugc cuuucuacau uu 22

<210> SEQ ID NO 14
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3'
linkage
<220> FEATURE:
<221> NAME/KEY: modified_base
<222> LOCATION: (2)..(22)
<223> OTHER INFORMATION: Positions 2-7, 9, 14-22 2'-O-methyl
ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro
("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 14
ncaugccuuu cuacaguggu uu 22

<210> SEQ ID NO 15
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3'
linkage
<220> FEATURE:
<221> NAME/KEY: modified_base
<222> LOCATION: (2)..(22)
<223> OTHER INFORMATION: Positions 2-7, 9, 14-22 2'-O-methyl
ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro
("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 15
naugccuuuc uacaguggcu uu 22

<210> SEQ ID NO 16
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3'
linkage
<220> FEATURE:
<221> NAME/KEY: modified_base
<222> LOCATION: (2)..(22)
<223> OTHER INFORMATION: Positions 2-7, 9, 14-22 2'-O-methyl
ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro
("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 16
ncugcuucau gccuuucuaa uu 22

<210> SEQ ID NO 17
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3' linkage
<220> FEATURE:
<221> NAME/KEY: modified_base
<222> LOCATION: (2)..(22)
<223> OTHER INFORMATION: Positions 2-7, 9, 14-22 2'-O-methyl ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro ("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 17
ngcuucaugc cuuucuacaa uu 22

<210> SEQ ID NO 18
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3' linkage
<220> FEATURE:
<221> NAME/KEY: modified_base
<222> LOCATION: (2)..(22)
<223> OTHER INFORMATION: Positions 2-7, 9, 14-22 2'-O-methyl ribonucleotide
<220> FEATURE:
<221> NAME/KEY: modified_base
<222> LOCATION: (2)..(22)
<223> OTHER INFORMATION: Positions 8, 10-13 2'-deoxy-2'-fluoro ("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 18
nuucaugccu uucuacagua uu 22

<210> SEQ ID NO 19
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: inverted abasic nucleotide attached by 3'-3' linkage
<220> FEATURE:
<221> NAME/KEY: modified_base
<222> LOCATION: (2)..(22)
<223> OTHER INFORMATION: Positions 3, 5, 7, 9, 14-22 2'-O-methyl ribonucleotide
<220> FEATURE:
<221> NAME/KEY: modified_base
<222> LOCATION: (2)..(22)
<223> OTHER INFORMATION: Positions 2, 4, 6, 8, 10-13 2'-deoxy-2'-fluoro ("2'-fluoro") ribonucleotide
<220> FEATURE:
<221> NAME/KEY: modified_base
<222> LOCATION: (21)..(22)
<223> OTHER INFORMATION: phosphorothioate linked nucleoside

<400> SEQUENCE: 19
ngcuucaugc cuuucuacau uu 22

<210> SEQ ID NO 20
<211> LENGTH: 21
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(20)
<223> OTHER INFORMATION: Positions 1-8, 10, 15-20 2'-O-methyl ribonucleotide
<220> FEATURE:
<221> NAME/KEY: modified_base
<222> LOCATION: (1)..(20)
<223> OTHER INFORMATION: Positions 9, 11-14 2'-deoxy-2'-fluoro ("2'-fluoro") ribonucleotide
<220> FEATURE:
<221> NAME/KEY: misc_feature
<222> LOCATION: (21)..(21)
<223> OTHER INFORMATION: phosphorothioate linked nucleoside, inverted abasic nucleotide attached by 3'-3' linkage

<400> SEQUENCE: 20
cugcuucaug ccuuucuaca n 21

<210> SEQ ID NO 21
<211> LENGTH: 23
<212> TYPE: DNA
<213> ORGANISM: Artificial Sequence
<220> FEATURE:
<223> OTHER INFORMATION: synthetic polynucleotide
<220> FEATURE:
<221> NAME/KEY: modified_base
<222> LOCATION: (1)..(1)
<223> OTHER INFORMATION: 5'-monophosphate
<220> FEATURE:
<221> NAME/KEY: modified_base
<222> LOCATION: (1)..(21)
<223> OTHER INFORMATION: Positions 1, 3, 5, 8-11, 13, 15-23 2'-O-methyl ribonucleotide
<220> FEATURE:
<221> NAME/KEY: modified_base
<222> LOCATION: (1)..(21)
<223> OTHER INFORMATION: Positions 2, 4, 6-7, 12, 14 2'-deoxy-2'-fluoro ("2'-fluoro") ribonucleotide
<220> FEATURE:
<221> NAME/KEY: modified_base
<222> LOCATION: (2)..(3)
<223> OTHER INFORMATION: phosphorothioate linked nucleoside
<220> FEATURE:
<221> NAME/KEY: modified_base
<222> LOCATION: (20)..(21)
<223> OTHER INFORMATION: phosphorothioate linked nucleoside -continued

<400> SEQUENCE: 21

```
cucguauaac aauaaggggc uuu                                               23
```

PURIFICATION METHODS FOR CARBOHYDRATE-LINKED OLIGONUCLEOTIDES

CROSS-REFERENCE TO RELATED APPLICATIONS

This application claims the benefit of U.S. Provisional Application No. 62/866,515, filed Jun. 25, 2019, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Jun. 24, 2020, is named A-2362-WO-PCT_SeqList_ST25 and is 13 kilobytes in size.

FIELD OF THE INVENTION

The present invention relates to the field of nucleic acid purification. In particular, the invention relates to methods for purifying a carbohydrate-oligonucleotide conjugate compound using mixed-mode chromatography. The methods allow for the purification of intact carbohydrate-oligonucleotide conjugate compounds from unconjugated oligonucleotides and other impurities. The methods also allow for the separation of phosphorothioate diastereomers of oligonucleotides containing one or more phosphorothioate internucleotide linkages. The invention also relates to methods of purifying a carbohydrate-oligonucleotide conjugate compound using an anion-exchange stationary phase and elution with a dual pH/salt gradient. Such methods can be used in combination with the mixed-mode chromatography methods described herein to purify carbohydrate-oligonucleotide conjugate compounds.

BACKGROUND OF THE INVENTION

Progress in developing nucleic acid-based therapeutics that have a gene silencing mechanism of action continues to be made. However, one key challenge to the development of this class of therapeutic molecules is the difficulty in targeting the therapeutic nucleic acid to the appropriate tissue or cell. One approach for delivering nucleic acid molecules to liver cells is to conjugate the therapeutic nucleic acid to a carbohydrate molecule, which binds to receptors, such as the asialoglycoprotein receptor, on the surface of liver cells. These and other chemical modifications to the nucleic acid structure, which promote delivery and enhance in vivo potency and stability, necessitate the development of novel purification methods for these increasingly complex molecules.

Both ion-exchange and reversed-phase liquid chromatography have been previously employed to purify natural and synthetic oligonucleotides. Reversed-phase chromatographic methods typically require the use of a 5' protecting group, such as 5'-O-trityl, which protects the 5' hydroxyl group during synthesis of the oligonucleotide and is then used to purify the full-length oligonucleotide sequences ("trityl on" sequences) from the truncated failure sequences that do not have the protecting group ("trityl off" sequences). These reversed-phase methods often require additional steps following purification to remove the protecting group thereby increasing the cost and overall processing time. Ion-exchange-based chromatographic purification methods are generally less costly than reversed-phase methods due to the use of aqueous-based mobile phases. However, because the structural modifications made to current nucleic acid therapeutics to enable in vivo use increase the complexity of these molecules and the types of impurities generated during their synthesis, conventional ion-exchange and reversed-phase chromatographic methods are not always adequate to achieve the necessary purity and yield. Thus, there is a need in the art for novel preparative purification methods for nucleic acid therapeutics, such as carbohydrate-conjugated oligonucleotides.

SUMMARY OF THE INVENTION

The present invention is based, in part, on the development of an orthogonal separation method to conventional anion-exchange chromatographic methods for oligonucleotides, particularly carbohydrate-conjugated oligonucleotides. In certain embodiments, the methods of the invention utilize a mixed-mode stationary phase comprising strong anion exchange ligands, strong cation exchange ligands, and hydrophobic ligands (e.g. alkyl chains) in combination with a tailored mobile phase that capitalizes on both the ion-exchange and hydrophobic interactions to control retention of the carbohydrate-conjugated oligonucleotide and separation from impurities, including unconjugated oligonucleotides and failure sequences.

Accordingly, the present invention provides a method for purifying a carbohydrate-oligonucleotide conjugate compound from one or more impurities. In one embodiment, the method comprises contacting a solution comprising the carbohydrate-oligonucleotide conjugate compound and one or more impurities with a mixed-mode matrix; passing a mobile phase described herein through the mixed-mode matrix; and collecting elution fractions from the mixed-mode matrix, wherein one or more impurities are eluted in a first set of elution fractions and the carbohydrate-oligonucleotide conjugate compound is eluted in a second set of elution fractions, thereby separating the carbohydrate-oligonucleotide conjugate compound from the impurities.

The mixed-mode matrix employed in the methods of the invention is generally comprised of ligands having positively-charged functional groups, negatively-charged functional groups, and hydrophobic functional groups. In certain embodiments, the mixed-mode matrix comprises a strong anion exchange ligand, a strong cation exchange ligand, and a hydrophobic ligand. The strong anion exchange ligand and strong cation exchange ligand remain fully charged over a wide pH range and exhibit little or no variation in ion exchange capacity with changes in pH. In some embodiments, the strong anion exchange ligand comprises a quaternary amine. In these and other embodiments, the strong cation exchange ligand comprises a sulfonyl functional group. The hydrophobic ligand in the mixed-mode matrix may comprise alkyl groups (e.g. isopropyl, propyl, t-butyl, butyl, and C8 to C18 alkyl chains) or aryl groups (e.g. phenyl group). In certain embodiments, the hydrophobic ligand comprises an alkyl group. In one embodiment, the hydrophobic ligand comprises an octadecyl carbon chain (e.g. C18 alkyl chain). In another embodiment, the hydrophobic ligand comprises an octyl carbon chain (e.g. C8 alkyl chain). The mixed-mode matrix used in the methods of the invention may have a pore size less than about 20 nm, for example from about 8 nm to about 15 nm or from about 11 nm to about 14 nm.

The mobile phases used in the mixed-mode chromatography methods of the invention have a pH of about 7.0 to about 8.5 and comprise a buffer and an organic solvent. The buffer can be any buffer able to maintain the pH in the target range, such as sodium phosphate, Tris hydrochloride, HEPES, or MOPS, and can be present in a concentration of about 20 mM to about 200 mM. In one embodiment, the mobile phase comprises about 80 mM to about 110 mM of a buffer. Suitable organic solvents that can be used in the mobile phase include acetonitrile, methanol, propanol, isopropanol, ethanol, butanol, tetrahydrofuran, or acetone. The concentration of the organic solvent in the mobile phase may increase over the course of the separation. For instance, in some embodiments, the increase in concentration of organic solvent in the mobile phase is a concentration gradient, for example, from about 8% (v/v) to about 20% (v/v), from about 10% (v/v) to about 18% (v/v), from about 9% (v/v) to about 16% (v/v), or from about 11% (v/v) to about 17% (v/v). The concentration gradient can be a linear gradient or a step gradient. In certain embodiments, the concentration of organic solvent in the mobile phase at the beginning of the separation is at least 8% (v/v) and increases over the course of the separation. In other embodiments, the concentration of organic solvent in the mobile phase at the beginning of the separation is at least 10% (v/v) and increases over the course of the separation.

The mobile phases used in the mixed-mode chromatography methods of the invention also comprise an elution salt, the concentration of which increases over the time period of the separation. The elution salt can be, for example, sodium salts, potassium salts, ammonium salts, trimethylammonium salts, triethylammonium salts, chloride salts, bromide salts, nitrate salts, nitrite salts, iodide salts, perchlorate salts, acetate salts, or formate salts. In certain embodiments, the elution salt is sodium bromide, potassium bromide, ammonium bromide, sodium chloride, potassium chloride, or ammonium chloride. During the separation, the increase in concentration of the elution salt in the mobile phase can be a concentration gradient of the elution salt, for example from 0 M to about 1 M or from about 0.5 M to about 1 M. The concentration gradient can be a linear gradient or a step gradient. In some embodiments, the mobile phase has a pH of about 7.0 to about 8.0 and comprises a Tris hydrochloride buffer, acetonitrile, and sodium bromide, where the concentration of sodium bromide increases at a gradient of about 0.5 M to about 1 M over the course of the separation. In such embodiments, the concentration of acetonitrile in the mobile phase may increase at a gradient of about 8% (v/v) to about 20% (v/v) over the course of the separation.

Another aspect of the invention relates to the development of an improved anion-exchange chromatography-based method for purifying carbohydrate-oligonucleotide conjugate compounds. The improved method employs an anion-exchange stationary phase comprising strong anion exchange ligands and a mobile phase comprising both increasing pH and salt gradients. Thus, in certain embodiments, the present invention provides a method for purifying a carbohydrate-oligonucleotide conjugate compound from one or more impurities comprising contacting a solution comprising the carbohydrate-oligonucleotide conjugate compound and one or more impurities with an anion-exchange matrix; passing a mobile phase described herein through the anion-exchange matrix; and collecting elution fractions from the anion-exchange matrix, wherein the carbohydrate-oligonucleotide conjugate compound is eluted in a first set of elution fractions and one or more impurities are eluted in a second set of elution fractions, thereby separating the carbohydrate-oligonucleotide conjugate compound from the impurities.

The anion-exchange matrix employed in the methods of the invention comprises ligands having positively-charged functional groups. Preferably, the anion-exchange matrix comprises a strong anion exchange ligand that exhibits little to no variation in ion exchange capacity with changes in pH and remains positively-charged over a wide pH range. In some embodiments, the strong anion exchange ligand comprises a quaternary amine, such as quaternary aminoethyl, quaternary ammonium, and quaternary aminomethyl.

The mobile phases used in the anion-exchange chromatography methods of the invention comprise a buffer and an organic solvent. The organic solvent can be any of those described herein that are suitable for use with the mobile phase for the mixed-mode chromatography methods of the invention, such as acetonitrile, methanol, propanol, isopropanol, ethanol, butanol, tetrahydrofuran, or acetone. In some embodiments, the organic solvent may be present in the mobile phase for the anion-exchange chromatography methods of the invention at a concentration of about 1% (v/v) to about 50% (v/v) or from about 1% (v/v) to about 20% (v/v). The pH of the mobile phase for the anion-exchange chromatography method will generally be at least about 8.5 and increase over the course of the separation. For instance, in some embodiments, the pH of the mobile phase increases from about 8.5 to about 11 over the course of the separation. In other embodiments, the pH of the mobile phase increases from about 9.0 to about 10.5 over the course of the separation. The buffer can be any buffer capable of maintaining the pH of the mobile phase across the range of the pH gradient. One particularly suitable buffer for the range of the pH gradient is sodium phosphate.

The mobile phases for the anion-exchange chromatography methods of the invention also comprise an elution salt, the concentration of which increases over the course of the separation. The elution salts included in the mobile phase can be any of the elution salts described herein for use with the mobile phases for the mixed-mode chromatography methods of the invention. For example, in certain embodiments, the elution salt is sodium bromide, potassium bromide, ammonium bromide, sodium chloride, potassium chloride, or ammonium chloride. In certain embodiments, the elution salt is sodium chloride. The increase in concentration of the elution salt in the mobile phase can be a concentration gradient (e.g. linear gradient or step gradient) of the elution salt, for example, from 0 M to about 2 M or from 0 M to about 1 M.

The mobile phases for the anion-exchange chromatography methods of the invention preferably comprise a dual pH/salt gradient—i.e. both the pH of the mobile phase and the concentration of the elution salt in the mobile phase increase over the course of the separation. In some embodiments, the mobile phase comprises a pH gradient from about 8.5 to about 11 and an elution salt gradient from about 0 M to about 1 M. In other embodiments, the mobile phase comprises a pH gradient from about 9.0 to about 10.5 and an elution salt gradient from about 0.3 M to about 0.7 M. In still other embodiments, the mobile phase comprises a pH gradient from about 8.5 to about 10.5 and an elution salt gradient from about 0 M to about 0.8 M. In certain embodiments, the mobile phase for the anion-exchange chromatography methods of the invention comprises a sodium phosphate buffer, acetonitrile, and sodium chloride, where the concentration of sodium chloride increases at a gradient of about 0 M to about 1 M and the pH of the mobile phase increases from a pH of about 8.5 to about 11 over the course of the separation.

In certain embodiments of the mixed-mode and anion-exchange chromatography methods of the invention, the methods further comprise isolating the elution fractions or set of elution fractions comprising the carbohydrate-oligonucleotide conjugate compound. The isolated elution fractions can be subject to one or more further processing steps, such as one or more further purifications steps (e.g. desalting), annealing reactions to hybridize the carbohydrate-oligonucleotide conjugate compound with a complementary strand to form a double-stranded RNA interference agent, and formulation steps to prepare pharmaceutical compositions of the carbohydrate-oligonucleotide conjugate compound for administration to patients for therapeutic purposes. The mixed-mode chromatography methods of the invention can be used in combination with the anion-exchange chromatography methods of the invention to purify a carbohydrate-oligonucleotide conjugate compound. In some embodiments, the anion-exchange chromatography method of the invention is conducted initially followed by the mixed-mode chromatography method. In other embodiments, the mixed-mode chromatography method of the invention is conducted initially followed by the anion-exchange chromatography method.

The oligonucleotide components of the carbohydrate-oligonucleotide conjugate compounds that can be purified according to the methods of the invention can be naturally-occurring oligonucleotides or synthetic oligonucleotides. In some embodiments, the oligonucleotide components of the carbohydrate-oligonucleotide conjugate compounds are therapeutic oligonucleotides designed to target a gene or RNA molecule associated with a disease or disorder. Such therapeutic oligonucleotides include a short hairpin RNA (shRNA), a precursor miRNA (pre-miRNA), an anti-miRNA oligonucleotide (e.g. antagomir and antimiR), an antisense oligonucleotide, a small interfering RNA (siRNA), a microRNA (miRNA), or a miRNA mimetic.

The carbohydrate component of the carbohydrate-oligonucleotide conjugate compounds that can be purified according to the methods of the invention may comprise one or more hexose or hexosamine units, such as galactose, galactosamine, or N-acetyl-galactosamine. In certain embodiments, the carbohydrate component of the carbohydrate-oligonucleotide conjugate compounds comprises a multivalent galactose moiety or multivalent N-acetyl-galactosamine moiety. Such multivalent sugar moieties may be trivalent or tetravalent. The carbohydrate-oligonucleotide conjugate compounds that can be purified according to the methods of the invention may comprise one or more modified nucleotides, such as 2'-modified nucleotides. In some embodiments, the carbohydrate-oligonucleotide conjugate compounds comprise at least one phosphorothioate internucleotide linkage. Incorporation of phosphorothioate internucleotide linkages creates diastereomers of the carbohydrate-oligonucleotide conjugate compounds. In some embodiments, the mixed-mode chromatography methods of the invention provide for the separation of different sets of such phosphorothioate diastereomers.

μm) and a 15.7 mM N,N-Diisopropylethylamine (DIEA), 50 mM Hexafluoro-2-propanol mobile phase with elution by an acetonitrile gradient. Traces A-G correspond to separations for compound nos. 13-10, 13-13, 13-07, 32-10, 32-07, 32-04, and 32-01, respectively. Detection at 260 nm absorbance. For visualization purposes, each of traces B-G were offset by 0.3 min (x-axis) and 1e+6 (y-axis) from the previous trace. The predominant peaks in each trace had approximately the same retention time.

Figure 5:
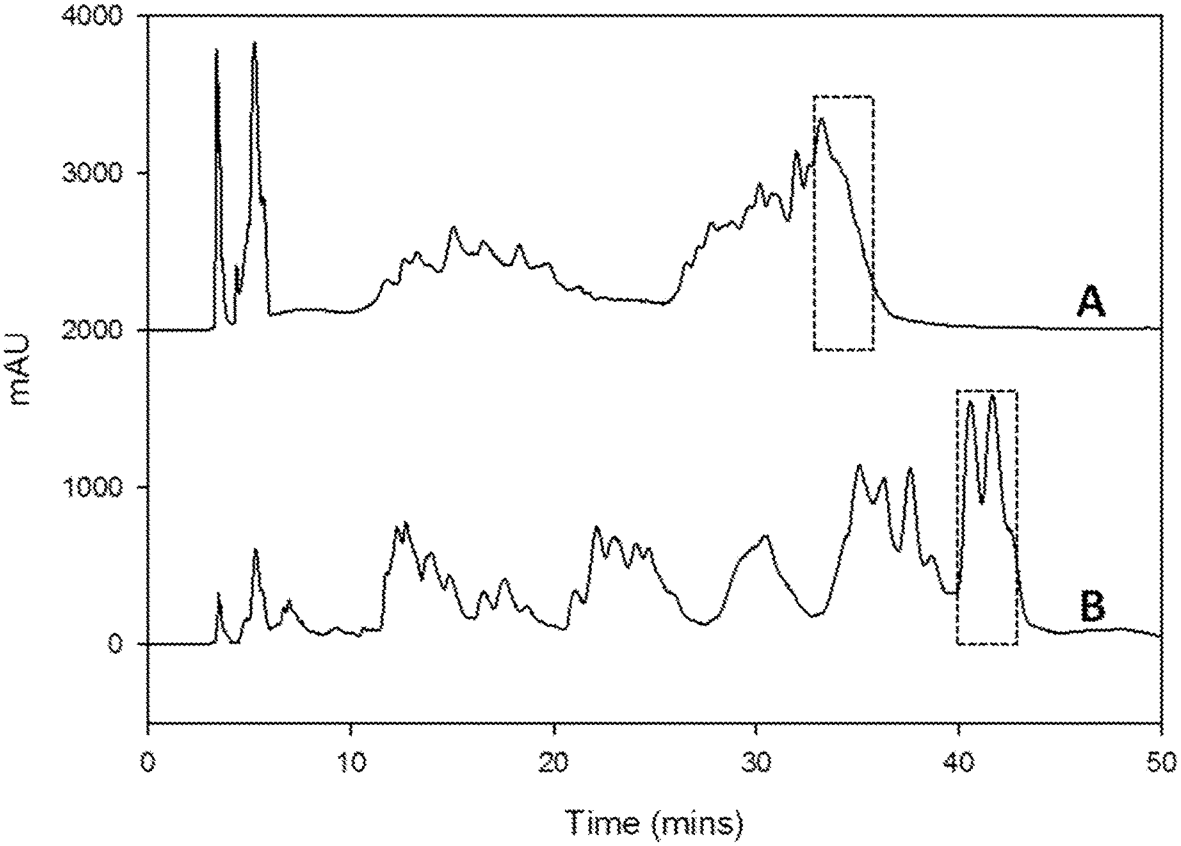

FIG. 5 depicts preparative chromatograms for two GalNAc-conjugated oligonucleotides (compound nos. 19-04 (Trace A) and 19-07 (Trace B)) using a mixed-mode stationary phase (Scherzo SS-C18 column). A solution comprising each GalNAc-conjugated oligonucleotide was separated on the Scherzo SS-C18 column (10×250 mm, 3 μm) at a flow rate of 5 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 45-70% mobile phase B in 0-40 min, 70-80% mobile phase B at 40-45 min, 80% mobile phase B at 45-50 min, 45% mobile phase B at 51 min (hold for 15 min). Detection was by UV absorbance at 260 nm. Dashed boxes represent fractions that were collected for further analysis.

Figure 6:
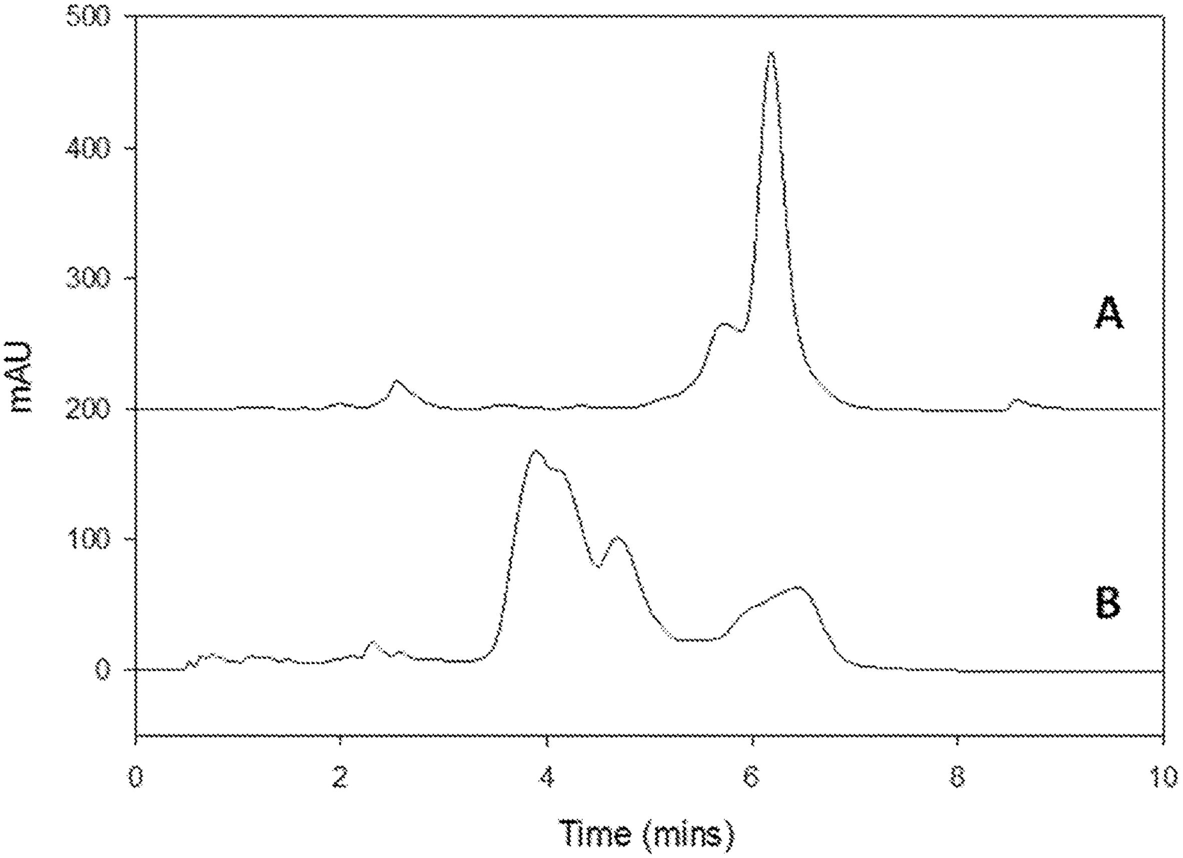

FIG. 6 shows analytical chromatograms for separation of a solution comprising an oligonucleotide comprising four phosphorothioate internucleotide linkages (compound no. 08-17) using either an anion exchange stationary phase (TSK-gel SuperQ-5PW column; Trace A) or a mixed-mode stationary phase (Scherzo SS-C18 column; Trace B). For the separation shown in Trace A, a solution comprising the oligonucleotide was separated on the TSK-gel SuperQ-5PW column (7.5×75 mm, 10 μm) at a flow rate of 2 mL/min using a 20 mM $Na_2HPO_4$, 15% acetonitrile (v/v) mobile phase, pH 8.5 with elution by a pH/salt gradient. For the separation shown in Trace B, a solution comprising the oligonucleotide was separated on the Scherzo SS-C18 column (4.6×50 mm, 3 μm) at a flow rate of 1 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 55-80% mobile phase B in 0-8 min, 80% mobile phase B at 8-10 min, 55% mobile phase B at 10.1-12 min. Detection was by UV absorbance at 260 nm.

Figure 7A:
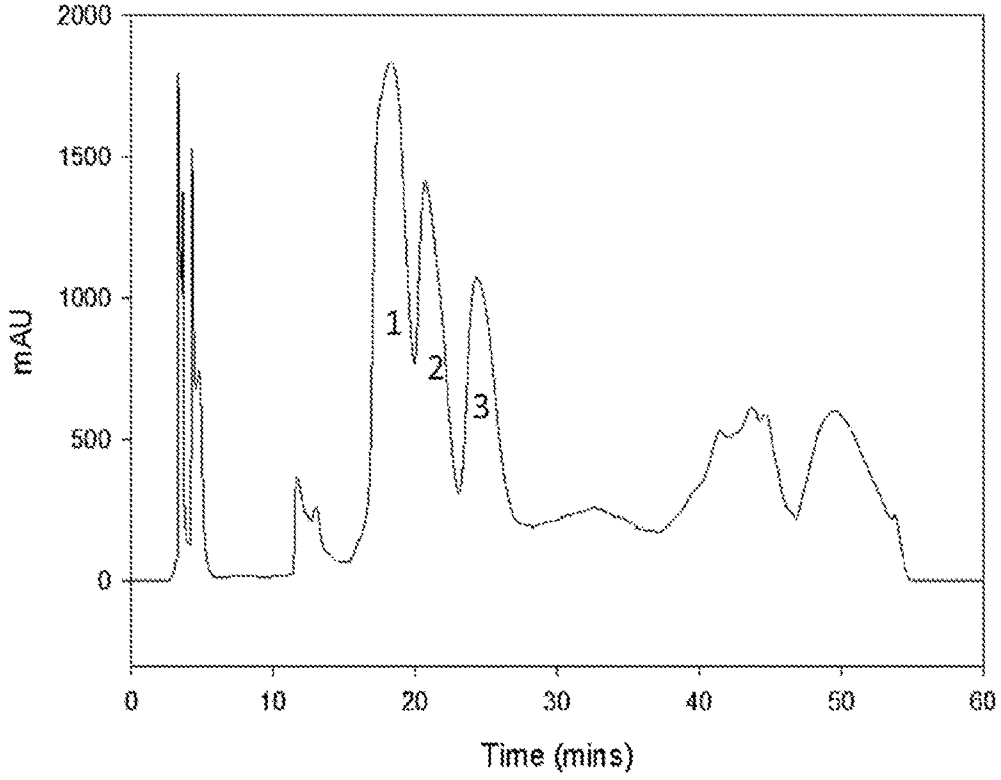

FIG. 7A depicts a preparative chromatogram of the separation of a solution comprising an oligonucleotide comprising four phosphorothioate internucleotide linkages (compound no. 08-17) using a mixed-mode stationary phase (Scherzo SS-C18 column). A solution comprising the oligonucleotide was separated on the Scherzo SS-C18 column (10×250 mm, 3 μm) at a flow rate of 5 mL/min using. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 45-70% mobile phase B in 0-40 min, 70-80% mobile phase B at 40-45 min, 80% mobile phase B at 45-50 min, 45% mobile phase B at 51 min (hold for 15 min). Peaks labeled 1, 2, and 3 were collected as separate fractions and subject to further analysis. Detection was by UV absorbance at 260 nm.

Figure 7B:
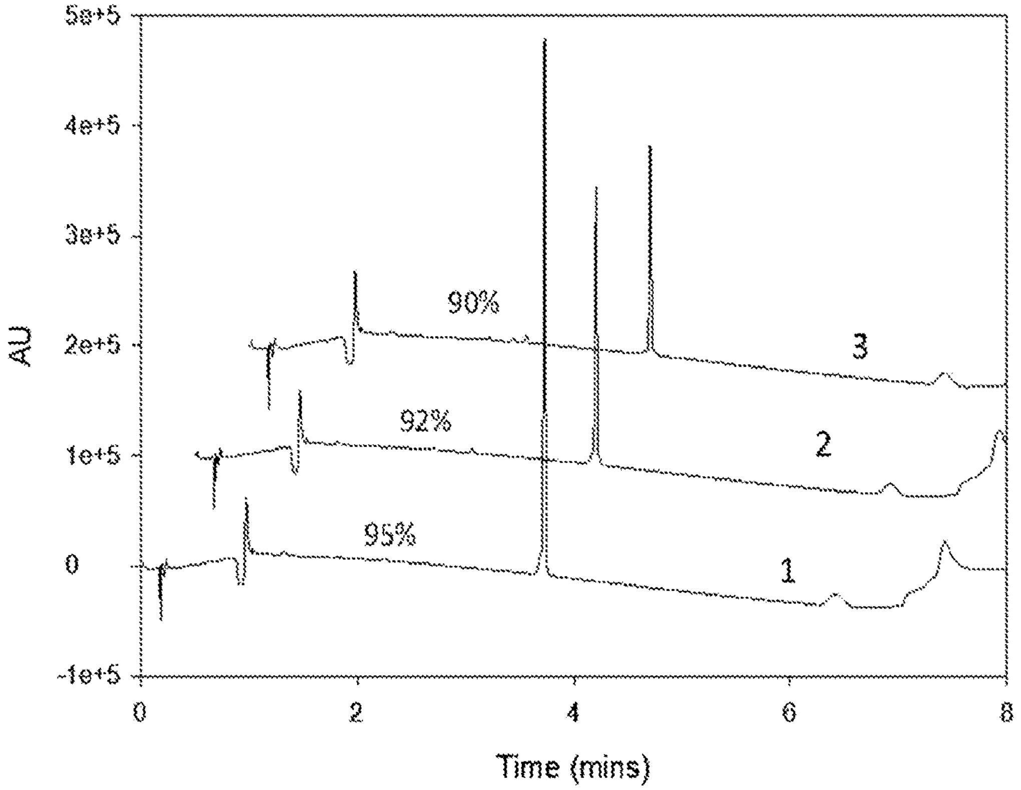

FIG. 7B shows ion-pairing reversed phase liquid chromatograms of collected fractions from the preparative mixed-mode chromatography separations shown in FIG. 7A. Peaks labeled 1, 2, and 3 in FIG. 7A were collected as separate fractions, desalted, and analyzed by ion-pairing reversed phase liquid chromatography using a Waters Xbridge BEH OST C18 column (2.1×50 mm, 1.7 μm) and a 15.7 mM DIEA, 50 mM Hexafluoro-2-propanol mobile phase with elution by an acetonitrile gradient. Purities are provided above each trace. Detection at 260 nm absorbance. For visualization purposes, each of traces 2 and 3 were offset on both the x-axis and y-axis from the previous trace.

Figure 8A:
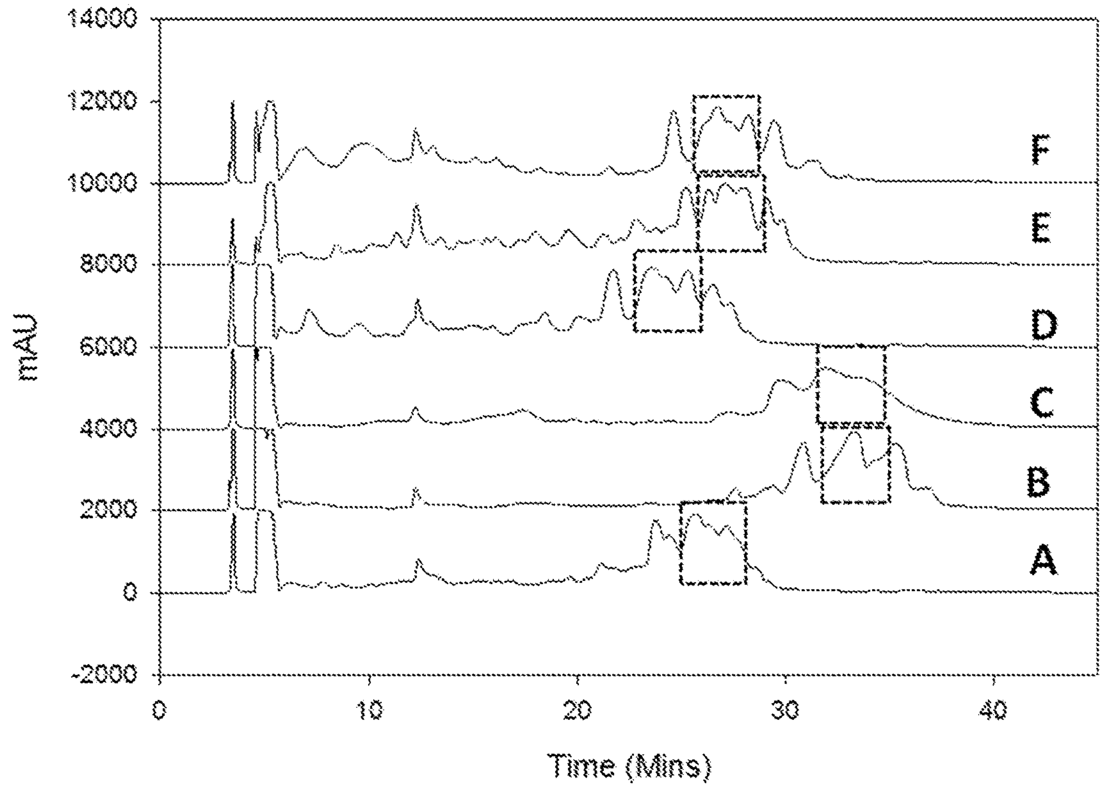

FIG. 8A depicts preparative chromatograms of the separation of various GalNAc-conjugated oligonucleotides using a mixed-mode stationary phase (Scherzo SS-C18 column). A solution comprising each GalNAc-conjugated oligonucleotide was separated on the Scherzo SS-C18 column (10×250 mm, 3 μm) at a flow rate of 5 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 55-80% mobile phase B in 0-40 min, 80% mobile phase B at 40-50 min, 55% mobile phase B at 50.1-70 min. Traces A-F correspond to separations for compound nos. 24-10, 24-13, 24-16, 24-19, 24-22, and 24-25, respectively. Detection was by UV absorbance at 260 nm. Dashed boxes represent fractions that were collected for further analysis.

Figure 8B:
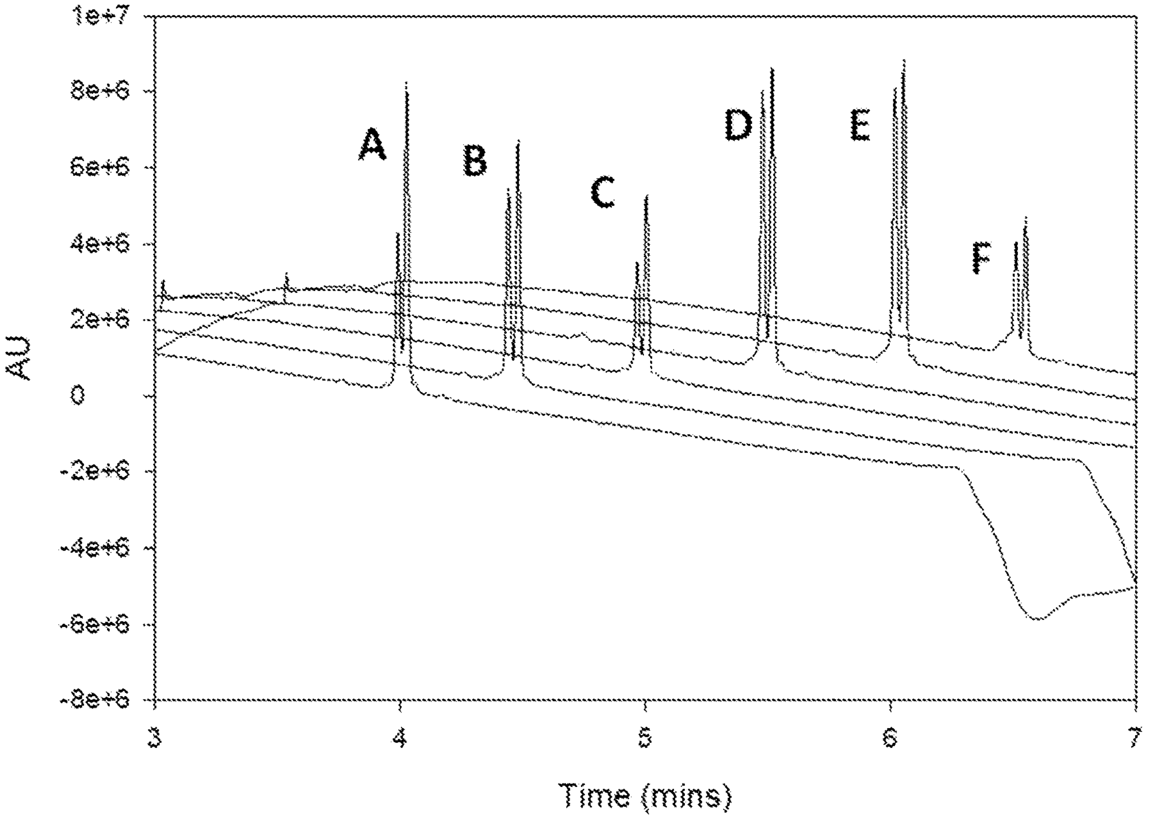

FIG. 8B shows ion-pairing reversed phase liquid chromatograms of collected fractions from the preparative mixed-mode chromatography separations shown in FIG. 8A. Collected fractions (denoted by the dashed boxes in FIG. 8A) comprising each of the GalNAc-conjugated oligonucleotides were combined, de-salted, and analyzed by ion-pairing reversed phase liquid chromatography using a Waters Xbridge BEH OST C18 column (2.1×50 mm, 1.7 μm) and a 15.7 mM DIEA, 50 mM Hexafluoro-2-propanol mobile phase with elution by an acetonitrile gradient. Traces A-F correspond to separations for compound nos. 24-10, 24-13, 24-16, 24-19, 24-22, and 24-25, respectively. Detection at 260 nm absorbance. For visualization purposes, each of traces B-F were offset by 0.5 min (x-axis) and 2e+5 (y-axis) from the previous trace.

Figure 9A:
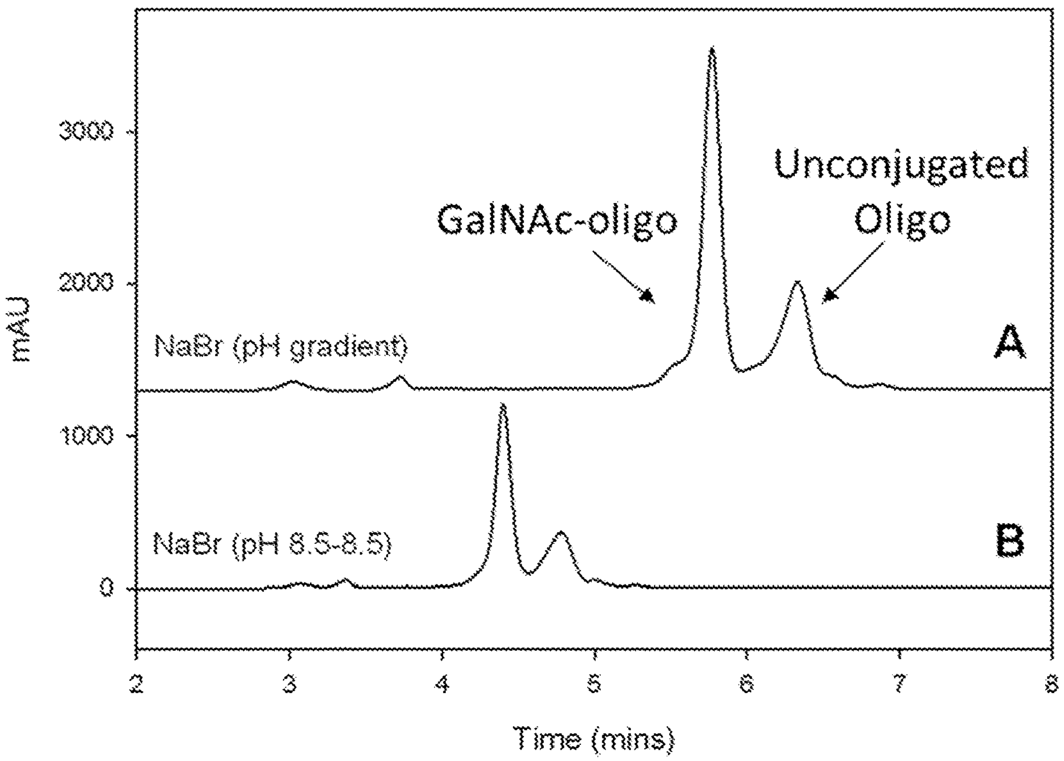

FIG. 9A shows chromatograms of the separation of a GalNAc-conjugated oligonucleotide (compound no. 34-01) using an anion exchange stationary phase (TSK-gel SuperQ-5PW column; 7.5×75 mm, 10 μm) with elution by either a dual pH/salt gradient (Trace A) or a salt gradient (Trace B). For the separation shown in Trace A, a solution comprising the GalNAc-conjugated oligonucleotide was separated on the column at a flow rate of 2 mL/min using a 20 mM $Na_2HPO_4$, 10% acetonitrile (v/v) mobile phase with elution by an increasing gradient of sodium bromide and pH from 8.5 to 11. For the separation shown in Trace B, a solution comprising the GalNAc-conjugated oligonucleotide was separated on the column at a flow rate of 2 mL/min using a 20 mM $Na_2HPO_4$, 10% acetonitrile (v/v) mobile phase, pH 8.5 with elution by an increasing gradient of sodium bromide. Separations were conducted at 40° C. Detection was by UV absorbance at 260 nm.

Figure 9B:
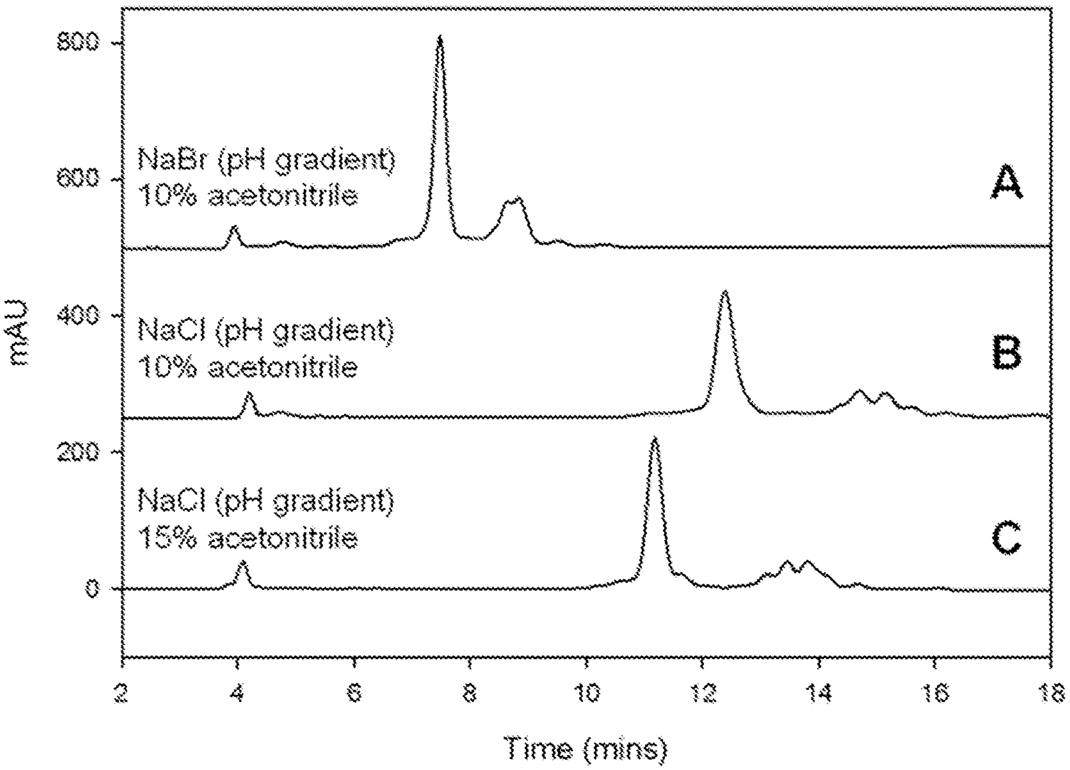

FIG. 9B depicts chromatograms of the separation of a GalNAc-conjugated oligonucleotide (compound no. 34-01) using an anion exchange stationary phase (TSK-gel SuperQ-5PW column; 7.5×75 mm, 10 μm) using different mobile phases. Elution of the oligonucleotide was conducted with an increasing gradient of pH from 8.5 to 11 and increasing concentration of NaBr (Trace A) or NaCl (Traces B and C). The mobile phase for the separation in Trace C had an increased concentration of acetonitrile as compared to the mobile phases for the separations in Traces A and B. Mobile phases were applied to the column at flow rate of 2 mL/min and the separations were performed at 25° C. Detection was by UV absorbance at 260 nm.

Figure 9C:
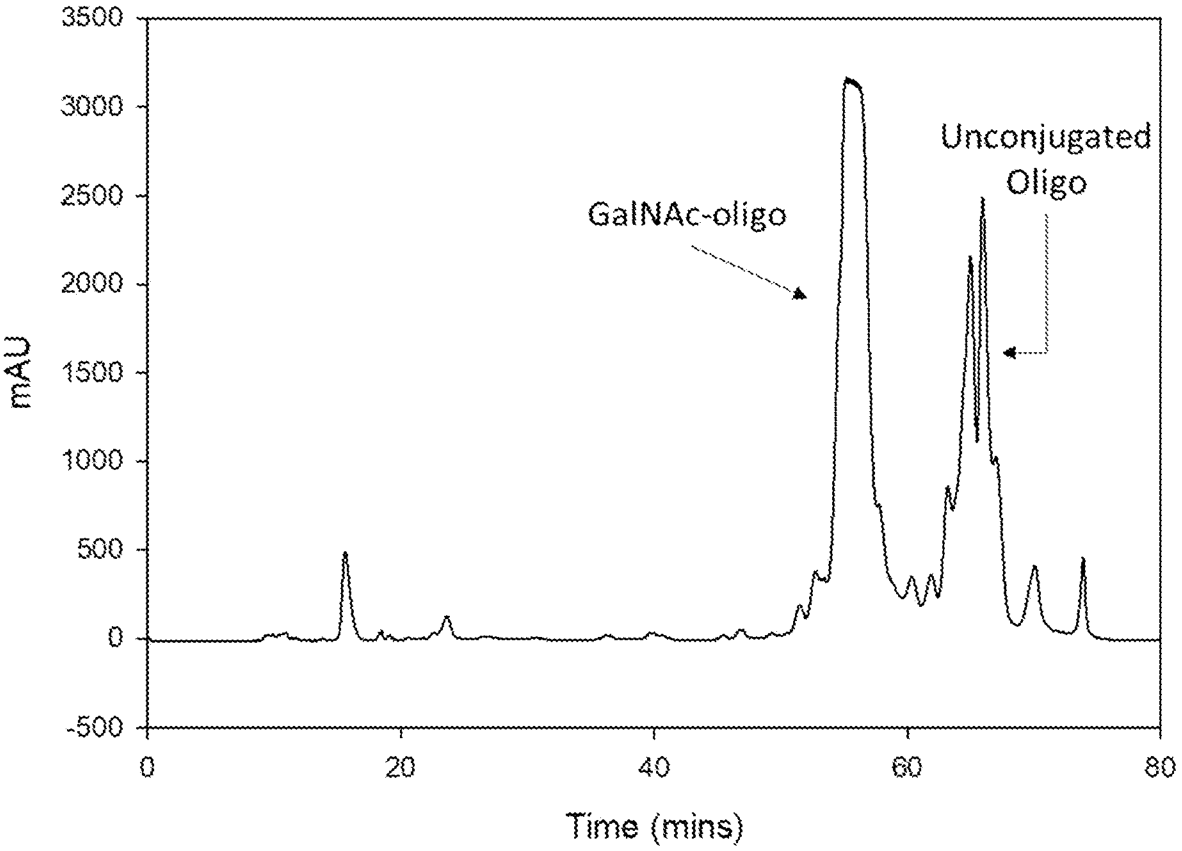

FIG. 9C depicts a preparative chromatogram of the separation of a solution comprising a GalNAc-conjugated oligonucleotide (compound no. 34-01) using an anion exchange stationary phase (two TSK-gel SuperQ-5PW columns linked in series; each column: 21.5×150 mm, 13 μm) with elution by a dual pH/salt gradient. Mobile phase consisted of 20 mM $Na_2HPO_4$, 15% acetonitrile (v/v), pH 8.5 (mobile phase A) and 20 mM $Na_2HPO_4$, 15% acetonitrile (v/v), 1 M NaCl, pH 11 (mobile phase B). Gradient conditions were: 0-30% mobile phase B in 0-7 min, 30-65% mobile phase B at 7-63 min, 65-70% mobile phase B at 63-63.1 min, and 70% mobile phase B at 63.1-66 min. Re-equilibration with mobile phase A (100%) from 66 min-80 min. Mobile phases were applied to the columns at a flow rate of 8.5 mL/min and the separation was performed at ambient temperature. Detection was by UV absorbance at 260 nm.

DETAILED DESCRIPTION

The present invention relates to preparative purification methods for synthetic oligonucleotides, particularly oligonucleotides comprising chemically modified nucleotides or modified internucleotide linkages. The methods of the invention are particularly suitable for separating oligonucleotides conjugated to carbohydrate moieties from unconjugated oligonucleotides and other impurities. In one aspect, the invention is based, in part, on the development of an oligonucleotide purification method using a mixed-mode stationary phase comprising both ion-exchange and hydrophobic ligands and a mobile phase comprising a dual salt/organic solvent gradient that modulates both ion-exchange and hydrophobic interactions to control the separation of the target oligonucleotide from impurities. Accordingly, in certain embodiments, the present invention provides methods for purifying a target oligonucleotide (e.g. a chemically-modified oligonucleotide, a carbohydrate-oligonucleotide conjugate compound) from one or more impurities comprising: contacting a solution comprising the target oligonucleotide and one or more impurities with a mixed-mode matrix; passing a mobile phase through the mixed-mode matrix, wherein the mobile phase has a pH of about 7.0 to about 8.5 and comprises a buffer, an organic solvent, and an elution salt, wherein the concentrations of the elution salt and the organic solvent in the mobile phase increase over time; and collecting elution fractions from the mixed-mode matrix, wherein one or more impurities are eluted in a first set of elution fractions and the target oligonucleotide is eluted in a second set of elution fractions.

In another aspect, the invention relates to methods of purifying an oligonucleotide (e.g. carbohydrate-oligonucleotide conjugate compound) using an anion-exchange stationary phase and elution with a dual pH/salt gradient. Thus, in some embodiments, the present invention provides methods for purifying a target oligonucleotide (e.g. a chemically-modified oligonucleotide, a carbohydrate-oligonucleotide conjugate compound) from one or more impurities comprising: contacting a solution comprising the target oligonucleotide and one or more impurities with an anion-exchange matrix; passing a mobile phase through the anion-exchange matrix, wherein the mobile phase has a pH of at least about 8.5 and comprises a buffer, an organic solvent, and an elution salt, wherein the concentration of the elution salt and the pH of the mobile phase increases over time; and collecting elution fractions from the anion-exchange matrix, wherein the target oligonucleotide is eluted in a first set of elution fractions and one or more impurities are eluted in a second set of elution fractions. These methods afford enhanced selectivity and improved separation between the target oligonucleotide (e.g. carbohydrate-oligonucleotide conjugate compound) and undesired impurities (e.g. unconjugated oligonucleotides) as compared with a conventional anion-exchange chromatography method. The improved anion-exchange chromatography methods of the invention can be used in combination with the mixed-mode chromatography methods of the invention to provide superior purification of oligonucleotides, particularly carbohydrate-oligonucleotide conjugate compounds.

As used herein, an oligonucleotide refers to an oligomer or polymer of nucleotides. The oligonucleotide may comprise ribonucleotides, deoxyribonucleotides, modified nucleotides, or combinations thereof. Oligonucleotides can be a few nucleotides in length up to a couple hundred nucleotides in length, for example, from about 10 nucleotides in length to about 150 nucleotides in length, from about 12 nucleotides in length to about 100 nucleotides in length, from about 15 nucleotides in length to about 120 nucleotides in length, from about 20 nucleotides in length to about 80 nucleotides in length, from about 10 nucleotides in length to about 50 nucleotides in length, from about 14 nucleotides in length to about 60 nucleotides in length, from about 15 nucleotides in length to about 30 nucleotides in length, or from about 18 nucleotides in length to about 26 nucleotides in length. In some embodiments, the oligonucleotide to be purified according to the methods of the invention is about 18, 19, 20, 21, 22, 23, 24, 25, or 26 nucleotides in length. In one embodiment, the oligonucleotide is about 19 nucleotides in length. In another embodiment, the oligonucleotide is about 20 nucleotides in length. In yet another embodiment, the oligonucleotide is about 21 nucleotides in length. In still another embodiment, the oligonucleotide is about 23 nucleotides in length.

The oligonucleotide to be purified according to the methods of the invention may be a naturally-occurring oligonucleotide isolated from a cell or organism or it may be a synthetic oligonucleotide produced by chemical synthetic methods or in vitro enzymatic methods. In some embodiments, the oligonucleotide can be a short hairpin RNA (shRNA), a precursor miRNA (pre-miRNA), an anti-miRNA oligonucleotide (e.g. antagomir and antimiR), or an antisense oligonucleotide. In other embodiments, the oligonucleotide can be one of the component strands of a double-stranded RNA molecule or RNA interference agent, such as a small interfering RNA (siRNA), a microRNA (miRNA), or a miRNA mimetic.

In certain embodiments, the oligonucleotide to be purified according to the methods of the invention is a therapeutic oligonucleotide designed to target a gene or RNA molecule associated with a disease or disorder. For instance, in one embodiment, the oligonucleotide is an antisense oligonucleotide that comprises a sequence complementary to a region of a target gene or mRNA sequence. A first sequence is "complementary" to a second sequence if an oligonucleotide comprising the first sequence can hybridize to an oligonucleotide comprising the second sequence to form a duplex region under certain conditions. "Hybridize" or "hybridization" refers to the pairing of complementary oligonucleotides, typically via hydrogen bonding (e.g. Watson-Crick, Hoogsteen or reverse Hoogsteen hydrogen bonding) between complementary bases in the two oligonucleotides. A first sequence is considered to be fully complementary (100% complementary) to a second sequence if an oligonucleotide comprising the first sequence base pairs with an oligonucleotide comprising the second sequence over the entire length of one or both nucleotide sequences without any mismatches.

In some embodiments, the oligonucleotide to be purified according to the methods of the invention is an antisense strand of an siRNA or other type of double-stranded RNA interference agent, wherein the antisense strand comprises a sequence that is complementary to a region of a target gene or mRNA sequence. In another embodiment, the oligonucleotide is a sense strand of an siRNA or other type of double-stranded RNA interference agent, wherein the sense strand comprises a sequence identical to a region of a target gene or mRNA sequence. The strand of an siRNA or other type of double-stranded RNA interference agent comprising a region having a sequence that is complementary to a target sequence (e.g. target mRNA) is referred to as the "antisense strand." The "sense strand" refers to the strand that includes a region that is complementary to a region of the antisense strand.

The oligonucleotide to be purified according to the methods of the invention may comprise one or more modified nucleotides. A "modified nucleotide" refers to a nucleotide that has one or more chemical modifications to the nucleoside, nucleobase, pentose ring, or phosphate group. Such modified nucleotides can include, but are not limited to, nucleotides with 2' sugar modifications (2'-O-methyl, 2'-methoxyethyl, 2'-fluoro, etc.), abasic nucleotides, inverted nucleotides (3'-3' linked nucleotides), phosphorothioate linked nucleotides, nucleotides with bicyclic sugar modifications (e.g. LNA, ENA), and nucleotides comprising base analogs (e.g. universal bases, 5-methylcytosine, pseudouracil, etc.).

In certain embodiments, the modified nucleotides have a modification of the ribose sugar. These sugar modifications can include modifications at the 2' and/or 5' position of the pentose ring as well as bicyclic sugar modifications. A 2'-modified nucleotide refers to a nucleotide having a pentose ring with a substituent at the 2' position other than H or OH. Such 2'-modifications include, but are not limited to, 2'-O-alkyl (e.g. O—$C_1$-$C_{10}$ or O—$C_1$-$C_{10}$ substituted alkyl), 2'-O-allyl (O—$CH_2CH$═$CH_2$), 2'-C-allyl, 2'-fluoro, 2'-O-methyl ($OCH_3$), 2'-O-methoxyethyl (O—$(CH_2)_2OCH_3$), 2'-$OCF_3$, 2'-O$(CH_2)_2SCH_3$, 2'-O-aminoalkyl, 2'-amino (e.g. $NH_2$), 2'-O-ethylamine, and 2'-azido. Modifications at the 5' position of the pentose ring include, but are not limited to, 5'-methyl (R or S); 5'-vinyl, and 5'-methoxy. A "bicyclic sugar modification" refers to a modification of the pentose ring where a bridge connects two atoms of the ring to form a second ring resulting in a bicyclic sugar structure. In some embodiments the bicyclic sugar modification comprises a bridge between the 4' and 2' carbons of the pentose ring. Nucleotides comprising a sugar moiety with a bicyclic sugar modification are referred to herein as bicyclic nucleic acids or BNAs. Exemplary bicyclic sugar modifications include, but are not limited to, α-L-Methyleneoxy (4'-$CH_2$—O-2') bicyclic nucleic acid (BNA); β-D-Methyleneoxy (4'-$CH_2$—O-2') BNA (also referred to as a locked nucleic acid or LNA); Ethyleneoxy (4'-$(CH_2)_2$—O-2') BNA; Aminooxy (4'-$CH_2$—O—N(R)-2') BNA; Oxyamino (4'-$CH_2$—N(R)—O-2') BNA; Methyl(methyleneoxy) (4'-CH($CH_3$)—O-2') BNA (also referred to as constrained ethyl or cEt); methylene-thio (4'-$CH_2$—S-2') BNA; methylene-amino (4'-$CH_2$—N(R)-2') BNA; methyl carbocyclic (4'-$CH_2$—CH($CH_3$)-2') BNA; propylene carbocyclic (4'-$(CH_2)_3$-2') BNA; and Methoxy (ethyleneoxy) (4'-CH($CH_2$OMe)-O-2') BNA (also referred to as constrained MOE or cMOE). These and other sugar-modified nucleotides that can be incorporated into oligonucleotides to be purified according to the methods of the invention are described in U.S. Pat. No. 9,181,551, U.S. Patent Publication No. 2016/0122761, and Deleavey and Damha, Chemistry and Biology, Vol. 19: 937-954, 2012, all of which are hereby incorporated by reference in their entireties.

In some embodiments, the oligonucleotides to be purified according to the methods of the invention comprise one or more 2'-fluoro modified nucleotides, 2'-O-methyl modified nucleotides, 2'-O-methoxyethyl modified nucleotides, 2'-O-allyl modified nucleotides, bicyclic nucleic acids (BNAs), or combinations thereof. In certain embodiments, the oligonucleotides to be purified according to the methods of the invention comprise one or more 2'-fluoro modified nucleotides, 2'-O-methyl modified nucleotides, 2'-O-methoxyethyl modified nucleotides, or combinations thereof. In one particular embodiment, the oligonucleotides to be purified according to the methods of the invention comprise one or more 2'-fluoro modified nucleotides, 2'-O-methyl modified nucleotides or combinations thereof.

The oligonucleotides that can be purified according to the methods of the invention may also comprise one or more modified internucleotide linkages. As used herein, the term "modified internucleotide linkage" refers to an internucleotide linkage other than the natural 3' to 5' phosphodiester linkage. In some embodiments, the modified internucleotide linkage is a phosphorous-containing internucleotide linkage, such as a phosphotriester, aminoalkylphosphotriester, an alkylphosphonate (e.g. methylphosphonate, 3'-alkylene phosphonate), a phosphinate, a phosphoramidate (e.g. 3'-amino phosphoramidate and aminoalkylphosphoramidate), a phosphorothioate (P═S), a phosphorodithioate, a thionophosphoramidate, a thionoalkylphosphonate, a thionoalkylphosphotriester, and a boranophosphate. In one embodiment, a modified internucleotide linkage is a 2' to 5' phosphodiester linkage. In other embodiments, the modified internucleotide linkage is a non-phosphorous-containing internucleotide linkage and thus can be referred to as a modified internucleoside linkage. Such non-phosphorous-containing linkages include, but are not limited to, morpholino linkages (formed in part from the sugar portion of a nucleoside); siloxane linkages (—O—$Si(H)_2$—O—); sulfide, sulfoxide and sulfone linkages; formacetyl and thioformacetyl linkages; alkene containing backbones; sulfamate backbones; methylenemethylimino (—$CH_2$—N($CH_3$)—O—$CH_2$) and methylenehydrazino linkages; sulfonate and sulfonamide linkages; amide linkages; and others having mixed N, O, S and $CH_2$ component parts. In one embodiment, the modified internucleoside linkage is a peptide-based linkage (e.g. aminoethylglycine) to create a peptide nucleic acid or PNA, such as those described in U.S. Pat. Nos. 5,539,082; 5,714,331; and 5,719,262. Other suitable modified internucleotide and internucleoside linkages that may be incorporated into the oligonucleotides to be purified according to the methods of the invention are described in U.S. Pat. Nos. 6,693,187, 9,181,551, U.S. Patent Publication No. 2016/0122761, and Deleavey and Damha, Chemistry and Biology, Vol. 19: 937-954, 2012, all of which are hereby incorporated by reference in their entireties.

In certain embodiments, the oligonucleotides to be purified according to the methods of the invention comprise one or more phosphorothioate internucleotide linkages. The oligonucleotides may comprise 1, 2, 3, 4, 5, 6, 7, 8, or more phosphorothioate internucleotide linkages. In some embodiments, all of the internucleotide linkages in the oligonucleotides are phosphorothioate internucleotide linkages. In other embodiments, the oligonucleotides can comprise one or more phosphorothioate internucleotide linkages at the 3'-end, the 5'-end, or both the 3'- and 5'-ends. For instance, in certain embodiments, the oligonucleotides comprise about 1 to about 6 or more (e.g., about 1, 2, 3, 4, 5, 6 or more) consecutive phosphorothioate internucleotide linkages at the 3'-end. In other embodiments, the oligonucleotides comprise about 1 to about 6 or more (e.g., about 1, 2, 3, 4, 5, 6 or more) consecutive phosphorothioate internucleotide linkages at the 5'-end. Incorporation of a phosphorothioate internucleotide linkage introduces an additional chiral center at phosphorous in the oligonucleotide and therefore creates a diastereomer pair (Rp and Sp) at each phosphorothioate internucleotide linkage. Diastereomers or diastereoisomers are different configurations of a compound that have the same molecular formula and sequence of bonded atoms but differ in the three-dimensional orientations of their atoms in space. Unlike enantiomers, diastereomers are not mirror-images of each other. Such phosphorothioate diastereomers have the same length, sequence, charge, and mass and are difficult to separate by most chromatographic approaches. See, e.g., Thayer et al., Journal of Chromatography A, Vol. 1218: 802-808, 2011. As described in more detail herein, the mixed-mode chromatography methods of the invention provide for the separation of sets of phosphorothioate diastereomers of the oligonucleotides on a preparative scale.

In some embodiments, the oligonucleotides to be purified according to the methods of the invention are conjugated or covalently linked to a ligand that targets the oligonucleotide to a specific tissue or cell type. For instance, in one embodiment, the oligonucleotide is covalently linked to a ligand that targets delivery of the oligonucleotide to liver cells (e.g. hepatocytes). One such ligand comprises a carbohydrate that binds to the asialoglycoprotein receptor (ASGR) or component thereof (e.g. ASGR1, ASGR2) that is expressed on the surface of hepatocytes. Thus, in certain embodiments, the oligonucleotides to be purified according to the methods of the invention are carbohydrate-oligonucleotide conjugate compounds. A carbohydrate-oligonucleotide conjugate compound refers to an oligonucleotide that is covalently linked, either directly or indirectly via a linker moiety, to a carbohydrate. A carbohydrate refers to a compound made up of one or more monosaccharide units having at least 6 carbon atoms (which can be linear, branched or cyclic) with an oxygen, nitrogen or sulfur atom bonded to each carbon atom. Carbohydrates include, but are not limited to, the sugars (e.g., monosaccharides, disaccharides, trisaccharides, tetrasaccharides, and oligosaccharides containing from about 4, 5, 6, 7, 8, or 9 monosaccharide units), and polysaccharides, such as starches, glycogen, cellulose and polysaccharide gums. In some embodiments, the carbohydrate incorporated into the carbohydrate-oligonucleotide conjugate compound comprises a monosaccharide selected from a pentose, hexose, or heptose and di- and tri-saccharides including such monosaccharide units. In other embodiments, the carbohydrate incorporated into the carbohydrate-oligonucleotide conjugate compound comprises an amino sugar, such as galactosamine, glucosamine, N-acetylgalactosamine, and N-acetylglucosamine.

In some embodiments, the carbohydrate incorporated into the carbohydrate-oligonucleotide conjugate compound comprises one or more hexose or hexosamine units. The hexose may be selected from glucose, galactose, mannose, fucose, or fructose. The hexosamine may be selected from fructosamine, galactosamine, glucosamine, or mannosamine. In certain embodiments, the carbohydrate incorporated into the carbohydrate-oligonucleotide conjugate compound comprises one or more glucose, galactose, galactosamine, or glucosamine units. In one embodiment, the carbohydrate incorporated into the carbohydrate-oligonucleotide conjugate compound comprises one or more glucose, glucosamine, or N-acetylglucosamine units. In another embodiment, the carbohydrate incorporated into the carbohydrate-oligonucleotide conjugate compound comprises one or more galactose, galactosamine, or N-acetyl-galactosamine units. In particular embodiments, the carbohydrate incorporated into the carbohydrate-oligonucleotide conjugate compound comprises one or more N-acetyl-galactosamine (GalNAc) units. Examples of GalNAc- or galactose-containing ligands that can be covalently linked to an oligonucleotide to create a carbohydrate-oligonucleotide conjugate compound to be purified according to the methods of the invention are described in U.S. Pat. Nos. 7,491,805; 8,106,022; and 8,877,917; U.S. Patent Publication Nos. 20030130186 and 20170253875; and WIPO Publication Nos. WO 2013166155, WO 2014179620, and WO 2018039647, all of which are hereby incorporated by reference in their entireties.

In certain embodiments, the carbohydrate incorporated into the carbohydrate-oligonucleotide conjugate compound is a multivalent carbohydrate moiety. As used herein, a multivalent carbohydrate moiety refers to a moiety comprising two or more carbohydrate units capable of independently binding or interacting with other molecules. For example, a multivalent carbohydrate moiety comprises two or more binding domains comprised of carbohydrates that can bind to two or more different molecules or two or more different sites on the same molecule. The valency of the carbohydrate moiety denotes the number of individual binding domains within the carbohydrate moiety. For instance, the terms monovalent, bivalent, trivalent, and tetravalent with reference to the carbohydrate moiety refer to carbohydrate moieties with one, two, three, and four binding domains, respectively. The multivalent carbohydrate moiety may comprise a multivalent lactose moiety, a multivalent galactose moiety, a multivalent glucose moiety, a multivalent N-acetyl-galactosamine moiety, a multivalent N-acetyl-glucosamine moiety, a multivalent mannose moiety, or a multivalent fucose moiety. In some embodiments, the carbohydrate incorporated into the carbohydrate-oligonucleotide conjugate compound comprises a multivalent galactose moiety. In other embodiments, the carbohydrate incorporated into the carbohydrate-oligonucleotide conjugate compound comprises a multivalent N-acetyl-galactosamine moiety. In these and other embodiments, the multivalent carbohydrate moiety is bivalent, trivalent, or tetravalent. In such embodiments, the multivalent carbohydrate moiety can be bi-antennary or tri-antennary. In one particular embodiment, the multivalent N-acetyl-galactosamine moiety is trivalent or tetravalent. In another particular embodiment, the multivalent galactose moiety is trivalent or tetravalent. Examples of such trivalent and tetravalent galactose and GalNAc-containing carbohydrate moieties for incorporation into carbohydrate-oligonucleotide conjugate compounds have been described previously. See, e.g., U.S. Pat. Nos. 7,491,805 and 8,106,022; U.S. Patent Publication No. 20170253875; and WIPO Publication Nos. WO 2013166155, WO 2014179620, and WO 2018039647. In certain embodiments, the carbohydrate incorporated into the carbohydrate-oligonucleotide conjugate compound comprises a multivalent N-acetyl-galactosamine moiety having the structure shown in Structure 1 in Example 1.

In a carbohydrate-oligonucleotide conjugate compound, the carbohydrate can be attached or conjugated to the oligonucleotide directly or indirectly via a linker moiety. The carbohydrate can be attached to nucleobases, pentose sugars, or internucleotide linkages of the oligonucleotide. Conjugation or attachment to purine nucleobases or derivatives thereof can occur at any position including, endocyclic and exocyclic atoms. In certain embodiments, the 2-, 6-, 7-, or 8-positions of a purine nucleobase are attached to a carbohydrate. Conjugation or attachment to pyrimidine nucleobases or derivatives thereof can also occur at any position. In some embodiments, the 2-, 5-, and 6-positions of a pyrimidine nucleobase can be attached to a carbohydrate. Conjugation or attachment to the pentose sugars of nucleotides can occur at any carbon atom. Exemplary carbon atoms of a pentose sugar that can be attached to a carbohydrate include the 2', 3', and 5' carbon atoms. The 1' position can also be attached to a carbohydrate where the nucleobase is omitted, such as in an abasic nucleotide. Internucleotide linkages can also support carbohydrate attachments. For phosphorus-containing linkages (e.g., phosphodiester, phosphorothioate, phosphorodithiotate, phosphoroamidate, and the like), the carbohydrate can be attached directly to the phosphorus atom or to an O, N, or S atom bound to the phosphorus atom. For amine- or amide-containing internucleoside linkages (e.g., PNA), the carbohydrate can be attached to the nitrogen atom of the amine or amide or to an adjacent carbon atom.

In certain embodiments, in a carbohydrate-oligonucleotide conjugate compound the carbohydrate is attached to the 3' or 5' end of the oligonucleotide. In one embodiment, the carbohydrate is covalently attached to the 5' end of the oligonucleotide. In such embodiments, the carbohydrate is attached to the 5'-terminal nucleotide of the oligonucleotide. In these and other embodiments, the carbohydrate is attached at the 5'-position of the 5'-terminal nucleotide of the oligonucleotide. In other embodiments, the carbohydrate is covalently attached to the 3' end of the oligonucleotide. For example, in some embodiments, the carbohydrate is attached to the 3'-terminal nucleotide of the oligonucleotide. In certain such embodiments, the carbohydrate is attached at the 3'-position of the 3'-terminal nucleotide of the oligonucleotide. In alternative embodiments, the carbohydrate is attached near the 3' end of the oligonucleotide, but before one or more terminal nucleotides (i.e. before 1, 2, 3, or 4 terminal nucleotides). In some embodiments, the carbohydrate is attached at the 2'-position of the pentose sugar of the 3'-terminal nucleotide of the oligonucleotide. In other embodiments, the carbohydrate is attached at the 2'-position of the pentose sugar of the 5'-terminal nucleotide of the oligonucleotide.

In some carbohydrate-oligonucleotide conjugate compounds to be purified according to the methods of the invention, the carbohydrate is attached to the oligonucleotide via a linker moiety. A linker moiety is an atom or group of atoms that covalently joins a carbohydrate to the oligonucleotide. The linker moiety may be from about 1 to about 30 atoms in length, from about 2 to about 28 atoms in length, from about 3 to about 26 atoms in length, from about 4 to about 24 atoms in length, from about 6 to about 20 atoms in length, from about 7 to about 20 atoms in length, from about 8 to about 20 atoms in length, from about 8 to about 18 atoms in length, from about 10 to about 18 atoms in length, and from about 12 to about 18 atoms in length. In some embodiments, the linker moiety may comprise a bifunctional linking moiety, which generally comprises an alkyl moiety with two functional groups. One of the functional groups is selected to bind to the oligonucleotide and the other is selected to bind essentially any selected group, such as a carbohydrate as described herein. In certain embodiments, the linker moiety comprises a chain structure or an oligomer of repeating units, such as ethylene glycol or amino acid units. Examples of functional groups that are typically employed in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Linker moieties that may be used to attach a carbohydrate to the oligonucleotide include, but are not limited to, pyrrolidine, 8-amino-3,6-dioxaoctanoic acid, succinimidyl 4-(N-maleimidomethyl)cyclohexane-1-carboxylate, 6-aminohexanoic acid, substituted $C_1$-$C_{10}$ alkyl, substituted or unsubstituted $C_2$-$C_{10}$ alkenyl or substituted or unsubstituted $C_2$-$C_{10}$ alkynyl. Preferred substituent groups for such linkers include, but are not limited to, hydroxyl, amino, alkoxy, carboxy, benzyl, phenyl, nitro, thiol, thioalkoxy, halogen, alkyl, aryl, alkenyl and alkynyl.

The oligonucleotides to be purified according to the methods of the invention can readily be made using techniques known in the art, for example, using conventional nucleic acid solid phase synthesis. The oligonucleotides can be assembled on a suitable nucleic acid synthesizer utilizing standard nucleotide or nucleoside precursors (e.g. phosphoramidites). Automated nucleic acid synthesizers are sold commercially by several vendors, including DNA/RNA synthesizers from Applied Biosystems (Foster City, CA), MerMade synthesizers from BioAutomation (Irving, TX), and OligoPilot synthesizers from GE Healthcare Life Sciences (Pittsburgh, PA). The 2' silyl protecting group can be used in conjunction with acid labile dimethoxytrityl (DMT) at the 5' position of ribonucleosides to synthesize oligonucleotides via phosphoramidite chemistry. Final deprotection conditions are known not to significantly degrade RNA products. All syntheses can be conducted in any automated or manual synthesizer on large, medium, or small scale. The syntheses may also be carried out in multiple well plates, columns, or glass slides. The 2'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion sources are tetrabutylammonium fluoride or aminohydrofluorides (e.g., combining aqueous HF with triethylamine in a dipolar aprotic solvent, e.g., dimethylformamide). The various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing oligonucleotides are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

As can be appreciated by the skilled artisan, further methods of synthesizing the oligonucleotides will be evident to those of ordinary skill in the art. For instance, the oligonucleotides can be synthesized using enzymes in in vitro systems, such as in the methods described in Jensen and Davis, Biochemistry, Vol. 57: 1821-1832, 2018. Naturally-occurring oligonucleotides can be isolated from cells or organisms using conventional methods. Custom synthesis of oligonucleotides is also available from several commercial vendors, including Dharmacon, Inc. (Lafayette, CO), AxoLabs GmbH (Kulmbach, Germany), and Ambion, Inc. (Foster City, CA). Methods of coupling or conjugating carbohydrates to oligonucleotides are also known to those of skill in the art and can include generation of a phosphoramidite of the carbohydrate ligand that can be incorporated into the routine oligonucleotide synthetic reaction, condensation reactions, ester coupling, and other coupling reactions, the specifics of which are dictated by the type of linker moiety employed.

The methods of the invention can be used to purify or separate oligonucleotides, particularly carbohydrate-oligonucleotide conjugate compounds from one or more impurities in a solution. "Purify" or "purification" refers to a process that reduces the amounts of substances that are different than the target molecule (e.g. oligonucleotide or carbohydrate-oligonucleotide conjugate compound) and are desirably excluded from the final composition or preparation. The term "impurity" refers to a substance having a different structure than the target molecule and the term can include a single undesired substance or a combination of several undesired substances. Impurities can include materials or reagents used in the methods to produce the oligonucleotides or carbohydrate-oligonucleotide conjugate compounds as well as fragments or other undesirable derivatives or forms of the oligonucleotides. In certain embodiments, the impurities comprise one or more oligonucleotides having a shorter length than the target oligonucleotide. In these and other embodiments, the impurities comprise one or more failure sequences. Failure sequences can be generated during the synthesis of the target oligonucleotide and arise from the failure of coupling reactions during the stepwise addition of a nucleotide monomer to the oligonucleotide chain. The product of an oligonucleotide synthetic reaction is often a heterogeneous mixture of oligonucleotides of varying lengths comprising the target oligonucleotide and various failure sequences having lengths shorter than the target oligonucleotide (i.e. truncated versions of the target oligonucleotide). In some embodiments, the impurities comprise unconjugated oligonucleotides—i.e. oligonucleotides which lack the covalent attachment of the carbohydrate. The presence of unconjugated oligonucleotides may arise from incomplete coupling reactions to attach the carbohydrate to the oligonucleotide or loss of the carbohydrate component from the conjugate compound as a result of process or storage conditions. In other embodiments, the impurities comprise one or more process-related impurities. Depending on the synthetic method to produce the oligonucleotide and/or carbohydrate-oligonucleotide conjugate compound, such process-related impurities can include, but are not limited to, nucleotide monomers, protecting groups, phosphoramidite precursors, hydrolysis products of carbohydrates, salts, enzymes, and endotoxins.

A solution from which an oligonucleotide or carbohydrate-oligonucleotide conjugate compound can be purified can be any solution containing the oligonucleotide or carbohydrate-oligonucleotide conjugate compound and one or more impurities or contaminants, the presence of which is not desired. A solution comprising the oligonucleotide or carbohydrate-oligonucleotide conjugate compound and one or more impurities can include mixtures resulting from synthetic methods to produce the oligonucleotide or conjugate compound. For example, in one embodiment the solution comprising the oligonucleotide or carbohydrate-oligonucleotide conjugate compound and one or more impurities is a reaction mixture from a chemical synthetic method to produce the oligonucleotide or conjugate compound, such as a synthetic reaction mixture obtained from an automated synthesizer. In such an embodiment, the solution may also comprise failure sequences. In another embodiment, the solution comprising the oligonucleotide or carbohydrate-oligonucleotide conjugate compound and one or more impurities is a mixture from an in vitro enzymatic synthetic reaction (e.g. polymerase chain reaction (PCR)). In yet another embodiment, the solution comprising the carbohydrate-oligonucleotide conjugate compound and one or more impurities is a reaction mixture from a coupling reaction to attach the carbohydrate to the oligonucleotide. In still another embodiment, the solution comprising the oligonucleotide or carbohydrate-oligonucleotide conjugate compound and one or more impurities is a solution or mixture from another purification operation, such as the eluate from a chromatographic separation. For instance, in some embodiments, the solution comprising the oligonucleotide or carbohydrate-oligonucleotide conjugate compound and one or more impurities is an eluate from an anion-exchange chromatography matrix. In other embodiments, the solution comprising the oligonucleotide or carbohydrate-oligonucleotide conjugate compound and one or more impurities is an eluate from a mixed-mode chromatography matrix.

In certain embodiments, the present invention provides methods for purifying an oligonucleotide, particularly a carbohydrate-oligonucleotide conjugate compound, from one or more impurities by contacting a solution comprising the oligonucleotide or carbohydrate-oligonucleotide conjugate compound and one or more impurities with a mixed-mode matrix and eluting the oligonucleotide or carbohydrate-oligonucleotide conjugate compound from the mixed-mode matrix with a mobile phase comprising a buffer and increasing concentrations of an elution salt and an organic solvent (e.g. a dual salt/organic solvent gradient). In one embodiment, the method comprises contacting a solution comprising the oligonucleotide or carbohydrate-oligonucleotide conjugate compound and one or more impurities with a mixed-mode matrix; passing a mobile phase through the mixed-mode matrix, wherein the mobile phase has a pH of about 7.0 to about 8.5 and comprises a buffer, an organic solvent, and an elution salt, wherein the concentrations of the elution salt and organic solvent increase over time; and collecting elution fractions from the mixed-mode matrix, wherein one or more impurities are eluted in a first set of elution fractions and the oligonucleotide or carbohydrate-oligonucleotide conjugate compound is eluted in a second set of elution fractions, thereby separating the oligonucleotide or carbohydrate-oligonucleotide conjugate compound from the impurities.

Thus, in some embodiments, the methods of the invention entail contacting an oligonucleotide or carbohydrate-oligonucleotide conjugate compound with a mixed-mode matrix. A mixed-mode matrix refers to a material comprising ligands having functional groups that interact with solutes through more than one mode or mechanism of interaction. For instance, a mixed-mode matrix may comprise ligands having a first set of functional groups that interact with solutes based on charge-charge interactions and a second set of functional groups that interact with solutes based on hydrophobic or hydrophilic interactions. A mixed-mode matrix may be created by various approaches including, but not limited to: (i) combining two or more types of particles each having ligands with different functional groups (e.g. ion-exchange ligands and hydrophobic ligands) into a single column, (ii) immobilizing different sets of ligands having different functional groups onto a support, and (iii) attaching a ligand having two or more different functional groups onto a support. The supports to which the ligands having the different functional groups are attached are generally comprised of silica gel or cross-linked polymers, such as polymethacrylate, polyvinylpyrrolidone-divinylbenzene, and polystyrene-divinylbenzene, although other materials may be used as well.

In some embodiments, the pore size of the mixed-mode matrix is less than about 20 nm. For instance, the pore size of the mixed-mode matrix can be from about 5 nm to about 18 nm, from about 8 nm to about 15 nm, from about 10 nm to about 16 nm, from about 7 nm to about 14 nm, or from about 11 nm to about 14 nm. In certain embodiments, the mixed-mode matrix has a pore size from about 8 nm to about 15 nm. In some embodiments, the mixed-mode matrix has a pore size from about 11 nm to about 14 nm. In one particular embodiment, the mixed-mode matrix has a pore size of about 13 nm. In another particular embodiment, the mixed-mode matrix has a pore size of about 10 nm.

The mixed-mode matrix used in the methods of the invention generally will comprise ligands having positively-charged functional groups, negatively-charged functional groups, and hydrophobic functional groups. The positively-charged functional groups can be primary amines, secondary amines, tertiary amines, or quaternary amines. The negatively-charged functional groups can be sulfonyl groups (e.g. sulfoethyl, sulfopropyl, sulfonate), carboxyl groups (e.g. carboxymethyl, carboxylate) or phosphate groups (e.g. phosphonate). The hydrophobic functional groups can be alkyl groups (e.g. isopropyl, propyl, t-butyl, butyl, and C8 to C18 alkyl chains) or aryl groups (e.g. phenyl group).

In certain embodiments, the mixed-mode matrix comprises strong ion exchange ligands, which refer to ligands comprising strong ion exchange groups. Strong ion exchange groups show no variation in ion exchange capacity with changes in pH and are fully charged within a wide pH range (e.g. at pH values between 2 and 13). Strong anion exchange ligands may comprise quaternary amines, such as quaternary aminoethyl, quaternary ammonium, and quaternary aminomethyl. Strong cation exchange ligands may comprise sulfonyl functional groups, such as sulfoethyl, sulfopropyl, and sulfonates.

In other embodiments, the mixed-mode matrix comprises weak ion exchange ligands, which refer to ligands comprising weak ion exchange groups. Weak anion exchange groups are ionized only over a limited pH range. Examples of weak anion exchange groups include, but are not limited to, polyethylenimine, diethylaminomethyl, diethylaminoethyl, dimethylaminopropyl, ethylendiamino, and polyallylamine. Exemplary weak cation exchange groups include, but are not limited to phosphate groups, such as phosphonates, and carboxyl groups, such as carboxymethyl and carboxylates.

In some embodiments, the mixed-mode matrix comprises a high density of ion exchange ligands, particularly, strong ion exchange ligands, such that the mixed-mode matrix has a high ion exchange capacity. For instance, the mixed-mode matrix may have a density of strong ion exchange ligands of greater than about 100 μmol/gram, greater than about 150 μmol/gram, greater than about 200 μmol/gram, greater than about 250 μmol/gram, greater than about 300 μmol/gram, greater than about 350 μmol/gram, greater than about 400 μmol/gram, or greater than about 450 μmol/gram.

Ion exchange capacity can be expressed as microequivalents (μeq) per mL of matrix. In certain embodiments, the mixed-mode matrix has an anion-exchange capacity of at least 4 μeq/mL, at least 5 μeq/mL, at least 6 μeq/mL, at least 7 μeq/mL, or at least 8 μeq/mL of matrix. In some embodiments, the mixed-mode matrix has an anion-exchange capacity of about 6 μeq/mL to about 10 μeq/mL of matrix. In other embodiments, the mixed-mode matrix has an anion-exchange capacity of about 7 μeq/mL to about 9 μeq/mL of matrix. In these and other embodiments, the mixed-mode matrix has a cation-exchange capacity of at least of at least 8 μeq/mL, at least 10 μeq/mL, at least 12 μeq/mL, at least 14 μeq/mL, at least 16 μeq/mL, at least 18 eq/mL, or at least 20 eq/mL of matrix. In some embodiments, the mixed-mode matrix has a cation-exchange capacity of about 14 μeq/mL to about 24 μeq/mL of matrix. In other embodiments, the mixed-mode matrix has a cation-exchange capacity of about 18 μeq/mL to about 22 μeq/mL of matrix. In one particular embodiment, the mixed-mode matrix has an anion-exchange capacity of about 7 μeq/mL to about 9 μeq/mL of matrix and a cation-exchange capacity of about 18 μeq/mL to about 22 μeq/mL of matrix. Ion exchange capacity of various matrices can be measured according to methods known to those of skill in the art, such as the methods described in Kazarian et al., Anal Chim Acta, Vol. 803:143-153, 2013 and Kazarian et al., Chromatographia, Vol. 78:179-187, 2015.

In addition to ion exchange ligands, the mixed-mode matrix employed in the methods of the invention will generally also comprise hydrophobic ligands, which are ligands comprising hydrophobic functional groups. Hydrophobic ligands may comprise alkyl groups, such as propyl, butyl, isopropyl, t-butyl or longer alkyl chains (e.g. C8 to C18 alkyl chains), aryl groups, such as phenyl groups, or combinations thereof. In one embodiment, the mixed-mode matrix comprises a hydrophobic ligand comprising an alkyl group, such as a C8 or C18 alkyl chain. In another embodiment, the mixed-mode matrix comprises a hydrophobic ligand comprising a phenyl group.

In certain preferred embodiments, the mixed-mode matrix used in the methods of the invention comprises a strong anion exchange ligand, a strong cation exchange ligand, and a hydrophobic ligand. In one embodiment, the strong anion exchange ligand comprises a quaternary amine, the strong cation exchange ligand comprises a sulfonyl functional group, and the hydrophobic ligand comprises an alkyl group. In such embodiments, the alkyl group is an alkyl chain comprising at least 8 carbon atoms. For instance, in one embodiment, the alkyl group comprises an octyl carbon chain (C8 alkyl chain). In another embodiment, the alkyl group comprises an octadecyl carbon chain (C18 alkyl chain). In other embodiments, the strong anion exchange ligand comprises a quaternary amine, the strong cation exchange ligand comprises a sulfonyl functional group, and the hydrophobic ligand comprises a phenyl group.

Mixed-mode matrices suitable for use in the methods of the invention are also described in Zhang and Liu, Journal of Pharmaceutical and Biomedical Analysis, Vol. 128: 73-88, 2016 and are also available commercially, such as the Scherzo line of columns available from Imtakt USA, including the SW-C18, SM-C18, and SS-C18 columns. The Scherzo SS-C18 column is preferred in some embodiments as the mixed-mode matrix for use in the methods of the invention.

Once the solution comprising the oligonucleotide or carbohydrate-oligonucleotide conjugate compound and one or more impurities is contacted with the mixed-mode matrix, a mobile phase is passed through the mixed-mode matrix to carry the components of the solution through the matrix thereby allowing the components to interact to varying degrees with the positively-charged, negatively-charged, and hydrophobic functional groups present in the matrix. As described in Example 1 herein, the composition of the mobile phase was designed to utilize both ion-exchange and reverse-phase interactions of the mixed-mode matrix to improve the separation of the carbohydrate-oligonucleotide conjugate compound from unconjugated oligonucleotides and other impurities.

The mobile phase used in the mixed-mode chromatography methods of the invention is typically a buffered solution at a pH of about 7.0 to about 8.5. In some embodiments, the pH of the mobile phase is about 7.0 to about 8.0. In other embodiments, the pH of the mobile phase is about 7.3 to about 7.7. In one particular embodiment, the pH of the mobile phase is about 7.5. Any buffer can be used provided that the buffer is capable of maintaining the pH of the solution in the target pH range. Suitable buffers that buffer in this pH range that can be used as components of the mobile phase in the mixed-mode chromatography methods of the invention include, but are not limited to, HEPES (N-[2-hydroxyethyl]piperazine-N'-[2-ethanesulfonic acid]), Tris hydrochloride, phosphate, BES (N,N-bis[2-hydroxyethyl]-2-aminoethanesulfonic acid), Tricine (N-tris[hydroxymethyl]methylglycine), Bicine (N,N-Bis(2-hydroxyethyl)glycine), TES (N-tris[hydroxymethyl]methyl-2-aminoethanesulfonic acid), TAPSO (3-[N-Tris (hydroxymethyl)methylamino]-2-hydroxypropanesulfonic acid), PIPES (piperazine-N,N'-bis(2-ethanesulfonic acid)), Bis-Tris (Bis(2-hydroxyethyl)amino-tris(hydroxymethyl) methane), and MOPS (3-[N-morpholino]propanesulfonic acid). In certain embodiments, the mobile phase comprises a buffer selected from sodium phosphate, Tris hydrochloride, HEPES, or MOPS. The buffer can be present in a concentration from about 20 mM to about 200 mM, from about 25 mM to about 175 mM, from about 40 mM to about 150 mM, from about 50 mM to about 125 mM, or from about 80 mM to about 110 mM. In some embodiments, the mobile phase comprises a Tris hydrochloride buffer, for example in a concentration of about 20 mM to about 200 mM. In other embodiments, the mobile phase comprises a HEPES buffer, for example in a concentration of about 20 mM to about 200 mM. In certain other embodiments, the mobile phase comprises a sodium phosphate buffer, for example in a concentration of about 20 mM to about 200 mM. In still other embodiments, the mobile phase comprises a MOPS buffer, for example in a concentration of about 20 mM to about 200 mM.

In certain embodiments, the mobile phase used in the mixed-mode chromatography methods of the invention comprises an organic solvent. Exemplary organic solvents that can be included in the mobile phase include, but are not limited to, acetonitrile, methanol, propanol, isopropanol, ethanol, butanol, tetrahydrofuran, and acetone. In some embodiments, the organic solvent is methanol, acetonitrile, or tetrahydrofuran. In one embodiment, the organic solvent is acetonitrile. In another embodiment, the organic solvent is methanol. In certain embodiments, the concentration of organic solvent in the mobile phase increases over the course of the separation. As described in Example 1, increasing the concentration of the organic solvent (e.g. acetonitrile) in the mobile phase took advantage of the reversed-phase mode of the mixed-mode matrix to allow for elution of the oligonucleotides from the matrix.

In some embodiments, the concentration of the organic solvent in the mobile phase at the start of the separation is at least about 8% (v/v) and increases over the course of the separation. In other embodiments, the concentration of the organic solvent in the mobile phase at the start of the separation is at least about 10% (v/v) and increases over the course of the separation. In certain embodiments, the increase in concentration of the organic solvent in the mobile phase is a concentration gradient of the organic solvent, for example, from about 8% (v/v) to about 20% (v/v), from about 10% (v/v) to about 18% (v/v), from about 10% (v/v) to about 20% (v/v), from about 8% (v/v) to about 14% (v/v), from about 9% (v/v) to about 16% (v/v), or from about 11% (v/v) to about 17% (v/v). In one embodiment, the concentration of the organic solvent in the mobile phase increases from about 8% (v/v) to about 20% (v/v) over the course of the separation. In another embodiment, the concentration of the organic solvent in the mobile phase increases from about 10% (v/v) to about 18% (v/v) over the course of the separation. In yet another embodiment, the concentration of the organic solvent in the mobile phase increases from about 11% (v/v) to about 17% (v/v) over the course of the separation.

The concentration gradient of organic solvent may be a linear gradient where the concentration of organic solvent in the mobile phase changes linearly over time. In other embodiments, the concentration gradient of organic solvent is a step gradient where the concentration of organic solvent in the mobile phase changes in discrete steps over time and the organic solvent concentration at each step is constant. Both types of gradients can be created by mixing different percentages of two buffers with different concentrations of the organic solvent at different times. By way of example, buffer A, which does not contain the organic solvent, can be mixed with buffer B, which comprises 20% (v/v) of the organic solvent, to create the gradients. By increasing the percentage of buffer B in the mixture with buffer A as a function of time allows the creation of a linear concentration gradient of the organic solvent from 0% to 20% (v/v). Similarly, a step gradient can be created by mixing specific percentages of buffer A and buffer B at particular time points during the separation as illustrated in the Examples and described in more detail below.

In some embodiments, the mobile phase used in the mixed-mode chromatography methods of the invention comprises an elution salt, the concentration of which increases over the time period of the separation. An elution salt refers to an ionic compound resulting from a neutralization reaction of an acid and a base. A salt is typically comprised of an equal number of cations and anions so that the overall net charge of the salt is zero. Suitable cations in the elution salt include, but are not limited to, sodium, potassium, ammonium, trimethylammonium, triethylammonium, lithium, calcium, and magnesium. In certain embodiments, the cation in the elution salt can be selected from sodium, potassium, ammonium, trimethylammonium, and triethylammonium. In some embodiments, the cation in the elution salt is sodium, potassium, or ammonium. In one embodiment, the cation in the elution salt is sodium. In another embodiment, the cation in the elution salt is potassium. Suitable anions in the elution salt include, but are not limited to, chloride, bromide, nitrate, nitrite, iodide, perchlorate, acetate, formate, phosphate, citrate, oxalate, and carbonate. The anion in the elution salt can, in some embodiments, be chloride, bromide, nitrate, nitrite, iodide, perchlorate, acetate, or formate. In one particular embodiment, the anion in the elution salt is chloride. In another particular embodiment, the anion in the elution salt is bromide.

Exemplary elution salts that can be included in the mobile phase for the mixed-mode chromatography methods of the invention include, but are not limited to, sodium chloride, sodium bromide, sodium nitrate, sodium nitrite, sodium acetate, sodium perchlorate, sodium iodide, sodium formate, potassium chloride, potassium bromide, potassium nitrate, potassium nitrite, potassium acetate, potassium perchlorate, potassium iodide, potassium formate, ammonium chloride, ammonium, bromide, ammonium acetate, trimethylammonium chloride, trimethylammonium bromide, trimethylammonium acetate, triethylammonium chloride, triethylammonium bromide, and triethylammonium acetate. In certain embodiments, the mobile phase comprises an elution salt selected from sodium bromide, potassium bromide, ammonium bromide, sodium chloride, potassium chloride, and ammonium chloride. In one embodiment, the elution salt in the mobile phase is sodium bromide. In another embodiment, the elution salt in the mobile phase is potassium bromide. In another embodiment, the elution salt in the mobile phase is ammonium bromide. In yet another embodiment, the elution salt in the mobile phase is sodium chloride.

During the separation, the concentration of the elution salt in the mobile phase is increased to disrupt the electrostatic interactions between the oligonucleotides and the carbohydrate-oligonucleotide conjugate compounds and the ion-exchange ligands in the mixed-mode matrix. The increase in concentration of the elution salt in the mobile phase can be a concentration gradient of the elution salt, for example from 0 M to 2 M, from 0 M to 1 M, from 0 M to 0.5 M, from about 0.5 M to about 1 M, or from about 0.5 M to 2 M. In some embodiments, the gradient is a linear gradient where the concentration of elution salt in the mobile phase changes linearly over time. In other embodiments, the gradient is a step gradient where the concentration of elution salt in the mobile phase changes in discrete steps over time and the elution salt concentration at each step is constant. As described above for the creation of organic solvent concentration gradients, both linear and step gradients of the elution salt can be similarly created by mixing different percentages of two buffers with different concentrations of the elution salt at different times. In one embodiment, the increase in concentration of the elution salt in the mobile phase is a linear gradient from about 0.5 M to about 1 M. In another embodiment, the increase in concentration of the elution salt in the mobile phase is a linear gradient from about 0.5 M to about 0.85 M. In yet another embodiment, the increase in concentration of the elution salt in the mobile phase is a step gradient from about 0.5 M to about 1 M. In still another embodiment, the increase in concentration of the elution salt in the mobile phase is a step gradient from about 0.5 M to about 0.85 M.

In certain preferred embodiments, the mobile phase employed in the mixed-mode chromatography methods of the invention comprises a dual salt/organic solvent gradient. Thus, in some embodiments, the concentrations of organic solvent and the elution salt in the mobile phase increase over the course of the separation. In one embodiment, the mobile phase comprises an organic solvent gradient from about 8% (v/v) to about 20% (v/v) and an elution salt gradient from 0 M to about 1 M. In another embodiment, the mobile phase comprises an organic solvent gradient from about 8% (v/v) to about 20% (v/v) and an elution salt gradient from about 0.5 M to about 1 M. In yet another embodiment, the mobile phase comprises an organic solvent gradient from about 10% (v/v) to about 18% (v/v) and an elution salt gradient from about 0.5 M to about 1 M. In still another embodiment, the mobile phase comprises an organic solvent gradient from about 11% (v/v) to about 17% (v/v) and an elution salt gradient from about 0.5 M to about 0.85 M. An exemplary dual salt/organic solvent gradient for the mobile phase for the mixed-mode chromatography methods of the invention is described in the following table, where Buffer A does not contain any elution salt (i.e. 0 M) or organic solvent (i.e. 0% (v/v)) and Buffer B contains 1 M elution salt and 20% (v/v) organic solvent:

| Time (min) | % Buffer B |
|---|---|
| 0 | 55 |
| 40 | 80 |
| 45 | 85 |
| 50 | 85 |
| 51 | 55 |
| 70 | 55 |

Other possible gradients and methods for creating the gradients to increase the concentration of the elution salt and/or the organic solvent in the mobile phase over the course of the separation are known to those of skill in the art.

In some embodiments of the mixed-mode chromatography methods of the invention, the mobile phase has a pH of about 7.0 to about 8.5 and comprises about 20 mM to about 200 mM buffer, an organic solvent, and an elution salt, wherein the concentration of the organic solvent increases at a gradient of about 8% (v/v) to about 20% (v/v) and the concentration of the elution salt increases at a gradient of 0 M to about 1 M over time. In other embodiments, the mobile phase has a pH of about 7.0 to about 8.0 and comprises about 20 mM to about 200 mM buffer, an organic solvent, and an elution salt, wherein the concentration of the organic solvent increases at a gradient of about 10% (v/v) to about 18% (v/v) and the concentration of the elution salt increases at a gradient of about 0.5 M to about 1 M over time. For any of these mobile phase compositions, the buffer can be sodium phosphate or Tris hydrochloride, the organic solvent can be acetonitrile or methanol, and the elution salt can be sodium bromide, potassium bromide, or ammonium bromide. For instance, in certain embodiments, the mobile phase has a pH of about 7.0 to about 8.5 and comprises about 20 mM to about 200 mM Tris hydrochloride buffer, acetonitrile, and sodium bromide, wherein the concentration of acetonitrile in the mobile phase increases at a gradient of about 8% (v/v) to about 20% (v/v) and the concentration of sodium bromide in the mobile phase increases at a gradient of 0 M to about 1 M over time. In some embodiments, the mobile phase has a pH of about 7.0 to about 8.0 and comprises about 20 mM to about 200 mM Tris hydrochloride buffer, acetonitrile, and sodium bromide, wherein the concentration of acetonitrile in the mobile phase increases at a gradient of about 8% (v/v) to about 20% (v/v) and the concentration of sodium bromide in the mobile phase increases at a gradient of about 0.5 M to about 1 M over time. In other embodiments, the mobile phase has a pH of about 7.3 to about 7.7 and comprises about 80 mM to about 110 mM Tris hydrochloride buffer, acetonitrile, and sodium bromide, wherein the concentration of acetonitrile in the mobile phase increases at a gradient of about 10% (v/v) to about 18% (v/v) and the concentration of sodium bromide in the mobile phase increases at a gradient of about 0.5 M to about 1 M over time. In one embodiment, the mobile phase has a pH of about 7.5 and comprises about 100 mM Tris hydrochloride buffer, acetonitrile, and sodium bromide, wherein the concentration of acetonitrile in the mobile phase increases at a gradient of about 11% (v/v) to about 17% (v/v) and the concentration of sodium bromide in the mobile phase increases at a gradient of about 0.5 M to about 0.85 M over time.

In certain embodiments of the mixed-mode chromatography methods of the invention, the mobile phase has a pH of about 7.0 to about 8.5 and comprises about 20 mM to about 200 mM Tris hydrochloride buffer, methanol, and sodium bromide, wherein the concentration of methanol in the mobile phase increases at a gradient of about 8% (v/v) to about 20% (v/v) and the concentration of sodium bromide in the mobile phase increases at a gradient of 0 M to about 1 M over time. In some embodiments, the mobile phase has a pH of about 7.0 to about 8.0 and comprises about 20 mM to about 200 mM Tris hydrochloride buffer, methanol, and sodium bromide, wherein the concentration of methanol in the mobile phase increases at a gradient of about 8% (v/v) to about 20% (v/v) and the concentration of sodium bromide in the mobile phase increases at a gradient of about 0.5 M to about 1 M over time. In other embodiments, the mobile phase has a pH of about 7.3 to about 7.7 and comprises about 80 mM to about 110 mM Tris hydrochloride buffer, methanol, and sodium bromide, wherein the concentration of methanol in the mobile phase increases at a gradient of about 10% (v/v) to about 18% (v/v) and the concentration of sodium bromide in the mobile phase increases at a gradient of about 0.5 M to about 1 M over time. In yet other embodiments, the mobile phase has a pH of about 7.0 to about 8.5 and comprises about 20 mM to about 200 mM sodium phosphate buffer, methanol, and sodium bromide, wherein the concentration of methanol in the mobile phase increases at a gradient of about 8% (v/v) to about 20% (v/v) and the concentration of sodium bromide in the mobile phase increases at a gradient of 0 M to about 1 M over time. In still other embodiments, mobile phase has a pH of about 7.0 to about 8.0 and comprises about 20 mM to about 200 mM sodium phosphate buffer, methanol, and sodium bromide, wherein the concentration of methanol in the mobile phase increases at a gradient of about 8% (v/v) to about 20% (v/v) and the concentration of sodium bromide in the mobile phase increases at a gradient of about 0.5 M to about 1 M over time. In certain other embodiments, the mobile phase has a pH of about 7.0 to about 8.5 and comprises about 20 mM to about 200 mM sodium phosphate buffer, acetonitrile, and sodium bromide, wherein the concentration of acetonitrile in the mobile phase increases at a gradient of about 8% (v/v) to about 20% (v/v) and the concentration of sodium bromide in the mobile phase increases at a gradient of 0 M to about 1 M over time. In still other embodiments, the mobile phase has a pH of about 7.0 to about 8.0 and comprises about 20 mM to about 200 mM sodium phosphate buffer, acetonitrile, and sodium bromide, wherein the concentration of acetonitrile in the mobile phase increases at a gradient of about 8% (v/v) to about 20% (v/v) and the concentration of sodium bromide in the mobile phase increases at a gradient of about 0.5 M to about 1 M over time. In any of the mobile phase buffers described above, potassium bromide or ammonium bromide can be used as the elution salt in place of sodium bromide.

As the solution comprising the oligonucleotide/carbohydrate-oligonucleotide conjugate compound and one or more impurities is moved through the mixed-mode matrix with the mobile phase described above, elution fractions are collected. The oligonucleotide content in the fractions can be monitored using UV absorption, e.g. at 260 nm. As shown by the chromatograms in FIG. 2, when the mixed-mode chromatography is operated according to the methods of the invention, the unconjugated oligonucleotide (e.g. an impurity in this context) elutes from the mixed-mode matrix prior to the carbohydrate-oligonucleotide conjugate compound (e.g. GalNAc-oligo), thus enabling the collection of a set of fractions for the carbohydrate-oligonucleotide conjugate compound separate from one or more impurities. Samples from the elution fractions can be analyzed by gel electrophoresis, capillary electrophoresis, ion-pairing reversed phase liquid chromatography-mass spectrometry, analytical ion exchange chromatography, and/or native mass spectrometry to verify the enrichment of the fractions for the carbohydrate-oligonucleotide conjugate compound or other target oligonucleotide.

In certain embodiments, the target oligonucleotide or carbohydrate-oligonucleotide conjugate compound to be purified according to the mixed-mode chromatography methods of the invention comprises one or more phosphorothioate internucleotide linkages. As discussed above, incorporation of a phosphorothioate internucleotide linkage creates a diastereomer pair (Rp and Sp) at each such linkage. As described in Example 2 herein, the mixed-mode chromatography methods of the invention allow for separation of sets of phosphorothioate diastereomers. Thus, in some embodiments, the methods comprise contacting a solution comprising an oligonucleotide that comprises at least one phosphorothioate internucleotide linkage and one or more phosphorothioate diastereomers of the oligonucleotide with a mixed-mode matrix as described herein; passing a mobile phase through the mixed-mode matrix, wherein the mobile phase has a pH of about 7.0 to about 8.5 and comprises a buffer, an organic solvent, and an elution salt, and wherein the concentrations of the elution salt and organic solvent increase over time; and collecting elution fractions from the mixed-mode matrix, wherein a first diastereomer of the oligonucleotide elutes in a separate set of elution fractions than a second diastereomer of the oligonucleotide. In certain embodiments, the methods comprise contacting a solution comprising a carbohydrate-oligonucleotide conjugate compound that comprises at least one phosphorothioate internucleotide linkage and one or more phosphorothioate diastereomers of the conjugate compound with a mixed-mode matrix as described herein; passing a mobile phase through the mixed-mode matrix, wherein the mobile phase has a pH of about 7.0 to about 8.5 and comprises a buffer, an organic solvent, and an elution salt, and wherein the concentrations of the elution salt and organic solvent increase over time; and collecting elution fractions from the mixed-mode matrix, wherein a first diastereomer of the conjugate compound elutes in a separate set of elution fractions than a second diastereomer of the conjugate compound. In some embodiments, the methods may further comprise isolating the set of elution fractions that comprise a specific phosphorothioate diastereomer or set of phosphorothioate diastereomers.

In another aspect, the present invention provides methods for purifying an oligonucleotide, particularly a carbohydrate-oligonucleotide conjugate compound, from one or more impurities by contacting a solution comprising the oligonucleotide or carbohydrate-oligonucleotide conjugate compound and one or more impurities with an anion-exchange matrix and eluting the oligonucleotide or carbohydrate-oligonucleotide conjugate compound from the anion-exchange matrix with a dual pH/salt gradient. In one embodiment, the method comprises contacting a solution comprising the oligonucleotide or carbohydrate-oligonucleotide conjugate compound and one or more impurities with an anion-exchange matrix; passing a mobile phase through the anion-exchange matrix, wherein the mobile phase has a pH of at least about 8.5 and comprises a buffer, an organic solvent, and an elution salt, wherein the concentration of the elution salt and the pH of the mobile phase increases over time; and collecting elution fractions from the anion-exchange matrix, wherein the oligonucleotide or carbohydrate-oligonucleotide conjugate compound is eluted in a first set of elution fractions and one or more impurities are eluted in a second set of elution fractions, thereby separating the oligonucleotide or carbohydrate-oligonucleotide conjugate compound from the impurities.

Accordingly, in such embodiments of the methods of the invention, a solution comprising the target oligonucleotide or carbohydrate-oligonucleotide conjugate compound to be purified is contacted with an anion-exchange matrix. An anion-exchange matrix refers to a material to which one or more anion exchange ligands have been attached. Anion exchange ligands generally comprise functional groups that are positively charged or chargeable. The material to which the anion exchange ligands are attached can be made from polymers, such as cross-linked carbohydrates, including agarose, agar, cellulose, dextran, and chitosan, or cross-linked synthetic polymers, including styrene or styrene derivatives, divinylbenzene, acrylamides, acrylate esters, methacrylate esters, vinyl esters, vinyl amides and the like. Other suitable materials include inorganic polymers, such as silica. The material can be in the form of beads or particles.

In certain embodiments, the anion-exchange matrix comprises strong anion exchange ligands, which refer to ligands comprising strong anion exchange groups that show no variation in ion exchange capacity with changes in pH and are fully charged over a wide pH range (e.g. at pH values between 2 and 13). Strong anion exchange ligands may comprise quaternary amines, such as quaternary aminoethyl, quaternary ammonium, and quaternary aminomethyl. Anion-exchange matrices suitable for use in the methods of the invention are also available commercially, such as the TSKgel SuperQ-5PW column available from Tosoh Bioscience, the Source Q15 and Q30 columns available from GE Healthcare, and the DNAPac PA100 and PA200 columns available from ThermoFisher Scientific. The TSKgel SuperQ-5PW column is preferred in some embodiments as the anion-exchange matrix for use in the methods of the invention. Other strong anion-exchange matrices may also be used in the methods of the invention so long as the matrices are stable over the pH range employed for the pH gradient of the mobile phase (e.g. pH 8.5 to 12).

The mobile phase for eluting the oligonucleotide or carbohydrate-oligonucleotide conjugate compound from the anion-exchange matrix will generally comprise a buffer, an organic solvent, and an elution salt. In some embodiments, the mobile phase has an initial pH of at least about 8.5 and increases in pH over the course of the separation. As described in Example 3 herein, the change in pH allows for modulation of the ionization of the carbohydrate-oligonucleotide conjugate compound without affecting the ionization of the strong anion-exchange matrix to improve the separation of the conjugate compound from unconjugated oligonucleotide and other impurities. Thus, in certain embodiments, the pH of the mobile phase increases from about 8.5 to about 12, from about 8.5 to about 11, from about 8.5 to about 10.5, from about 8.5 to about 9.5, from about 9.0 to about 10.5, from about 9.5 to about 10.5, or from about 9.5 to about 11, over the course of the separation. In some embodiments, the pH of the mobile phase increases from about 8.5 to about 11 over the course of the separation. In other embodiments, the pH of the mobile phase increases from about 9.0 to about 10.5 over the course of the separation. In still other embodiments, the pH of the mobile phase increases from about 8.5 to about 10.5 over the course of the separation. Any buffer can be used provided that the buffer is capable of maintaining the pH of the mobile phase across the range of the pH gradient. Suitable buffers that buffer over the target pH gradient range that can be used as components of the mobile phase in the anion-exchange chromatography methods of the invention include, but are not limited to, phosphate, glycine, carbonate, bicarbonate, CAPS (3-(Cyclohexylamino)-1-propanesulfonic acid), CAPSO (3-(Cyclohexylamino)-2-hydroxy-1-propanesulfonic acid), CABS (4-(Cyclohexylamino)-1-butanesulfonic acid), CHES (2-(Cyclohexylamino)ethanesulfonic acid), AMPSO (N-(1,1-Dimethyl-2-hydroxyethyl)-3-amino-2-hydroxypropanesulfonic acid), AMP (2-Amino-2-methyl-1-propanol), and AMPD (2-Amino-2-methyl-1,3-propanediol). In one embodiment, the mobile phase comprises a sodium phosphate buffer. The buffer can be present in a concentration from about 10 mM to about 200 mM, from about 15 mM to about 150 mM, from about 20 mM to about 100 mM, from about 25 mM to about 75 mM, or from about 15 mM to about 25 mM. In some embodiments, the mobile phase comprises a sodium phosphate buffer, for example in a concentration of about 20 mM to about 100 mM.

In certain embodiments, the mobile phase used in the anion-exchange chromatography methods of the invention comprises an organic solvent. Exemplary organic solvents that can be included in the mobile phase include, but are not limited to, acetonitrile, methanol, propanol, isopropanol, ethanol, butanol, tetrahydrofuran, and acetone. In some embodiments, the organic solvent is methanol, acetonitrile, or tetrahydrofuran. In one embodiment, the organic solvent is acetonitrile. In another embodiment, the organic solvent is methanol. The concentration of the organic solvent in the mobile phase used in the anion-exchange chromatography methods of the invention can be from about 1% (v/v) to about 50% (v/v), from about 1% (v/v) to about 20% (v/v), from about 15% (v/v) to about 35% (v/v), from about 5% (v/v) to about 15% (v/v), from about 5% (v/v) to about 25% (v/v), from about 1% (v/v) to about 10% (v/v), from about 10% (v/v) to about 20% (v/v), from about 8% (v/v) to about 12% (v/v), or from about 12% (v/v) to about 18% (v/v). In one embodiment, the organic solvent is present in the mobile phase at a concentration of about 10% (v/v). In another embodiment, the organic solvent is present in the mobile phase at a concentration of about 15% (v/v). In yet another embodiment, the organic solvent is present in the mobile phase at a concentration of about 20% (v/v). In certain embodiments, the concentration of the organic solvent in the mobile phase used in the anion-exchange chromatography methods of the invention remains constant throughout the separation.

In some embodiments, the mobile phase used in the anion-exchange chromatography methods of the invention comprises an elution salt, the concentration of which increases over the time period of the separation. Any of the elution salts described above for use in the mobile phase for the mixed-mode chromatography methods of the invention can be used for the mobile phase for the anion-exchange chromatography methods as well. For instance, suitable cations in the elution salt can include, but are not limited to, sodium, potassium, ammonium, trimethylammonium, triethylammonium, lithium, calcium, and magnesium. In certain embodiments, the cation in the elution salt can be selected from sodium, potassium, ammonium, trimethylammonium, and triethylammonium. In some embodiments, the cation in the elution salt is sodium, potassium, or ammonium. In one embodiment, the cation in the elution salt is sodium. In another embodiment, the cation in the elution salt is potassium. Suitable anions in the elution salt can include, but are not limited to, chloride, bromide, nitrate, nitrite, iodide, perchlorate, acetate, formate, phosphate, citrate, oxalate, and carbonate. In some embodiments, the anion in the elution salt is chloride, bromide, nitrate, nitrite, iodide, perchlorate, acetate, or formate. In one particular embodiment, the anion in the elution salt is chloride. In another particular embodiment, the anion in the elution salt is bromide. Exemplary elution salts that can be included in the mobile phase for the anion-exchange chromatography methods of the invention include, but are not limited to, sodium chloride, sodium bromide, sodium nitrate, sodium nitrite, sodium acetate, sodium perchlorate, sodium iodide, sodium formate, potassium chloride, potassium bromide, potassium nitrate, potassium nitrite, potassium acetate, potassium perchlorate, potassium iodide, potassium formate, ammonium chloride, ammonium, bromide, ammonium acetate, trimethylammonium chloride, trimethylammonium bromide, trimethylammonium acetate, triethylammonium chloride, triethylammonium bromide, and triethylammonium acetate. In certain embodiments, the mobile phase comprises an elution salt selected from sodium bromide, potassium bromide, ammonium bromide, sodium chloride, potassium chloride, and ammonium chloride. In one embodiment, the elution salt in the mobile phase for the anion-exchange chromatography methods of the invention is sodium chloride. In another embodiment, the elution salt in the mobile phase is sodium bromide. In another embodiment, the elution salt in the mobile phase is potassium chloride. In yet another embodiment, the elution salt in the mobile phase is ammonium chloride.

During the separation, the concentration of the elution salt in the mobile phase is increased to disrupt the electrostatic interactions between the oligonucleotides and the carbohydrate-oligonucleotide conjugate compounds and the positively-charged functional groups in the anion-exchange matrix. The increase in concentration of the elution salt in the mobile phase for the anion-exchange chromatography methods of the invention can be a concentration gradient of the elution salt, for example from 0 M to about 2 M, from 0 M to about 1 M, from 0 M to about 0.5 M, from about 0.5 M to about 1 M, from about 0.3 M to about 0.7 M, from about 0.2 M to about 0.8 M, or from about 0.5 M to about 2 M. In some embodiments, the gradient is a linear gradient where the concentration of elution salt in the mobile phase changes linearly over time. In other embodiments, the gradient is a step gradient where the concentration of elution salt in the mobile phase changes in discrete steps over time and the elution salt concentration at each step is constant. As described above for the elution salt gradients in the mobile phase buffer for the mixed-mode chromatography methods of the invention, both linear and step gradients of the elution salt can be created by mixing different percentages of two buffers with different concentrations of the elution salt at different times. In one embodiment, the increase in concentration of the elution salt in the mobile phase for the anion-exchange chromatography methods is a linear gradient from about 0 M to about 1 M. In another embodiment, the increase in concentration of the elution salt in the mobile phase is a linear gradient from about 0.3 M to about 0.7 M. In yet another embodiment, the increase in concentration of the elution salt in the mobile phase for the anion-exchange chromatography methods is a step gradient from about 0 M to about 1 M. In still another embodiment, the increase in concentration of the elution salt in the mobile phase is a step gradient from about 0.3 M to about 0.7 M.

In certain preferred embodiments, the mobile phase used for the anion-exchange chromatography methods of the invention increases in pH over time and the concentration of elution salt in the mobile phase also increases over time. In other words, the mobile phase comprises a dual pH/salt gradient to separate the target oligonucleotide or carbohydrate-oligonucleotide conjugate compound from one or more impurities. As described in Example 3 herein, utilization of a mobile phase comprising the dual pH/salt gradient provided improved separation of the intact carbohydrate-oligonucleotide conjugate compound (e.g. GalNAc-oligo) from the unconjugated oligonucleotide and other impurities as compared with a mobile phase comprising just a salt gradient. Accordingly, in some embodiments, the mobile phase comprises a pH gradient from about 8.5 to about 11 and an elution salt gradient from about 0 M to about 1 M. In other embodiments, the mobile phase comprises a pH gradient from about 9.0 to about 10.5 and an elution salt gradient from about 0.3 M to about 0.7 M. In yet other embodiments, the mobile phase comprises a pH gradient from about 8.5 to about 10.5 and an elution salt gradient from about 0 M to about 0.8 M. An exemplary dual pH/salt gradient for the mobile phase for the anion-exchange chromatography methods of the invention is described in the following table, where Buffer A has a pH of 8.5 and does not contain any elution salt (i.e. 0 M) and Buffer B has a pH of 11 and contains 1 M elution salt:

| Time (min) | % Buffer B |
|---|---|
| 0 | 30 |
| 15 | 65 |
| 16 | 70 |
| 19 | 70 |
| 19.1 | 0 |

Other possible gradients and methods for creating the gradients to increase the concentration of the elution salt and increase the pH of the mobile phase over the course of the separation are known to those of skill in the art.

In some embodiments of the anion-exchange chromatography methods of the invention, the mobile phase comprises about 10 mM to about 200 mM buffer, about 1% (v/v) to about 50% (v/v) organic solvent, and an elution salt, wherein the concentration of the elution salt increases at a gradient of about 0 M to about 1 M and the pH of the mobile phase increases from a pH of about 8.5 to about 11 over time. In other embodiments, the mobile phase comprises about 20 mM to about 100 mM buffer, about 1% (v/v) to about 20% (v/v) organic solvent, and an elution salt, wherein the concentration of the elution salt increases at a gradient of about 0 M to about 1 M and the pH of the mobile phase increases from a pH of about 8.5 to about 11 over time. For any of these mobile phase compositions, the buffer can be sodium phosphate, the organic solvent can be acetonitrile or methanol, and the elution salt can be sodium chloride, potassium chloride, or ammonium chloride. For instance, in certain embodiments, the mobile phase comprises about 10 mM to about 200 mM sodium phosphate buffer, about 1% (v/v) to about 50% (v/v) acetonitrile, and sodium chloride, wherein the concentration of sodium chloride increases at a gradient of about 0 M to about 1 M and the pH of the mobile phase increases from a pH of about 8.5 to about 11 over time. In some embodiments, the mobile phase comprises about 20 mM to about 100 mM sodium phosphate buffer, about 1% (v/v) to about 20% (v/v) acetonitrile, and sodium chloride, wherein the concentration of sodium chloride increases at a gradient of about 0 M to about 1 M and the pH of the mobile phase increases from a pH of about 8.5 to about 11 over time. In other embodiments, the mobile phase comprises about 15 mM to about 25 mM sodium phosphate buffer, about 12% (v/v) to about 18% (v/v) acetonitrile, and sodium chloride, wherein the concentration of sodium chloride increases at a gradient of about 0 M to about 1 M and the pH of the mobile phase increases from a pH of about 8.5 to about 11 over time. In still other embodiments, the mobile phase comprises about 15 mM to about 25 mM sodium phosphate buffer, about 12% (v/v) to about 18% (v/v) acetonitrile, and sodium chloride, wherein the concentration of sodium chloride increases at a gradient of about 0 M to about 0.8 M and the pH of the mobile phase increases from a pH of about 8.5 to about 10.5 over time. In one embodiment, the mobile phase comprises about 20 mM sodium phosphate buffer, about 15% (v/v) acetonitrile, and sodium chloride, wherein the concentration of sodium chloride increases at a gradient of about 0.3 M to about 0.7 M and the pH of the mobile phase increases from a pH of about 9.0 to about 10.5 over time. In these and other embodiments, the concentration of acetonitrile in the mobile phase may remain constant over time.

In certain embodiments of the anion-exchange chromatography methods of the invention, the mobile phase comprises about 10 mM to about 200 mM sodium phosphate buffer, about 1% (v/v) to about 50% (v/v) methanol, and sodium chloride, wherein the concentration of sodium chloride increases at a gradient of about 0 M to about 1 M and the pH of the mobile phase increases from a pH of about 8.5 to about 11 over time. In some embodiments, the mobile phase comprises about 20 mM to about 100 mM sodium phosphate buffer, about 1% (v/v) to about 20% (v/v) methanol, and sodium chloride, wherein the concentration of sodium chloride increases at a gradient of about 0 M to about 1 M and the pH of the mobile phase increases from a pH of about 8.5 to about 11 over time. In other embodiments, the mobile phase comprises about 15 mM to about 25 mM sodium phosphate buffer, about 12% (v/v) to about 18% (v/v) methanol, and sodium chloride, wherein the concentration of sodium chloride increases at a gradient of about 0 M to about 1 M and the pH of the mobile phase increases from a pH of about 8.5 to about 11 over time. In still other embodiments, the mobile phase comprises about 15 mM to about 25 mM sodium phosphate buffer, about 12% (v/v) to about 18% (v/v) methanol, and sodium chloride, wherein the concentration of sodium chloride increases at a gradient of about 0 M to about 0.8 M and the pH of the mobile phase increases from a pH of about 8.5 to about 10.5 over time. In any of the mobile phase buffers described above, potassium chloride or ammonium chloride can be used as the elution salt in place of sodium chloride.

As the solution comprising the oligonucleotide/carbohydrate-oligonucleotide conjugate compound and one or more impurities is moved through the anion-exchange matrix with the mobile phase described herein (e.g. dual pH/salt gradient mobile phase), elution fractions are collected. The oligonucleotide content in the fractions can be monitored using UV absorption, e.g. at 260 nm. As shown by the chromatograms in FIGS. 9A to 9C, when the anion-exchange chromatography is operated according to the methods of the invention, the carbohydrate-oligonucleotide conjugate compound (e.g. GalNAc-oligo) elutes from the anion-exchange matrix prior to the unconjugated oligonucleotide (e.g. an impurity in this context), thus enabling the collection of a set of fractions for the carbohydrate-oligonucleotide conjugate compound separate from one or more impurities. Samples from the elution fractions can be analyzed by gel electrophoresis, capillary electrophoresis, ion-pairing reversed phase liquid chromatography-mass spectrometry, analytical ion exchange chromatography, and/or native mass spectrometry to verify the enrichment of the fractions for the carbohydrate-oligonucleotide conjugate compound or other target oligonucleotide.

The separation using either the mixed-mode matrix or the anion-exchange matrix according to the methods of the invention can be carried out at temperatures from about 5° C. to about 45° C. In certain embodiments, the separation using either the mixed-mode matrix or the anion-exchange matrix according to the methods of the invention is conducted at ambient temperature. For instance, in some embodiments, the separation using the mixed-mode matrix or the anion-exchange matrix is conducted at a temperature of about 15° C. to about 25° C. In other embodiments, the separation using the mixed-mode matrix or the anion-exchange matrix is conducted at a temperature of about 18° C. to about 22° C. In yet other embodiments, the separation using the mixed-mode matrix or the anion-exchange matrix is conducted at a temperature of about 20° C. to about 25° C.

In certain embodiments of the mixed-mode chromatography or anion-exchange chromatography methods of the invention, the elution fraction or set of elution fractions comprising the target oligonucleotide or carbohydrate-oligonucleotide conjugate compound can be isolated and optionally pooled for further processing. For instance, the elution fraction(s) containing the target oligonucleotide or carbohydrate-oligonucleotide conjugate compound may be subject to one or more further purification steps, such as affinity separation (e.g. nucleic acid hybridization using sequence-specific reagents), additional ion exchange chromatography steps (e.g. using different stationary phases), mixed-mode chromatography steps, reverse-phase chromatography, or size-exclusion chromatography (e.g. with a desalting column). In some embodiments of the mixed-mode chromatography methods of the invention, the methods comprise isolating the elution fraction or set of elution fractions comprising the target oligonucleotide or carbohydrate-oligonucleotide conjugate compound and subjecting the elution fraction(s) to anion-exchange chromatography, such as the anion-exchange chromatography method of the invention described herein. In some embodiments of the anion-exchange chromatography methods of the invention, the methods comprise isolating the elution fraction or set of elution fractions comprising the target oligonucleotide or carbohydrate-oligonucleotide conjugate compound and subjecting the elution fraction(s) to mixed-mode chromatography, such as the mixed-mode chromatography method of the invention described herein.

As described in the Examples herein, the mixed-mode chromatography methods of the invention provide an orthogonal separation to the anion-exchange chromatography methods of the invention. Accordingly, in certain embodiments, the two methods can be used in combination to achieve superior purification and yield of target oligonucleotides, particularly carbohydrate-oligonucleotide conjugate compounds. For instance, in some embodiments, the anion-exchange chromatography method is performed first followed by the mixed-mode chromatography method. Thus, in certain embodiments, the methods of the invention comprise:

- contacting a solution comprising a target oligonucleotide or carbohydrate-oligonucleotide conjugate compound and one or more impurities with an anion-exchange matrix, wherein the anion-exchange matrix comprises a strong anion exchange ligand;
- passing a first mobile phase through the anion-exchange matrix, wherein the first mobile phase has a pH of at least about 8.5 and comprises a buffer, an organic solvent, and an elution salt, and wherein the concentration of the elution salt and the pH of the first mobile phase increases over time;
- collecting elution fractions from the anion-exchange matrix comprising the target oligonucleotide or carbohydrate-oligonucleotide conjugate compound to create an eluate pool;
- contacting the eluate pool with a mixed-mode matrix, wherein the mixed-mode matrix comprises a strong anion exchange ligand, a strong cation exchange ligand, and a hydrophobic ligand;
- passing a second mobile phase through the mixed-mode matrix, wherein the second mobile phase has a pH of about 7.0 to about 8.5 and comprises a buffer, an organic solvent, and an elution salt, and wherein the concentrations of the elution salt and organic solvent increase over time; and
- collecting elution fractions from the mixed-mode matrix, wherein the elution fractions comprise purified target oligonucleotide or carbohydrate-oligonucleotide conjugate compound.

In other embodiments, the mixed-mode chromatography method is performed first followed by the anion-exchange chromatography method. Therefore, in certain embodiments, the methods of the invention comprise:

- contacting a solution comprising a target oligonucleotide or carbohydrate-oligonucleotide conjugate compound and one or more impurities with a mixed-mode matrix, wherein the mixed-mode matrix comprises a strong anion exchange ligand, a strong cation exchange ligand, and a hydrophobic ligand;
- passing a first mobile phase through the mixed-mode matrix, wherein the first mobile phase has a pH of about 7.0 to about 8.5 and comprises a buffer, an organic solvent, and an elution salt, and wherein the concentrations of the elution salt and organic solvent increase over time;
- collecting elution fractions from the mixed-mode matrix comprising the target oligonucleotide or carbohydrate-oligonucleotide conjugate compound to create an eluate pool;
- contacting the eluate pool with an anion-exchange matrix, wherein the anion-exchange matrix comprises a strong anion exchange ligand;
- passing a second mobile phase through the anion-exchange matrix, wherein the second mobile phase has a pH of at least about 8.5 and comprises a buffer, an organic solvent, and an elution salt, and wherein the concentration of the elution salt and the pH of the second mobile phase increases over time; and
- collecting elution fractions from the anion-exchange matrix, wherein the elution fractions comprise purified target oligonucleotide or carbohydrate-oligonucleotide conjugate compound.

Elution fractions collected from either the mixed-mode matrix or the anion-exchange matrix comprising the target oligonucleotide or the carbohydrate-oligonucleotide conjugate compound according to the methods of the invention may be subject to other reactions to modify the structure of the oligonucleotide or the carbohydrate-oligonucleotide conjugate compound. For example, in embodiments in which the oligonucleotide or the carbohydrate-oligonucleotide conjugate compound is a therapeutic molecule (e.g. antisense oligonucleotide) or component of a therapeutic molecule (e.g. double-stranded RNA interference agent, such as siRNA), the purified oligonucleotide or the carbohydrate-oligonucleotide conjugate compound in the elution fraction(s) may be formulated in a pharmaceutical composition with a pharmaceutically acceptable excipient for administration to patients for therapeutic purposes. In embodiments in which a target oligonucleotide is to be purified, the purified oligonucleotide in the elution fraction(s) may be subject to a conjugation reaction to covalently attach a targeting ligand, such as a carbohydrate-containing ligand (e.g. to create a carbohydrate-oligonucleotide conjugate compound), cholesterol, antibody, and the like, to the oligonucleotide. In other embodiments, the purified oligonucleotide in the elution fraction(s) may be encapsulated in exosomes, liposomes, or other type of lipid nanoparticle. In embodiments in which the oligonucleotide or the carbohydrate-oligonucleotide conjugate compound is a component of a double-stranded RNA interference agent (e.g. either the sense strand or antisense strand of an siRNA molecule), the purified oligonucleotide or carbohydrate-oligonucleotide conjugate compound in the elution fraction(s) may be subject to an annealing reaction to hybridize the oligonucleotide or carbohydrate-oligonucleotide conjugate compound with its complementary strand to form the double-strand RNA interference agent.

The methods of the invention provide substantially pure preparations of the target oligonucleotide or carbohydrate-oligonucleotide conjugate compound. For instance, in some embodiments, the purity of the oligonucleotide or carbohydrate-oligonucleotide conjugate compound in elution fractions from the mixed-mode matrix or anion-exchange matrix is at least 75%, at least 80%, at least 85%, at least 90%, at least 91%, at least 92%, at least 93%, at least 94%, at least 95%, at least 96%, at least 97%, at least 98%, or at least 99%. In certain embodiments, the purity of the oligonucleotide or the carbohydrate-oligonucleotide conjugate compound in elution fractions from the mixed-mode matrix or anion-exchange matrix is at least 90%. In other embodiments, the purity of the oligonucleotide or the carbohydrate-oligonucleotide conjugate compound in elution fractions from the mixed-mode matrix or anion-exchange matrix is at least 92%. In still other embodiments, the purity of the oligonucleotide or the carbohydrate-oligonucleotide conjugate compound in elution fractions from the mixed-mode matrix or anion-exchange matrix is at least 94%. Methods of detecting and quantitating oligonucleotides are known to those of skill in the art and can include ion-pairing reversed phase liquid chromatography-mass spectrometry methods and analytical ion exchange methods, such as those described in the examples.

The following examples, including the experiments conducted and the results achieved, are provided for illustrative purposes only and are not to be construed as limiting the scope of the appended claims.

EXAMPLES

Example 1. Purification of GalNAc-Conjugated Oligonucleotides Using Mixed-Mode Chromatography Ion-exchange chromatography has been one of the key chromatographic techniques for purification of oligonucleotides given that these molecules contain a large number of charges and are mostly hydrophilic in nature. As a result, classical ion-exchange supports, such as Source Q15 or Q30 (GE Healthcare) and TSKgel SuperQ-5PW (Tosoh Bioscience), are often used for routine purifications of oligonucleotides. These supports possess very similar surface chemistries, which incorporate quaternary amines and provide strong ion-exchange interactions. However, as the field of nucleic acid therapeutics evolves, and these therapeutic molecules become more complex due to chemical modifications to the oligonucleotide structure, ion-exchange chromatography may not be adequate to achieve the desired recovery and purity of these modified oligonucleotides. This example describes the evaluation of a mixed-mode stationary phase containing both strong anion- and cation-exchange ligands as well as hydrophobic ligands for purification of a carbohydrate-conjugated oligonucleotide.

Various oligonucleotides containing 2'-O-methyl- and 2'-fluoro-modified nucleotides were conjugated to a triantennary N-acetylgalactosamine (GalNAc)-containing ligand (Structure 1) at either the 5' terminal nucleotide via an aminohexyl linker or the 3' terminal nucleotide via a homoserinyl linker. The structure of the triantennary GalNAc-containing ligand is shown below in Structure 1, where "Ac" represents an acetyl group and "//" represents the point of attachment, via an aminohexyl or homoserinyl linker to the oligonucleotide.

position (a 3'-3' linkage)). Insertion of an "s" in the sequence indicates that the two adjacent nucleotides are connected by a phosphorothiodiester group (e.g. a phosphorothioate internucleotide linkage). Unless indicated otherwise, all other nucleotides are connected by 3'-5' phosphodiester groups.

TABLE 1

GalNAc-conjugated oligonucleotides

| Compound # | Sequence (5'-3') | SEQ ID NO: | GalNAc conjugation site |
|---|---|---|---|
| 47-04 | {Phos}GsusGgGaAgAAAGa uGaAgUuU | 1 | 3' |
| 40-07 | GuGgGaAgAAAGaUgAaGusUsu | 2 | 5' |
| 40-04 | GuGgGaAgAAAGauGaAgUsusU | 3 | 5' |
| 40-01 | gUgGgAaGAAAgAuGaAgUsusU | 4 | 5' |
| 09-01 | GcAgCuGcUACUGgUuCuCuU | 5 | 5' |
| 34-01 | csagccccuUAAacuuauacg s[invdA] | 6 | 5' |
| 13-10 | cuucauGcCUUUcuacagususu | 7 | 5' |
| 13-13 | uucaugCcUUUCuacaguususu | 8 | 5' |

[Structure 1]

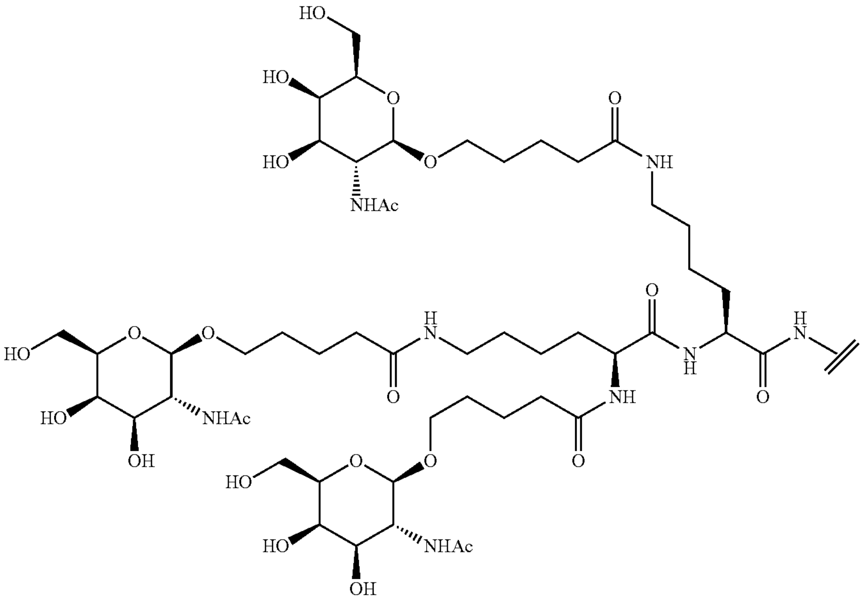

The oligonucleotides were synthesized on a solid support using phosphoramidite chemistry. Table 1 below summarizes the sequence of the oligonucleotides. The nucleotide sequences are listed according to the following notations: dT, dA, dG, dC=corresponding deoxyribonucleotide; a, u, g, and c=corresponding 2'-O-methyl ribonucleotide; A, U, G, and C=corresponding 2'-deoxy-2'-fluoro ("2'-fluoro") ribonucleotide; Phos=terminal nucleotide has a monophosphate group at its 5' end; invAb=inverted abasic nucleotide (i.e. abasic nucleotide linked to adjacent nucleotide via a substituent at its 3' position (a 3'-3' linkage)); and invdX=inverted deoxyribonucleotide (i.e. deoxyribonucleotide linked to adjacent nucleotide via a substituent at its 3'

TABLE 1-continued

GalNAc-conjugated oligonucleotides

| Compound # | Sequence (5'-3') | SEQ ID NO: | GalNAc conjugation site |
|---|---|---|---|
| 13-07 | gcuucaUgCCUUucuacaususu | 9 | 5' |
| 32-10 | [invAb]gcuucaUgCcC UUCuacaususu | 10 | 5' |

TABLE 1-continued

| GalNAc-conjugated oligonucleotides | | | |
|---|---|---|---|
| Compound # | Sequence (5'-3') | SEQ ID NO: | GalNAc conjugation site |
| 32-07 | [invAb]gcuucaUgCCCUu cuacaususu | 11 | 5' |
| 32-04 | [invAb]gcuucaUgCCCU ucuacaususu | 11 | 5' |
| 32-01 | gcuucaUcCCUUucuacausus u | 12 | 5' |
| 24-10 | [invAb]gcuucaUgCCU Uucuacausus u | 13 | 5' (via PS) |
| 24-13 | [invAb]caugccUuUCUAc aguggusus u | 14 | 5' (via PS) |
| 24-16 | [invAb]augccuUuCUACa guggcusus u | 15 | 5' (via PS) |
| 24-19 | [invAb]cugcuuCaUGCCu uucuaasus u | 16 | 5' (via PS) |
| 24-22 | [invAb]gcuucaUgCCUUu cuacaasus u | 17 | 5' (via PS) |
| 24-25 | [invAb]uucaugCcUUUCua caguasus u | 18 | 5' (via PS) |
| 19-04 | [invAb]GcUuCaUgCCUUuc uacausus u | 19 | 5' (via PS) |
| 19-07 | cugcuucaUgCCUUucuac as[invAb] | 20 | 5' (via PS) |
| 08-17 | {Phos}csUscGuAUaaca AuAaggggcusus u | 21 | none |

Figure 1:
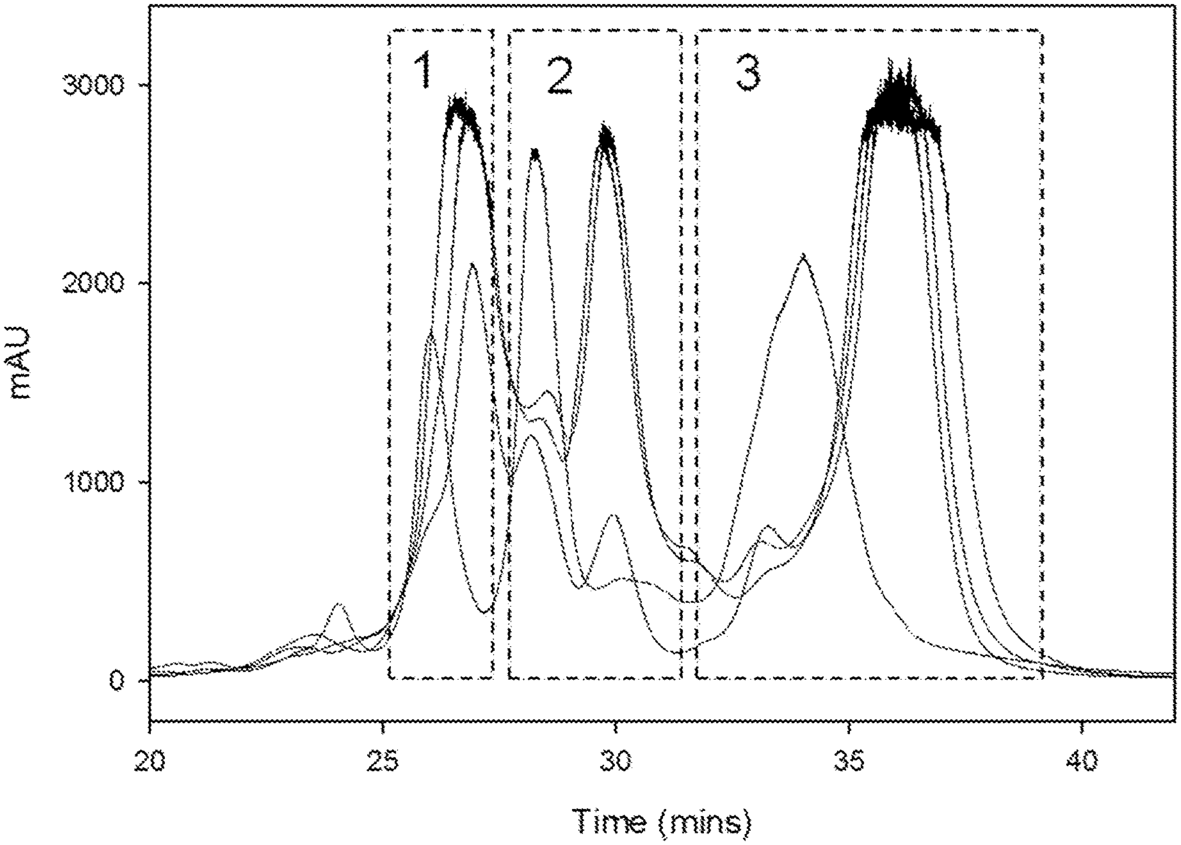
FIG. 1 depicts preparative chromatograms of the purification of four GalNAc-conjugated oligonucleotides (compound nos. 47-04, 40-07, 40-04, and 40-01) using a polymer bead-based anion exchange resin (TSK-gel SuperQ-5PW column). A solution comprising each GalNAc-conjugated oligonucleotide was separated on the TSK-gel SuperQ-5PW column (21.5×150 mm, 13 μm) at a flow rate of 8 mL/min using a 20 mM $Na_2HPO_4$, 10% acetonitrile (v/v) mobile phase, pH 8.5 with elution by an increasing gradient of sodium bromide. Detection was by UV absorbance at 260 nm. Box 1 denotes the peaks corresponding to the intact GalNAc-conjugated oligonucleotide, whereas box 2 highlights the peaks corresponding to unconjugated oligonucleotide. Box 3 encompasses peaks corresponding to higher order structures of the oligonucleotides resulting from secondary interactions.

Initially, four different GalNAc-conjugated oligonucleotides (compound nos. 47-04, 40-07, 40-04, and 40-01) were purified using a conventional polymer bead-based strong anion exchange resin (TSKgel SuperQ-5PW, Tosoh Bioscience). 2-3 mL of the solution containing each of the GalNAc-oligonucleotides was loaded on to the TSKgel Super Q-5PW column (21.5×150 mm, 13 μm) and was separated using a salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M NaBr, pH 8.5) using the following gradient conditions: 0-20% Buffer B in 0-3 min, 20-55% Buffer B in 3-38 min, 55-65% Buffer B in 38-44 min, and hold 20% Buffer B at 45 min to 55 min. The buffers were applied to the column at a flow rate of 8 mL/min, and the separation was conducted at ambient temperature. The results of the separation are shown in FIG. 1. The elution order for all four GalNAc-conjugated oligonucleotides is the intact GalNAc-conjugated oligonucleotide (box 1) followed by the unconjugated oligonucleotide (box 2). The later eluting peaks (box 3) correspond to higher order structures of the oligonucleotides resulting from secondary interactions. A similar profile has been reported for carbohydrate-conjugated oligonucleotides purified with a Resource Q ion-exchange column (GE Healthcare), suggesting both columns provide the same elution order and similar selectivity. See Zhu and Mahato, Bioconjugate Chemistry, Vol. 21: 2119-2127, 2010.

In an effort to improve the separation between the GalNAc-conjugated and unconjugated oligonucleotides, a mixed-mode stationary phase was used. The Scherzo family of columns have stationary phases containing functionalities that allow for both ion-exchange and hydrophobic interactions and are commercially available (Imtakt USA, Portland, OR). Three different Scherzo columns are available: SW-C18, SM-C18, and SS-C18. The columns differ in their ion-exchange capacity with either weak (ionizable) or strong (permanently charged) ion-exchange functionalities, but all contain reversed-phase C18 (octadecyl) groups for hydrophobic interactions. The Scherzo SM-C18 column is the only column with a stationary phase containing weak ion-exchange functional groups, whereas the other two columns have stationary phases that are permanently charged. The ion-exchange capacity among the columns also differs with the Scherzo SS-C18 column having the highest ion exchange capacity followed by the SM-C18 column and then the SW-C18 column. See Biba et al., Journal of Chromatography A, Vol. 1304:69-77, 2013; IMTAKT, Scherzo Family SSO, 2015 at imtaktusa.com. The Scherzo SS-C18 column was selected for purification of the GalNAc-conjugated oligonucleotides. The SS-C18 stationary phase contains strong ionic ligands (quaternary ammonium and sulfonyl groups) and C18 ligands. See, e.g., Choi et al., Forensic Science International, Vol. 259:69-76, 2016.

Figure 2:
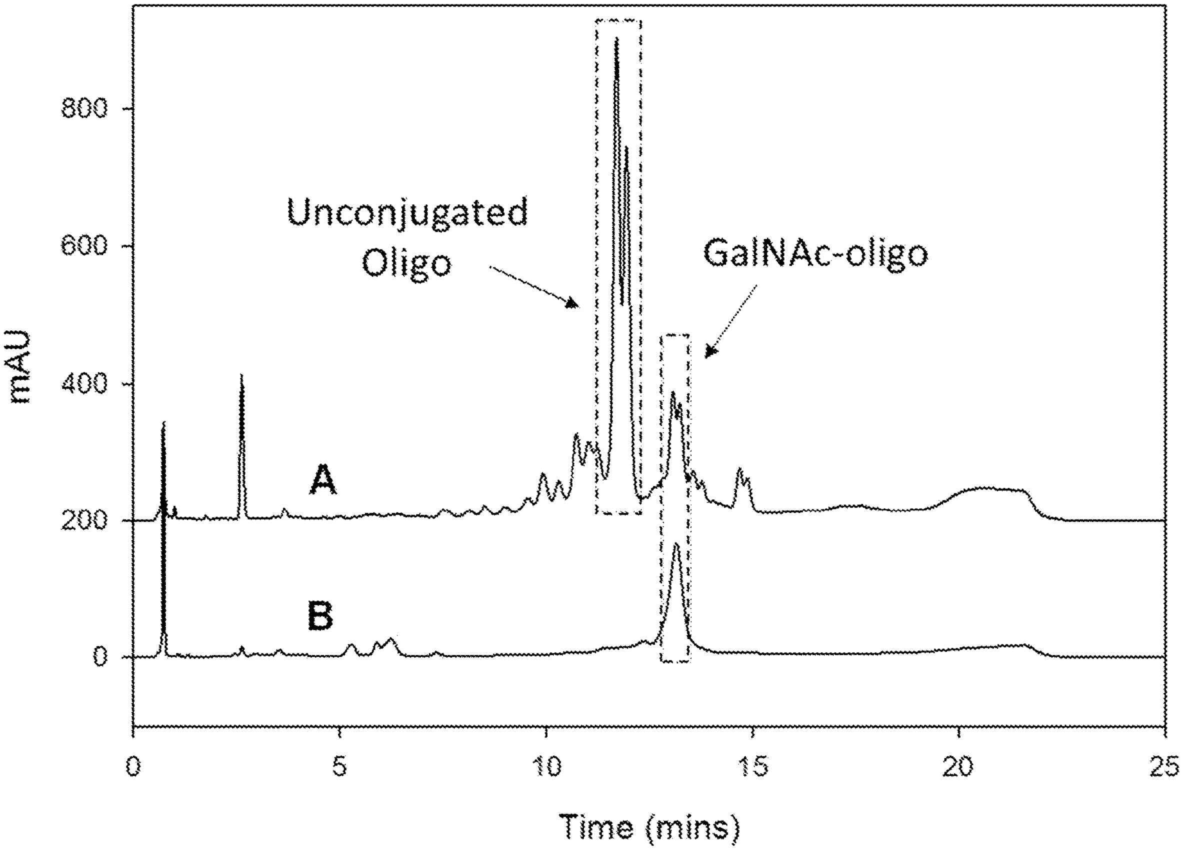
FIG. 2 shows the separation of two GalNAc-conjugated oligonucleotides (compound nos. 40-01 (Trace A) and 09-01 (Trace B)) using a mixed-mode stationary phase (Scherzo SS-C18 column). A solution comprising each GalNAc-conjugated oligonucleotide was separated on the Scherzo SS-C18 column (4.6×50 mm, 3 μm) at a flow rate of 1.5 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 40-70% mobile phase B in 0-20 min, 40% mobile phase B 20.1 min (hold for 5 min). Detection was by UV absorbance at 260 nm.

Two different GalNAc-conjugated oligonucleotides (compound nos. 40-01 and 09-01) were separated using the Scherzo SS-C18 analytical column (4.6×50 mm, 3 μm). A solution containing each of the GalNAc-conjugated oligonucleotides was loaded on to the column and was separated using a salt/acetonitrile gradient, which was created by mixing Buffer A (100 mM Tris, pH 7.5) and Buffer B (100 mM Tris, 20% acetonitrile (v/v), 1 M NaBr, pH 7.5) using the following gradient conditions: 40-70% Buffer B in 0-20 min and hold 40% Buffer B at 20.1 min to 25.1 min. The buffers were applied to the column at a flow rate of 1.5 mL/min, and the separation was conducted at ambient temperature. The results of the separation are shown in FIG. 2. A reversal in the elution order is observed on the Scherzo SS-C18 mixed-mode column as compared to the TSKgel anion-exchange column with the more hydrophobic GalNAc-conjugated oligonucleotide being retained on the column longer than the unconjugated oligonucleotide. Thus, the Scherzo SS-C18 mixed-mode column affords orthogonal separations to TSKgel and Resource Q anion-exchange columns. In addition, the peaks in the chromatogram for the separation of compound no. 40-01 (Trace A in FIG. 2) resemble doublets, indicating possible separation of diastereomers. Note that compound no. 40-01 contains two phosphorothioate internucleotide linkages, thus creating chiral centers, whereas compound no. 09-01 does not contain any phosphorothioate internucleotide linkages. Separation of diastereomers by the Scherzo SS-C18 mixed-mode column is described in more detail in Example 2.

Interestingly, the Scherzo mixed-mode columns were previously evaluated for separations of oligoribonucleotides on an analytical scale. See Biba et al., Journal of Chromatography A, Vol. 1304: 69-77, 2013. Although Biba et al. conclude that both the Scherzo SW-C18 and SM-C18 columns are capable of separating oligoribonucleotides from truncated versions of the oligoribonucleotides using mobile phases containing salt gradients, the authors expressly state that the Scherzo SS-C18 column was deemed unsuitable for oligonucleotide analysis given that no elution of any of the oligonucleotides from the column could be obtained, even with increased mobile phase strength. See page 77, left column, penultimate paragraph of Biba et al. The present inventors discovered that the reversed-phase mode of the column could be leveraged by increasing the amount of an organic modifier (e.g. acetonitrile) in the mobile phase to manipulate the retention of the oligonucleotides on the column. As shown by the results in FIG. 2, elution of oligonucleotides is achievable using the Scherzo SS-C18 column by increasing the concentration of acetonitrile to 20% or more in mobile phase Buffer B in combination with approximately 0.5 to 1 M of salt (e.g. NaCl or NaBr), indicating that both ion-exchange and reverse-phase interactions control retention of the oligonucleotides on the column.

Figure 3:
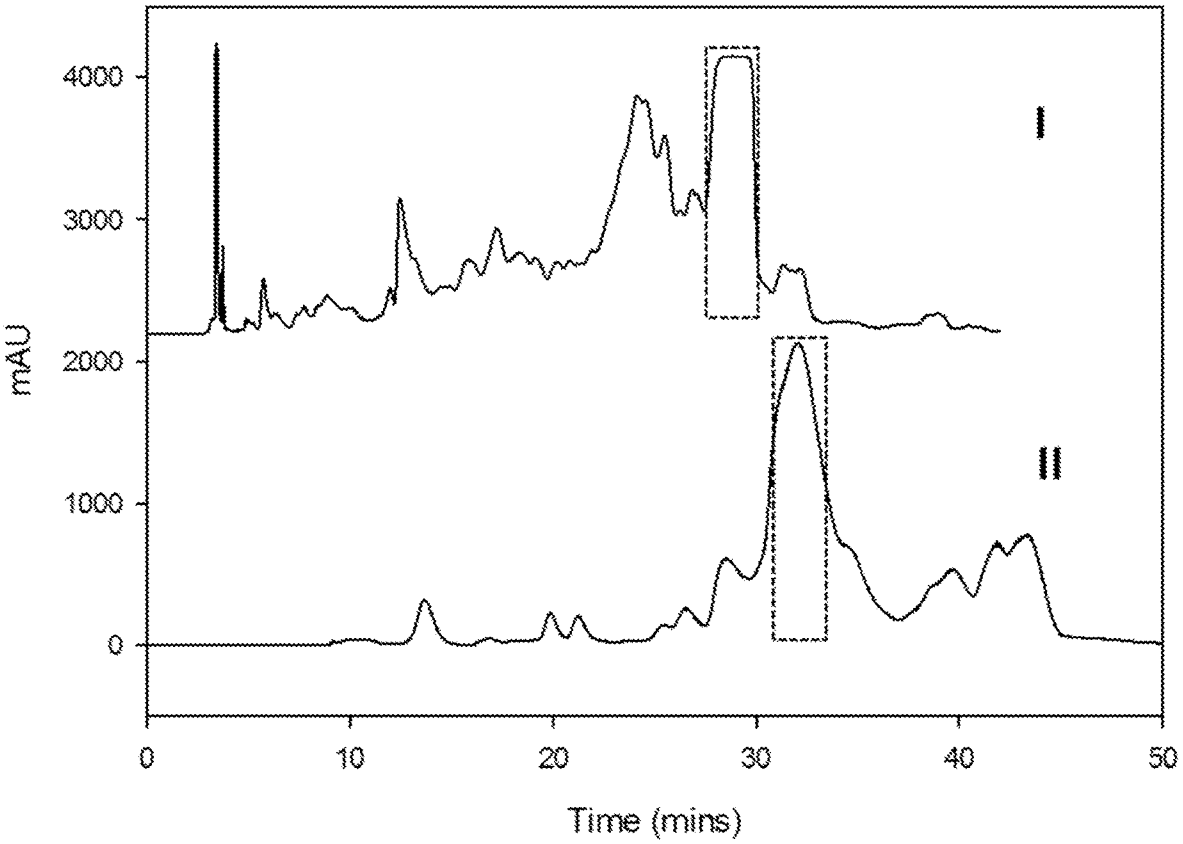
FIG. 3 shows the purification of a GalNAc-conjugated oligonucleotide (compound no. 34-01) using either a mixed-mode stationary phase (Scherzo SS-C18 column; Trace I) or an anion exchange stationary phase (TSK-gel SuperQ-5PW column; Trace II). For the separation shown in Trace I, a solution comprising the GalNAc-conjugated oligonucleotide was separated on the Scherzo SS-C18 column (10×250 mm, 3 μm) at a flow rate of 5 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 55-80% mobile phase B in 0-40 min, 80% mobile phase B at 40-50 min, 55% mobile phase B at 50.1-70 min. For the separation shown in Trace II, a solution comprising the GalNAc-conjugated oligonucleotide was separated on the TSK-gel SuperQ-5PW column (21.5×300 mm, 13 μm) at a flow rate of 8.5 mL/min using a 20 mM $Na_2HPO_4$, 15% acetonitrile (v/v) mobile phase, pH 8.5 with elution by a pH/salt gradient. Detection was by UV absorbance at 260 nm. Dashed boxes represent fractions that were collected for further analysis.

A separate experiment was performed to directly compare purification of a GalNAc-conjugated oligonucleotide (compound no. 34-01) by a Scherzo SS-C18 mixed-mode column or a TSKgel Super Q-5PW anion-exchange column. A solution containing 14.25 mg of the GalNAc-conjugated oligonucleotide was loaded on to either a Scherzo SS-C18 mixed-mode column (10×250 mm, 3 μm) or a TSKgel Super Q-5PW anion-exchange column (21.5 mm×300 mm (2×150 mm columns), 13 μm). The separation conditions for the Scherzo SS-C18 column were as follows: mobile phase applied at a flow rate of 5 mL/min; mobile phase Buffer A: 100 mM Tris, pH 7.5; mobile phase Buffer B: 100 mM Tris, 20% acetonitrile (v/v), 1 M NaBr, pH 7.5; gradient conditions: 55-80% Buffer B in 0-40 min, 80% Buffer B at 40-50 min, and 55% Buffer B at 50.1-70 min. The separation conditions for the TSKgel Super Q-5PW column were as follows: mobile phase applied at a flow rate of 8.5 mL/min; mobile phase Buffer A: 20 mM $Na_2HPO_4$, 15% acetonitrile (v/v), pH 8.5; mobile phase Buffer B: 20 mM $Na_2HPO_4$, 15% acetonitrile (v/v), 1 M NaCl, pH 11; gradient conditions: 0-40% Buffer B in 0-7 min, 40-65% Buffer B at 7-67 min, and 80% Buffer B at 67-87 min. For both columns, the separations were conducted at ambient temperature. The results of the separations are shown in FIG. 3, and the recovery and purity of the GalNAc-conjugated oligonucleotide from each separation with the two different stationary phases are summarized in Table 2. Fractions denoted by the dashed boxes in FIG. 3 were collected and desalted by size exclusion chromatography (HiPrep 26/10 desalting column; 26×100 mm, 90 μm particle size; mobile phase: 80:20 water:ethanol; flow rate 10 mL/min).

TABLE 2

Summary of recovery and purity for a GalNAc-conjugated oligonucleotide (compound no. 34-01)

| Column type | Crude sample amount injected (mg)* | Peak of interest amount injected (mg)** | Recovery (mg)*** | Recovery (%) | Final purity (%) |
|---|---|---|---|---|---|
| Scherzo SS-C18 | 14.25 | 10.7 | 7.8 | 73 | 95 |
| TSKgel-Super Q-5PW | 14.25 | 10.7 | 3.7 | 35 | 91 |

*Nanodrop One spectrophotometer was used to determine the concentration and the amount of the “crude sample injected.”
**The amount of the “crude sample injected” was multiplied by the purity providing the “peak of interest amount injected”
*Recovery was obtained using the Nanodrop One spectrophotometer after purification but prior to desalting by size exclusion chromatography The Scherzo SS-C18 column afforded a faster separation with sharper peaks as compared to the TSKgel Super Q-5PW column (FIG. 3**; compare Trace I to Trace II). Importantly, purification on the Scherzo SS-C18 column provided greater recovery of the GalNAc-conjugated oligonucleotide than that obtained with the TSKgel Super Q-5PW column with 73% of the conjugated oligonucleotide recovered on the SS-C18 column compared to only 35% recovered on the Super Q-5PW column (Table 2). The purity of the GalNAc-conjugated oligonucleotide is also improved with separation on the Scherzo SS-C18 column with 95% purity achieved as compared to 91% purity obtained with the Super Q-5PW column (Table 2). These results demonstrate that the semi-preparative mixed-mode support with a 10 mm inner diameter (ID.) is capable of purifying sufficient quantities of GalNAc-conjugated oligonucleotides and offers the possibility of even larger gram-scale purifications. Purification using mixed-mode chromatography provides an improved method for purifying carbohydrate-conjugated oligonucleotides as compared to anion-exchange chromatography.

Figure 4A:
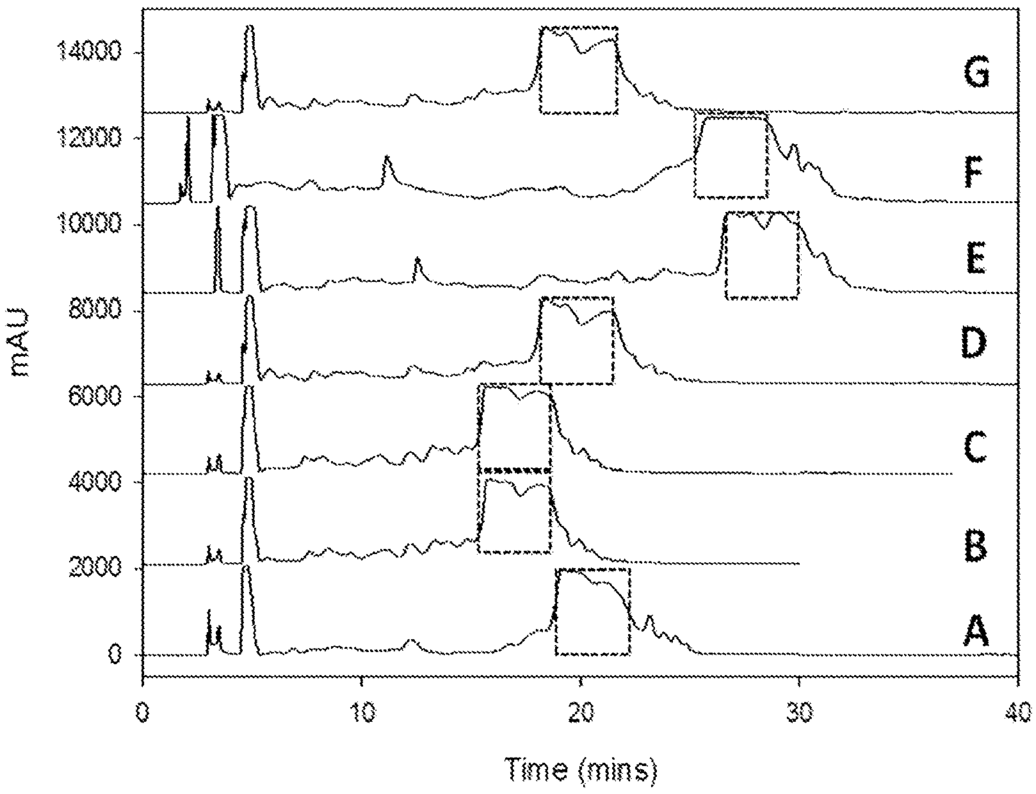
FIG. 4A depicts preparative chromatograms of the separation of various GalNAc-conjugated oligonucleotides using a mixed-mode stationary phase (Scherzo SS-C18 column). A solution comprising each GalNAc-conjugated oligonucleotide was separated on the Scherzo SS-C18 column (10×250 mm, 3 μm) at a flow rate of 5 mL/min. Mobile phase consisted of 100 mM Tris, pH 7.5 (mobile phase A) and 1 M NaBr in 100 mM Tris, 20% (v/v) acetonitrile, pH 7.5 (mobile phase B). Gradient conditions were: 55-80% mobile phase B in 0-40 min, 80% mobile phase B at 40-50 min, 55% mobile phase B at 50.1-70 min. Traces A-G correspond to separations for compound nos. 13-10, 13-13, 13-07, 32-10, 32-07, 32-04, and 32-01, respectively. Detection was by UV absorbance at 260 nm. Dashed boxes represent fractions that were collected for further analysis.
Figure 4B:
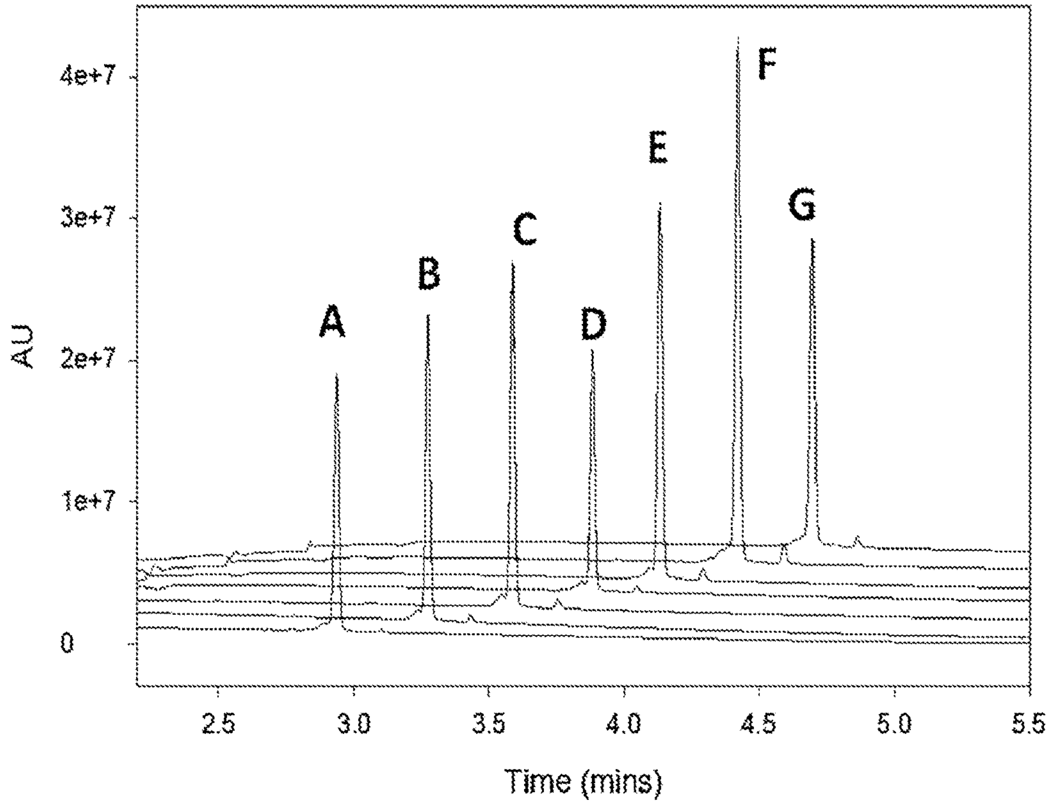
FIG. 4B shows ion-pairing reversed phase liquid chromatograms of collected fractions from the preparative mixed-mode chromatography separations shown in FIG. 4A. Collected fractions (denoted by the dashed boxes in FIG. 4A) comprising each of the GalNAc-conjugated oligonucleotides were combined, de-salted, and analyzed by ion-pairing reversed phase liquid chromatography using a Waters Xbridge BEH OST C18 column (2.1×50 mm, 1.7

Next, various GalNAc-conjugated oligonucleotides having different structural characteristics were tested to evaluate the applicability of the purification method using mixed-mode chromatography described above. Compounds 13-10, 13-13, 13-07, 32-10, 32-07, 32-04, and 32-01 were purified using the Scherzo SS-C18 column (10×250 mm, 3 μm). The sequences and chemical modifications for these compounds are provided in Table 1 above. A solution containing each of the GalNAc-conjugated oligonucleotides was loaded on to the column and was separated using a salt/acetonitrile gradient, which was created by mixing Buffer A (100 mM Tris, pH 7.5) and Buffer B (100 mM Tris, 20% acetonitrile (v/v), 1 M NaBr, pH 7.5) using the following gradient conditions: 55-80% Buffer B in 0-40 min, 80% Buffer B at 40-50 min, and 55% Buffer B at 50.1-70 min. The buffers were applied to the column at a flow rate of 5 mL/min, and the separations were conducted at ambient temperature. Fractions denoted with dashed boxes in FIG. 4A were collected, combined, and desalted by size exclusion chromatography (HiPrep 26/10 desalting column; 26×100 mm, 90 μm particle size; mobile phase: 80:20 water:ethanol; flow rate 10 mL/min). The combined fractions were analyzed by an analytical ion-pairing reversed phase high performance liquid chromatography-mass spectrometry (HPLC-MS) method (Waters Xbridge BEH OST C18 column, 2.1×50 mm, 1.7 μm particle size; 0.6 mL/min flow rate; temperature 60° C.) to determine the purity of the GalNAc-conjugated oligonucleotides in the fractions. The preparative chromatograms for each of the GalNAc-conjugated oligonucleotides is shown in FIG. 4A, whereas the ion-pairing reversed phase liquid chromatograms for the final, de-salted samples are shown in FIG. 4B. Most of the GalNAc-conjugated oligonucleotides eluted from the preparative mixed-mode column by 25 minutes (FIG. 4A). The final purities and recoveries for each of the compounds are summarized in Table 3. Final purities ranged from 92% to 94%, whereas recoveries ranged from 29% to 57%. In contrast to the recoveries reported in Table 2, the recoveries for this experiment were calculated following desalting, which results in sample loss, typically in the 10-20% range. No deterioration in the performance of the Scherzo SS-C18 column by injecting highly basic samples prepared in concentrated ammonia was observed, even though the operating pH range of this column provided by the manufacturer is reported to be 1.5 to 8. The preservation of column performance was likely the result of the use of well-buffered solutions for the mobile phase (e.g. containing 100 mM TRIS, adjusted to pH of 7.5).

TABLE 3

Summary of recovery and purity for various GalNAc-conjugated oligonucleotides

| Compound No. | Crude sample load (mg) | Initial purity (%) | Amount of sample injected (mg) | Recovery, post purification/ desalting (mg) | Recovery, post purification/ desalting (%) | Final purity (%) |
|---|---|---|---|---|---|---|
| 13-10 (A) | 14.8 | ~70 | 10.4 | 3.0 | 29 | 92 |
| 13-13 (B) | 10.7 | ~70 | 7.5 | 4.0 | 53 | 92 |
| 13-07 (C) | 20.0 | ~70 | 14.0 | 8.0 | 57 | 94 |
| 32-10 (D) | 8.7 | ~70 | 6.1 | 2.2 | 36 | 92 |
| 32-07 (E) | 10.1 | ~70 | 7.1 | 3.0 | 42 | 92 |
| 32-04 (F) | 8.4 | ~70 | 5.9 | 2.7 | 46 | 94 |
| 32-01 (G) | 8.7 | ~70 | 6.1 | 2.2 | 36 | 94 |

In another set of experiments, the purification method using the Scherzo SS-C18 mixed-mode column was applied to two crude samples containing different GalNAc-conjugated oligonucleotides with initial purities in the 20-25% range. The inventors' previous experience with such low-purity starting samples of GalNAc-conjugated oligonucleotides suggested that anion exchange chromatography-based methods (e.g. such as the use of a TSKgel Super Q-5PW column) are typically unable to provide a purity greater than 90% and adequate recovery. A solution containing each GalNAc-conjugated oligonucleotide (compound no. 19-04 or compound no. 19-07) was loaded on to the Scherzo SS-C18 column (10×250 mm, 3 μm) and was separated using a salt/acetonitrile gradient, which was created by mixing Buffer A (100 mM Tris, pH 7.5) and Buffer B (100 mM Tris, 20% acetonitrile (v/v), 1 M NaBr, pH 7.5) using the following gradient conditions: 45-70% Buffer B in 0-40 min, 70-80% Buffer B at 40-45 min, 80% Buffer B at 45-50 min, and 45% Buffer B at 51-66 min. The buffers were applied to the column at a flow rate of 5 mL/min, and the separations were conducted at ambient temperature. Fractions denoted with dashed boxes in FIG. 5 were collected, combined, and desalted by size exclusion chromatography (HiPrep 26/10 desalting column; 26×100 mm, 90 μm particle size; mobile phase: 80:20 water:ethanol; flow rate 10 mL/min). The combined fractions were analyzed by an analytical ion-pairing reversed phase HPLC-MS method (Waters Xbridge BEH OST C18 column, 2.1×50 mm, 1.7 μm particle size; 0.6 mL/min flow rate; temperature 60° C.) to determine the purity of the GalNAc-conjugated oligonucleotides in the fractions. Preparative chromatograms are shown in FIG. 5, and the summary of the purity and recovery of the final, de-salted samples is provided in Table 4. As shown in Table 4, the final samples exhibited purities greater than 90%.

TABLE 4

Summary of recovery and purity for select GalNAc-conjugated oligonucleotides

| Compound No. | Crude sample load (mg) | Initial purity (%) | Peak of interest load (mg) | Recovery, post purification/ desalting (mg) | Recovery, post purification/ desalting (%) | Final purity (%) |
|---|---|---|---|---|---|---|
| 19-04 (A) | 10.7 | 25 | 2.7 | 1.2 | 44 | 94 |
| 19-07 (B) | 11.7 | 20 | 2.3 | 1.4 | 61 | 93 |

Taken together, the results of the experiments described in this Example demonstrate that use of mixed-mode chromatography afforded more than double the recovery and enabled higher purity as compared to anion exchange chromatography for GalNAc-conjugated oligonucleotides. The mixed-mode chromatography method proved to be suitable for purifying a variety of GalNAc-conjugated oligonucleotides as application of the method to conjugates having distinct structural characteristics yielded high recoveries and purities in the 92-94% range.

Example 2. Separation of Phosphorothioate Diastereomers

As observed in a previous experiment described in Example 1, the mixed-mode stationary phase appeared to provide separation of diastereomers. To explore this result further, a solution comprising compound no. 08-17, which contains four phosphorothioate internucleotide linkages, thereby creating four chiral centers, was separated using either a Scherzo SS-C18 mixed-mode analytical column (4.6×50 mm, 3 μm) or a TSKgel Super Q-5PW anion-exchange analytical column (7.5 mm×75 mm, 10 μm). The separation conditions for the Scherzo SS-C18 analytical column were as follows: mobile phase applied at a flow rate of 1 mL/min; mobile phase Buffer A: 100 mM Tris, pH 7.5; mobile phase Buffer B: 100 mM Tris, 20% acetonitrile (v/v), 1 M NaBr, pH 7.5; gradient conditions: 55-80% Buffer B in 0-8 min, 80% Buffer B at 8-10 min, and 55% Buffer B at 10.1-12 min. The separation conditions for the TSKgel Super Q-5PW analytical column were as follows: mobile phase applied at a flow rate of 2 mL/min; mobile phase Buffer A: 20 mM $Na_2HPO_4$, 15% acetonitrile (v/v), pH 8.5; mobile phase Buffer B: 20 mM $Na_2HPO_4$, 15% acetonitrile (v/v), 1 M NaCl, pH 11; gradient conditions: 0-45% Buffer B in 0-0.75 min, 45-80% Buffer B at 0.75-6.00 min, 80-100% Buffer B at 6.00-6.10 min, 100% Buffer B at 6.10-7.00 min, and 0% Buffer B at 7.10 min. For both columns, the separations were conducted at ambient temperature. The results of the separations are shown in FIG. 6, which demonstrate that the mixed-mode stationary phase provides a superior separation as compared to the anion exchange stationary phase as evidenced by the presence of multiple peaks. The multiple peaks may represent separation of diastereomers.

Next, a sample containing the same compound no. 08-17 was purified using a semi-preparative Scherzo SS-C18 mixed-mode column. The sample was loaded on to the Scherzo SS-C18 column (10×250 mm, 3 μm) and was separated using a salt/acetonitrile gradient, which was created by mixing Buffer A (100 mM Tris, pH 7.5) and Buffer B (100 mM Tris, 20% acetonitrile (v/v), 1 M NaBr, pH 7.5) using the following gradient conditions: 45-70% Buffer B in 0-40 min, 70-80% Buffer B at 40-45 min, 80% Buffer B at 45-50 min, and 45% Buffer B at 51-66 min. The buffer was applied to the column at a flow rate of 5 mL/min, and the separation was conducted at ambient temperature. The resulting preparative chromatogram is shown in FIG. 7A. The peak profile is similar to that obtained with the analytical column (FIG. 6), but the separation has been substantially improved, primarily due to the increased length of the semi-preparative column. Peaks labeled 1, 2, and 3 in FIG. 7A were collected as separate fractions, desalted by size exclusion chromatography (HiPrep 26/10 desalting column; 26×100 mm, 90 μm particle size; mobile phase: 80:20 water:ethanol; flow rate 10 mL/min), and analyzed by an analytical ion-pairing reversed phase HPLC-MS method (Waters Xbridge BEH OST C18 column, 2.1×50 mm, 1.7 μm particle size; 0.6 mL/min flow rate; temperature 60° C.) to confirm the identity of the analytes in each fraction. The ion-pairing reversed phase liquid chromatograms for each of the three fractions is shown in FIG. 7B. Each fraction comprises predominantly a single peak and exhibits purities greater than 90% and equivalent m/z values (FIG. 7B and data not shown). The single peaks still likely represent a mixture of diastereomers. Nevertheless, the Scherzo SS-C18 mixed-mode column provides a novel approach for better separations of phosphorothioate diastereomers on a preparative scale.

In a separate experiment, six different GalNAc-conjugated oligonucleotides each having two phosphorothioate internucleotide linkages, but otherwise having different structural characteristics were purified using the Scherzo SS-C18 mixed-mode semi-preparative column to determine whether separation of diastereomers could again be observed. Compounds 24-10, 24-13, 24-16, 24-19, 24-22, and 24-25 were purified using the Scherzo SS-C18 column (10×250 mm, 3 μm). The sequences and chemical modifications for these compounds are provided in Table 1 above. A solution containing each of the GalNAc-conjugated oligonucleotides was loaded on to the column and was separated using a salt/acetonitrile gradient, which was created by mixing Buffer A (100 mM Tris, pH 7.5) and Buffer B (100 mM Tris, 20% acetonitrile (v/v), 1 M NaBr, pH 7.5) using the following gradient conditions: 55-80% Buffer B in 0-40 min, 80% Buffer B at 40-50 min, and 55% Buffer B at 50.1-70 min. The buffers were applied to the column at a flow rate of 5 mL/min, and the separations were conducted at ambient temperature. Fractions denoted with dashed boxes in FIG. 8A were collected, combined, and desalted by size exclusion chromatography (HiPrep 26/10 desalting column; 26×100 mm, 90 μm particle size; mobile phase: 80:20 water:ethanol; flow rate 10 mL/min). The combined fractions were analyzed by an analytical ion-pairing reversed phase HPLC-MS method (Waters Xbridge BEH OST C18 column, 2.1×50 mm, 1.7 μm particle size; 0.6 mL/min flow rate; temperature 60° C.) to determine the purity of the GalNAc-conjugated oligonucleotides in the fractions. The preparative chromatograms for each of the GalNAc-conjugated oligonucleotides is shown in FIG. 8A, whereas the ion-pairing reversed phase liquid chromatograms for the final, de-salted samples are shown in FIG. 8B. The final purities and recoveries for each of the compounds are summarized in Table 5.

TABLE 5

Summary of recovery and purity for select GalNAc-conjugated oligonucleotides

| Compound No. | Crude sample load (mg) | Initial purity (%) | Amount of sample injected (mg) | Recovery, post purification/ desalting (mg) | Recovery, post purification/ desalting (%) | Final purity (%) |
|---|---|---|---|---|---|---|
| 24-10 (A) | 15.7 | ~45 | 7.1 | 2.8 | 39 | 93 |
| 24-13 (B) | 17.7 | ~45 | 8.0 | 2.5 | 31 | 94 |
| 24-16 (C) | 15.1 | ~45 | 6.8 | 2.2 | 32 | 94 |
| 24-19 (D) | 16.2 | ~45 | 7.3 | 2.9 | 40 | 92 |
| 24-22 (E) | 17.1 | ~45 | 7.7 | 3.0 | 39 | 92 |
| 24-25 (F) | 14.9 | ~45 | 6.7 | 1.9 | 28 | 90 |

The final purities of the compounds were 90% or greater, and recoveries ranged from 28% to 40%, which is consistent with the purities and recoveries for structurally-distinct GalNAc-conjugated oligonucleotides using this stationary phase. See Table 3. As shown by the multiple peaks in the preparative chromatograms depicted in FIG. 8A, separation of the phosphorothioate diastereomers was observed. The diastereomer separation is further evident in the analytical chromatograms of the isolated fractions from the preparative purification shown in FIG. 8B. Doublets of the peaks were observed representing analytes with the same m/z values. Although only the fractions shown in the dotted boxes in FIG. 8A were combined, the neighboring peaks adjacent to the fractions that were combined also revealed the same m/z value, indicating the presence of diastereomers. Although the semi-preparative Scherzo SS-C18 column does not offer a baseline separation of all the possible phosphorothioate diastereomers, it provides a significant improvement in diastereomer separation as compared to the anion exchange chromatography-based methods, such as those employing the TSKgel Super Q-5PW column.

Example 3. Purification of GalNAc-Conjugated Oligonucleotides Using Anion-Exchange Chromatography This example describes an alternative method for separating carbohydrate-conjugated oligonucleotides using anion exchange chromatography. The use of pH gradients to elute oligonucleotides from a weak anion-exchange column has been previously reported. See Zimmermann et al., J.

Chromatogr A, Vol. 1354: 43-55, 2014. The elution occurred over a very narrow pH range from 7 to 8, and the changes in elution and selectivity were largely attributed to ionization changes of the stationary phase (Zimmermann et al., 2014). In contrast, the method described in this example utilizes a permanently charged stationary phase and employs a pH gradient from 8.5 to 11 to modulate ionization of the carbohydrate-conjugated oligonucleotide. It has been reported that an increase in pH enhances ionization of G, T and U bases, thereby increasing the overall negative charge of the oligonucleotide and influencing separation selectivity (McGinnis et al., J Chromatogr B, Vol. 883-884:76-94, 2012 and Thayer et al., J Chromatogr B, Vol. 878: 933-941, 2010). Increased pH has also been reported to reduce secondary interactions, making ion-exchange purifications more straightforward (McCarthy et al., J. Anal. Biochem., Vol. 390: 181-188, 2009). A dual pH/salt gradient elution was developed for a polymer bead-based strong anion exchange resin (TSKgel SuperQ-5PW, Tosoh Bioscience) to enhance the separation of a GalNAc-conjugated oligonucleotide from impurities.

A GalNAc-conjugated oligonucleotide (compound no. 34-01; see Table 1 for structural characteristics) was separated from impurities using a TSKgel SuperQ-5PW anion-exchange analytical column (7.5×75 mm, 10 μm) with elution by either a salt gradient at constant pH or a dual salt and pH gradient. Under the first set of conditions (FIG. 9A, trace B), a solution containing the GalNAc-conjugated oligonucleotide was loaded on to the column and was separated using a salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M NaBr, pH 8.5) using the following gradient conditions: 30-60% Buffer B in 0.75-5.00 min; 60-65% Buffer B from 5.00-5.50 min; 65-70% Buffer B from 5.50-6.00 min; 70% Buffer B from 6.00-9.00 min; and 0% Buffer B at 9.1 min. Under the second set of conditions (FIG. 9A, trace A), a solution containing the GalNAc-conjugated oligonucleotide was loaded on to the column and was separated using a dual pH/salt gradient, which was created by mixing Buffer A (20 mM $Na_2HPO_4$, 10% acetonitrile (v/v), pH 8.5) and Buffer B (20 mM $Na_2HPO_4$, 10% acetonitrile (v/v), 1 M NaBr, pH 11) using the same gradient parameters as those described immediately above for the salt gradient. The buffers were applied to the column at a flow rate of 2 mL/min, and the separation was conducted at 40° C.

Next, the components of the mobile phase for the dual pH/salt gradient elution method were adjusted to optimize the separation of the intact GalNAc-conjugated oligonucleotide from its unconjugated counterpart. Different salts and concentration of organic modifier (e.g. acetonitrile) in the mobile phase were evaluated. Specifically, the mobile phase buffers in each of the three sets of conditions were:

Condition 1:

Buffer A1: 20 mM $Na_2HPO_4$, 10% acetonitrile (v/v), pH 8.5

Buffer B1: 20 mM $Na_2HPO_4$, 10% acetonitrile (v/v), 1 M NaBr, pH 11

Condition 2:

Buffer A2: 20 mM $Na_2HPO_4$, 10% acetonitrile (v/v), pH 8.5

Buffer B2: 20 mM $Na_2HPO_4$, 10% acetonitrile (v/v), 1 M NaCl, pH 11

Condition 3:

Buffer A3: 20 mM $Na_2HPO_4$, 15% acetonitrile (v/v), pH 8.5

Buffer B3: 20 mM $Na_2HPO_4$, 15% acetonitrile (v/v), 1 M NaCl, pH 11

A solution containing the GalNAc-conjugated oligonucleotide (compound no. 34-01) was loaded onto a TSKgel SuperQ-5PW anion-exchange analytical column (7.5×75 mm, 10 μm) and separated at 25° C. with a mobile phase flow rate of 2 mL/min using a dual pH/salt gradient generated by mixing the two buffers set forth above for each of the conditions as follows:

| Time (min) | % Buffer B (B1, B2, or B3) |
|---|---|
| 0.75 | 30 |
| 15 | 65 |
| 16 | 70 |
| 19 | 70 |
| 19.1 | 0 |

FIG. 9B shows the chromatograms for the separations using the different mobile phase buffers with the different counter anions or organic modifier concentrations. Chloride counter anion in the mobile phase provided the highest selectivity in combination with 15% acetonitrile affording the best separation (FIG. 9B, trace C) and purities in the 96-97% range (data not shown) for the gram-scale purification of this GalNAc-conjugated oligonucleotide. Exemplary conditions for the preparative purification are:

Column: TSKgel SuperQ-5PW (21.5×300 mm, 13 μm)

Flow rate: 8.5 mL/min

Temperature: ambient (e.g. 18° C. to 24° C.)

Mobile phase:

Buffer A: 20 mM $Na_2HPO_4$, 15% (v/v) acetonitrile, pH 8.5

Buffer B: 20 mM $Na_2HPO_4$, 15% (v/v) acetonitrile, 1 M NaCl, pH 11

Gradient purification conditions:

| Time (min) | % Buffer B |
|---|---|
| 0 | 0 |
| 7 | 40 |
| 67 | 65 |
| 67.1 | 80 |
| 87.1 | 80 |

A solution containing compound no. 34-01 was purified at preparative scale using similar preparative conditions as described above. Specifically, two TSKgel SuperQ-5PW columns (each column: 21.5×150 mm, 13 μm) were linked in series and the solution (1.2 mL) was loaded on to the first of the two linked columns. The separation was carried out at ambient temperature with a mobile phase flow rate of 8.5 mL/min using a dual pH/salt gradient. The gradient was created by mixing Buffer A (20 mM $Na_2HPO_4$, 15% (v/v) acetonitrile, pH 8.5) and Buffer B (20 mM $Na_2HPO_4$, 15% (v/v) acetonitrile, 1 M NaCl, pH 11) according to the following gradient conditions: 0-30% Buffer B at 0-7 min, 30-65% Buffer B at 7-63 min, 65-70% Buffer B at 63-63.1 min, 70% Buffer B at 63.1-66 min, and re-equilibration with Buffer A (100%) from 66 min-80 min. The resulting preparative chromatogram is shown in FIG. 9C. The peak profile is similar to that obtained with the analytical column (FIG. 9B, trace C).

A summary of the parameters for the analytical ion-pairing reversed phase chromatographic method and the desalting method described in the Examples are listed below:

Analytical Ion-Pairing Reversed Phase Liquid Chromatography-Mass Spectrometry Method Column: Waters Xbridge BEH OST C18 (2.1×50 mm, 1.7 µm)

Flow rate: 0.6 mL/min

Temperature: 60° C.

Mobile phase:

Buffer A: 15.7 mM N,N-Diisopropylethylamine (DIEA), 50 mM Hexafluoro-2-propanol (HIP) in water Buffer B: 15.7 mM DIEA, 50 mM HFIP in water: acetonitrile (50:50)

Gradient purification conditions:

| Time (min) | % Buffer B |
|---|---|
| 0 | 10 |
| 9.0 | 40 |
| 9.1 | 10 |
| 11.0 | 10 |

Detection: Diode Array Detector at 260 nm, followed by mass spectrometry

Desalting (Size Exclusion Chromatography)

Column: HiPrep 26/10 Desalting column (26×100 mm, 90 µm)

Mobile phase: 80:20 water:ethanol

Flow rate=10 mL/min

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method for purifying a carbohydrate-oligonucleotide conjugate compound from one or more impurities, comprising:

contacting a solution comprising the carbohydrate-oligonucleotide conjugate compound and one or more impurities with a mixed-mode matrix, wherein the mixed-mode matrix comprises a strong anion exchange ligand, a strong cation exchange ligand, and a hydrophobic ligand, wherein the strong anion exchange ligand comprises a quaternary amine, the strong cation exchange ligand comprises a sulfonyl functional group, and the hydrophobic ligand comprises an octadecyl carbon chain;

passing a mobile phase through the mixed-mode matrix, wherein the mobile phase has a pH of about 7.0 to about 8.5 and comprises a buffer, acetonitrile, and an elution salt selected from the group consisting of sodium bromide, potassium bromide, ammonium bromide, sodium chloride, potassium chloride, and ammonium chloride, and wherein the concentration of acetonitrile in the mobile phase increases as a gradient from about 8% (v/v) to about 20% (v/v) and the concentration of the elution salt increases as a gradient from about 0.5 M to about 1 M; and collecting elution fractions from the mixed-mode matrix, wherein one or more impurities are eluted in a first set of elution fractions and the carbohydrate-oligonucleotide conjugate compound is eluted in a second set of elution fractions, thereby separating the carbohydrate-oligonucleotide conjugate compound from the impurities, wherein the carbohydrate-oligonucleotide conjugate compound comprises a trivalent or tetravalent N-acetyl-galactosamine moiety covalently linked, optionally through a linker moiety, to an oligonucleotide that is about 10 nucleotides in length to about 50 nucleotides in length.

2. The method of claim 1, wherein the mixed-mode matrix has a pore size less than 20 nm.

3. The method of claim 1, wherein the mixed-mode matrix has a pore size from about 8 nm to about 15 nm.

4. The method of claim 1, wherein the buffer is sodium phosphate, Tris hydrochloride, HEPES, or MOPS.

5. The method of claim 1, wherein the increase in concentration of acetonitrile in the mobile phase is a gradient from about 10% (v/v) to about 18% (v/v).

6. The method of claim 1, wherein the gradient of acetonitrile is a step gradient.

7. The method of claim 1, wherein the gradient of acetonitrile is a linear gradient.

8. The method of claim 1, wherein the elution salt is sodium bromide.

9. The method of claim 1, wherein the gradient of the elution salt is a step gradient.

10. The method of claim 1, wherein the gradient of the elution salt is a linear gradient.

11. The method of claim 1, wherein the mobile phase has a pH of about 7.0 to about 8.0 and comprises about 20 mM to about 200 mM Tris hydrochloride buffer, acetonitrile, and sodium bromide, and wherein the concentration of acetonitrile increases at a gradient of about 8% (v/v) to about 20% (v/v) and the concentration of sodium bromide increases at a gradient of about 0.5 M to about 1 M over time.

12. The method of claim 11, wherein the mobile phase has a pH of about 7.5 and comprises about 100 mM Tris hydrochloride buffer, acetonitrile, and sodium bromide, and wherein the concentration of acetonitrile increases at a gradient of about 11% (v/v) to about 17% (v/v) and the concentration of sodium bromide increases at a gradient of about 0.5 M to about 0.85 M over time.

13. The method of claim 1, wherein the oligonucleotide in the carbohydrate-oligonucleotide conjugate compound comprises at least one modified nucleotide.

14. The method of claim 13, wherein the modified nucleotide is a 2'-modified nucleotide.

15. The method of claim 13, wherein the modified nucleotide is a 2'-fluoro modified nucleotide, a 2'-O-methyl modified nucleotide, a 2'-O-methoxyethyl modified nucleotide, a 2'-O-allyl modified nucleotide, a bicyclic nucleic acid (BNA), or combinations thereof.

16. The method of claim 1, wherein the oligonucleotide in the carbohydrate-oligonucleotide conjugate compound comprises at least one phosphorothioate internucleotide linkage.

17. The method of claim 16, wherein the solution comprising the carbohydrate-oligonucleotide conjugate compound further comprises one or more phosphorothioate diastereomers of the conjugate compound, and wherein a first diastereomer elutes in a separate set of elution fractions than a second diastereomer.

18. The method of claim 1, wherein the oligonucleotide in the carbohydrate-oligonucleotide conjugate compound is about 15 nucleotides in length to about 30 nucleotides in length.

19. The method of claim 1, further comprising isolating the set of elution fractions comprising the carbohydrate-oligonucleotide conjugate compound and subjecting the fractions comprising the carbohydrate-oligonucleotide conjugate compound to anion-exchange chromatography.

20. The method of claim 1, wherein the solution comprising the carbohydrate-oligonucleotide conjugate compound and one or more impurities is an eluate from an anion-exchange chromatography matrix.

21. The method of claim 1, wherein the N-acetyl-galactosamine moiety in the carbohydrate-oligonucleotide conjugate compound has the following structure:

[Structure 1]

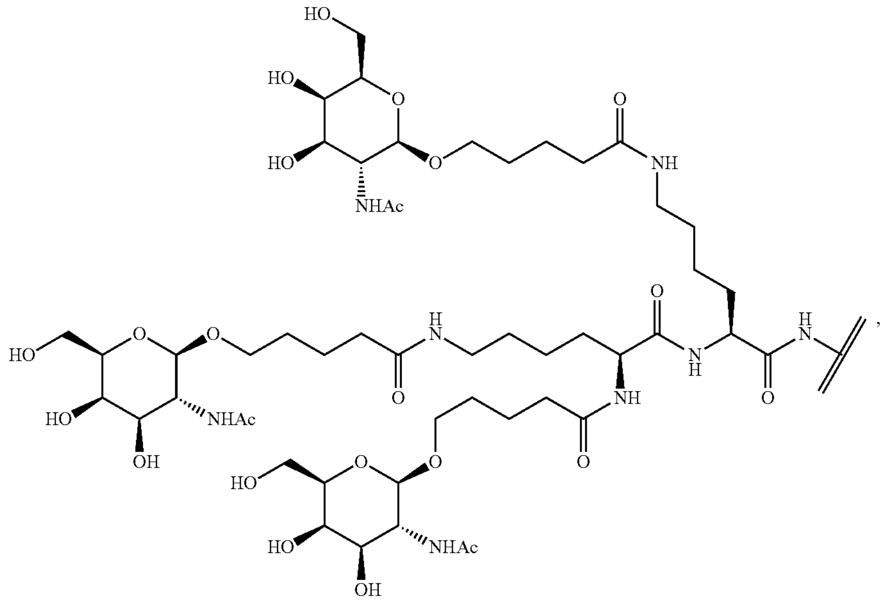

wherein Ac represents an acetyl group and//represents the point of attachment, optionally through a linker, to the oligonucleotide.

22. The method of claim 1, wherein the oligonucleotide in the carbohydrate-oligonucleotide conjugate compound comprises one or more 2'-fluoro modified nucleotides, 2'-O-methyl modified nucleotides, or combinations thereof.

23. The method of claim 1, wherein the mixed-mode matrix comprises a density of the strong anion exchange ligand and the strong cation exchange ligand of 450 μmol/gram or greater.

* * * * *